(12) United States Patent
Cochran

(10) Patent No.: US 7,918,801 B2
(45) Date of Patent: Apr. 5, 2011

(54) SENSORS FOR MONITORING MOVEMENTS, APPARATUS AND SYSTEMS THEREFOR, AND METHODS FOR MANUFACTURE AND USE

(75) Inventor: William T. Cochran, Clermont, FL (US)

(73) Assignee: Medility LLC, Clermont, FL (US)

( * ) Notice: Subject to any disclaimer, the term of this patent is extended or adjusted under 35 U.S.C. 154(b) by 1497 days.

(21) Appl. No.: 11/321,161

(22) Filed: Dec. 29, 2005

(65) Prior Publication Data

US 2007/0167879 A1    Jul. 19, 2007

(51) Int. Cl.
*A61B 5/08* (2006.01)
(52) U.S. Cl. ... 600/534; 600/587; 600/588; 324/207.11; 73/862.331
(58) Field of Classification Search ............ 600/304, 600/551, 587–593, 437, 438, 459; 324/206, 324/207.11–207.26; 73/862.331–862.337
See application file for complete search history.

(56) References Cited

U.S. PATENT DOCUMENTS

| | | | |
|---|---|---|---|
| 2,408,524 A | 10/1946 | Mestas | |
| 2,459,210 A | 1/1949 | Ashcraft | |
| 3,020,527 A | 2/1962 | MacLaren | |
| 3,268,845 A | 8/1966 | Whitmore | |
| 3,483,861 A | 12/1969 | Tiep | |
| 3,891,918 A * | 6/1975 | Ellis | 324/207.16 |
| 4,308,872 A | 1/1982 | Watson | |
| 4,339,953 A * | 7/1982 | Iwasaki | 73/654 |
| 4,373,534 A | 2/1983 | Watson | |
| 4,408,159 A | 10/1983 | Prox | |
| 4,777,962 A | 10/1988 | Watson | |
| 4,807,640 A | 2/1989 | Watson | |
| 4,813,435 A | 3/1989 | Arms | |
| 4,817,625 A | 4/1989 | Miles | |
| 5,036,275 A | 7/1991 | Munch | |
| 5,069,221 A | 12/1991 | Smith | |
| 5,159,935 A | 11/1992 | Sackner | |
| 5,216,364 A * | 6/1993 | Ko et al. | 324/207.24 |
| 5,329,932 A | 7/1994 | Yount | |
| 5,331,968 A | 7/1994 | Williams | |
| 5,497,147 A | 3/1996 | Arms | |
| 5,642,043 A | 6/1997 | Ko | |
| 5,743,143 A * | 4/1998 | Carpenter et al. | 74/335 |
| 5,760,577 A | 6/1998 | Shizuya | |

(Continued)

OTHER PUBLICATIONS

Micro-Epsilon, "Inductive Displacement Sensors and Gaging Sensors," Catalog of Micro-Epsilon, pp. 1-8.

(Continued)

*Primary Examiner* — Charles A Marmor, II
*Assistant Examiner* — Michael D'Angelo
(74) *Attorney, Agent, or Firm* — Charles C. Krawczyk; Catherine A. Lewis

(57) ABSTRACT

Sensors, apparatus, and methods for measuring movements are disclosed. The sensors include input and output windings wound about a common location and an armature is equally positioned relative to both windings movable to vary inductance reactance of the sensor. The mass of the sensor and the ease of movements are such that flexible membranes, such as skin, can be monitored with insignificant interference. The sensor can be included in "Band-aid" bandage arrangement in which the bandage backing can be removed and held in place on skin by the bandage. A monitoring circuit, responsive to the changes in sensor impedance, provides indications of the detected movements. The monitoring circuit includes an arrangement for self-adjusting parameters so that the system can be automatically preset and continually reset. The monitoring circuit includes a power savings arrangement.

8 Claims, 34 Drawing Sheets

U.S. PATENT DOCUMENTS

| | | |
|---|---|---|
| 5,777,467 A | 7/1998 | Arms |
| 5,902,250 A | 5/1999 | Verrier |
| 5,914,593 A | 6/1999 | Arms |
| 6,142,953 A | 11/2000 | Burton |
| 6,340,884 B1 | 1/2002 | Wolf |
| 6,356,075 B1 | 3/2002 | Shank |
| 6,413,225 B1 | 7/2002 | Sackner |
| 6,433,629 B2 | 8/2002 | Hamel |
| 6,461,307 B1 | 10/2002 | Kristbjarnarson |
| 6,479,986 B1 | 11/2002 | Steinich |
| 6,529,127 B2 | 3/2003 | Townsend |
| 6,551,252 B2 | 4/2003 | Sackner |
| 6,622,567 B1 | 9/2003 | Hamel |
| 6,714,763 B2 | 3/2004 | Hamel |
| 6,781,366 B2 | 8/2004 | Hiramatsu |
| 6,810,753 B2 | 11/2004 | Valdevit |
| 6,810,754 B2 * | 11/2004 | May ................ 73/862.333 |
| 6,853,183 B2 * | 2/2005 | Kindler ................ 324/207.17 |
| 6,926,679 B2 * | 8/2005 | Friedrichs ................ 600/588 |
| 2005/0093537 A1 | 5/2005 | Townsend |

OTHER PUBLICATIONS

Singer Instruments & Control, "SM Series LVDT," Catalog of Singer Instruments & Control, LTD. Year 2003, 1 page.

Micro Strain, "Differential Variable Reluctance Transducer," Catalog of Micro Strain, pp. 1 & 2.

Analog Devices, "LVDT Signal Conditioner," Catalog of Analog Devices for product AD598. pp. 1-16.

David S. Nyce, "The LVDT: A Simple and Accurate Position Sensor," Aug. 2005, Sensor Technology and Design, pp. 1-7.

Phillips Medical Systems, "FM-2 Antepartum Portable fetal monitor," Catalog of Phillips Medical Systems. pp. 1-4.

* cited by examiner

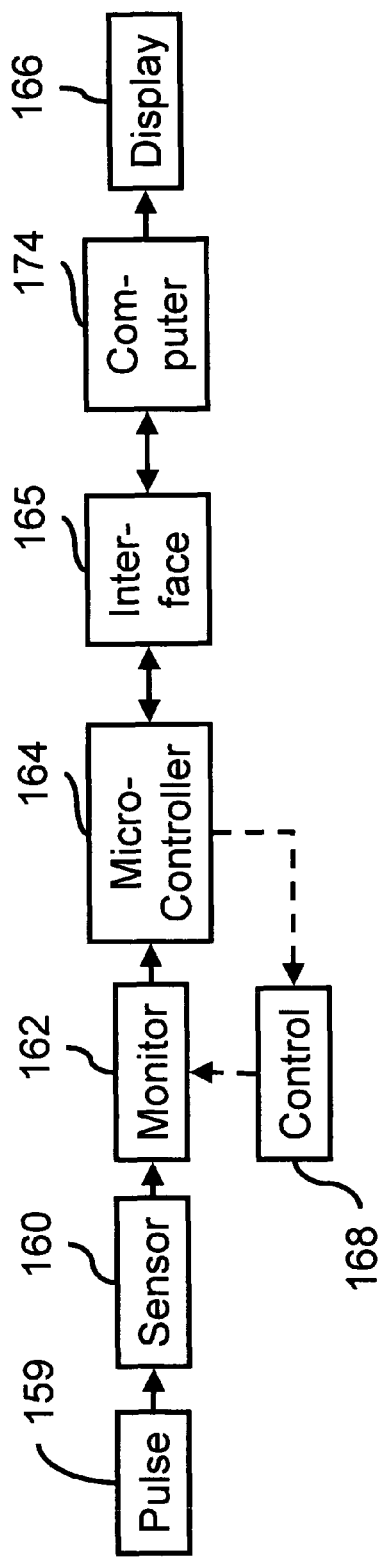
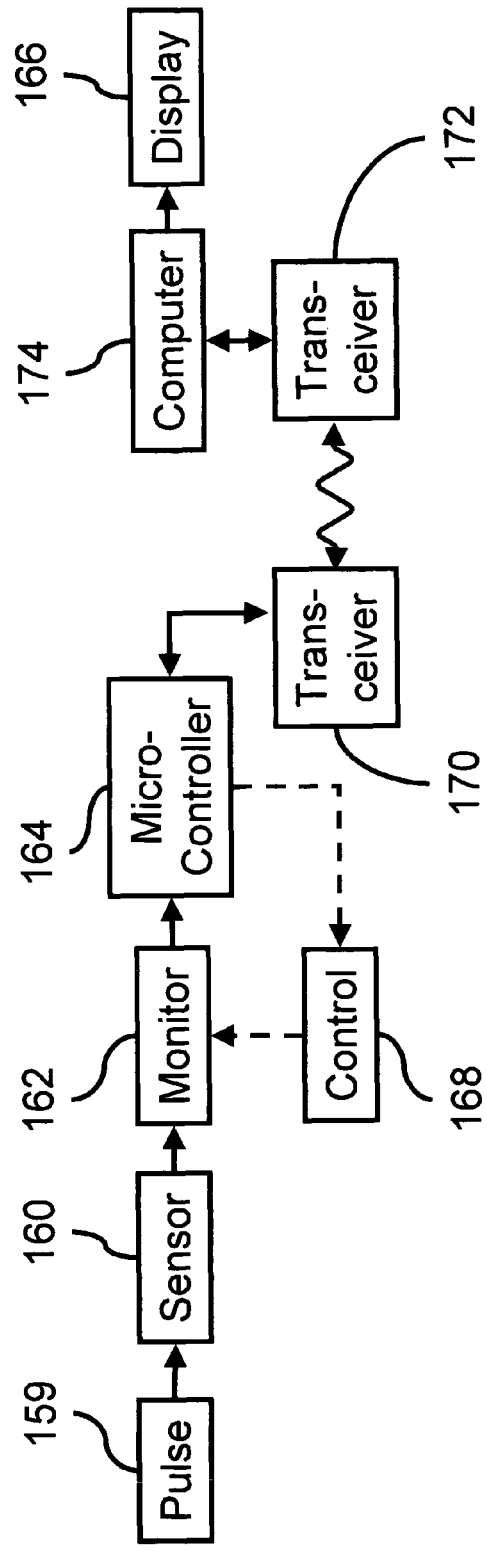
Figure 15
Figure 16

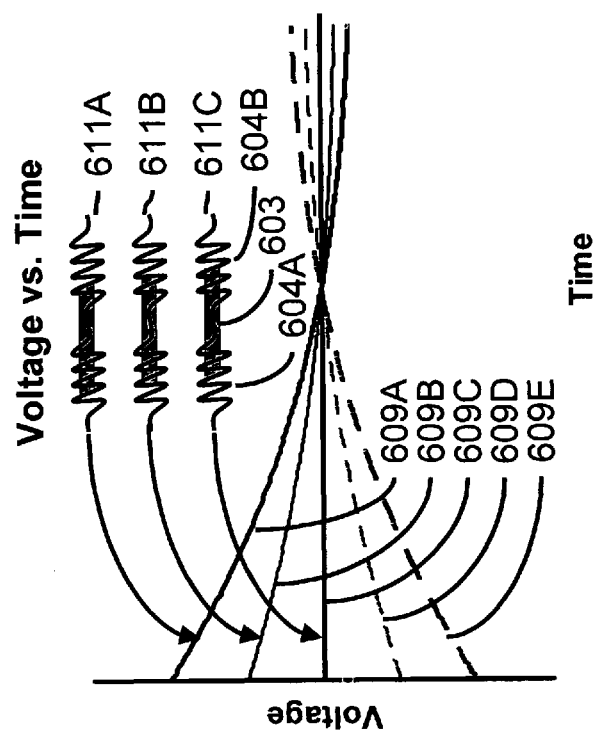
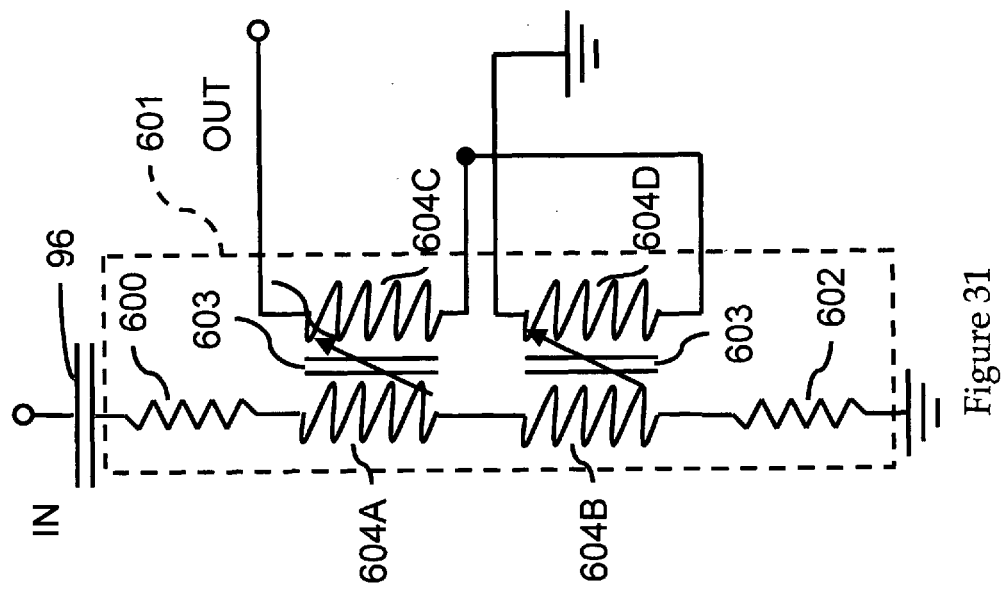
Figure 32
Figure 31

SENSORS FOR MONITORING MOVEMENTS, APPARATUS AND SYSTEMS THEREFOR, AND METHODS FOR MANUFACTURE AND USE

FIELD OF INVENTION

The present invention generally relates to sensors for monitoring movements in the form of deformations and displacements, apparatus, systems and method for use with the sensor, and methods for manufacture of the sensor, to provide control, visual, and audible indications of the movements, and more particularly to arrangements for measuring the changes in flexible membranes such as for example skin.

BACKGROUND OF THE INVENTION

With the ever increasing growth of automated systems used in various types of industrial and medical systems, there is a need for new and improved sensors and signal processing apparatus for monitoring movements related to force, torque, speed, acceleration, contraction, expansion, deformation, displacement, and the like. There is also a need to miniaturize such sensors to make measurements not otherwise possible with large and bulky sensors. For example, when monitoring the displacements of small or fragile items, or when monitoring deformations of flexible membranes such as skin, it is important that the sensor mass, attachments, electrical connections, and its operation do not interfere with the movements being monitored that might otherwise significantly impact the accuracy of the measurements.

Such sensors and signal processing apparatus should preferably be subject to low manufacturing costs, not require high tolerance fits for moving parts, provide a sizable range of linear operation, and yet be relatively rugged.

Linear variable differential transformer (LVDT) type sensors are widely in use for making displacement measurements. A LVDT sensor is disclosed in the U.S. Pat. No. 5,216,364, issued on Jun. 1, 1993, entitled "Variable Transformer Position Sensor" includes mechanical structures that are useful for automotive shock absorbers but are too massive in design to readily miniaturized or to be applied to monitoring delicate items or flexible membranes. Miniaturized sensors based on the LVDT technology are disclosed in catalog publications by Micro-Epsilon entitled "Inductive Displacement Sensors and Linear Gaging Sensors," and by Singer Instruments and Control, Ltd. entitled "SM Series LVTD." These sensors include a primary or input winding and two secondary or output windings transformer coupled to a movable core.

The U.S. Pat. No. 5,497,147, issued on Mar. 5, 1996, and entitled "Differential Variable Reluctance Transducer," and U.S. Pat. No. 5,777,467, issued on Jul. 7, 1998, and entitled "Miniaturized Displacement Transducer Assembly," and publication by MicroStrain entitled "Differential Variable Reluctance Transducer" (DVTR) disclose sensors that include two output coils and depend upon the differential reluctance between the coils controlled by a movable core for monitoring displacements by using sine wave excitation and synchronous demodulation. The close operating tolerances of the sensor require a highly flexible core structure of super elastic material to achieve the free sliding fit between the core and the coils to be robust to mechanical damage.

The U.S. Pat. No. 3,891,918, issued on Jun. 24, 1975, and entitled "Linear Displacement Transducer Utilizing An Oscillator Whose Average Period Varies as a Linear Function of the Displacement," includes a single coil winding or two windings and a core as a variable inductance. One or both of the sensor windings controls the frequency of an oscillator circuit in a well-known manner to provide signals for measuring displacements.

The sensors in the U.S. Pat. No. 5,216,364, and the Micro-Epsilon and the Singer publications, and in a publication by Analog Devices entitled "LVDT Signal Conditioner AD598 (Rev A)" and a publication by David S. Nyce of Revolution Sensor Company entitled "The LVDT a Simple and Accurate Position Sensor" dated August 2005 disclose arrangements where constant sinusoidal excitation signals are applied to the primary winding of frequencies of 20 Hz to 12 KHz, depending on the sensor, and wherein alternating current signals are induced in both secondary windings with amplitudes depending on the core position that are added or subtracted to generate measurement signals.

The Q (quality factor) of a coil is defined as the ratio of the inductive reactance to the resistance of the coil at a given frequency. Q is a measure of the efficiency of storing energy; the higher the Q the more efficient the coil. To increase the Q in the abovementioned sensors, either the frequency applied to the sensors is to be increased, or the sensor inductive reactance increased (by the number of coil turns squared), or the sensor internal resistance is decreased. However, the miniaturization does not scale well due to Q restraints. As the dimensions of these sensors are decreased, primarily by reducing the size of the wire, the internal resistance of the sensor coils increases significantly. It would be advantageous if the sensor design were not limited by Q restraints, allowing miniaturization by the use of smaller gauge wires with its inherent increase of internal resistance without materially impacting the sensor performance.

The sensor systems identified above disclose the continuous application of signals to the sensors and a continuous power supply for energizing the signal processing circuitry. It would be advantageous if an arrangement would be provided that such sensor systems would require substantial power draw only during signal and data processing. An arrangement for reducing power consumption is disclosed in the U.S. Pat. No. 6,433,629, issued Aug. 13, 2002, entitled "Micropower Differential Sensor Measurement," wherein power for the system is temporarily developed from a transmitted magnetic field for a duration to allow a pulse to be applied to a Wheatstone sensor bridge circuit, a comparison made, and an RF signal transmitted for data processing. The disclosed power generating arrangement is time consuming requiring rectification and filtering of the magnetic field and the stabilization of the power supply before signal processing is initiated.

The pulse energization of the sensor Wheatstone bridge circuit arrangement, as disclosed in the U.S. Pat. No. 6,433,629, requires the comparison of signals based on a non-linear RC or LR exponentially curved decay rates.

Temperature variations or gradients place limitations on the absolute accuracy of variable impedance inductive sensors. For example, the intrinsic resistance of the windings of the sensor coils changes with variations in temperature. In addition, the permeability of metallic sensor cores changes with variations in temperature introducing changes in sensor inductance. In the U.S. Pat. No. 5,914,593, issued on Jun. 22, 1999, entitled "Temperature Gradient Compensation Circuit," and United States Patent Application Publication No. 2005/0093537, published on May 5, 2005, entitled "Circuit for Compensating for Time Variation of Temperature in an Inductive Sensor," such temperature sensitive changes in sensor impedance are electronically compensated by the use of a Wheatstone bridge sensor circuit configuration including the application of AC and DC signals to the bridge circuit to obtain temperature offset correction signals. It would be desirable if the sensors could be configured in circuit arrangements that provide self-temperature compensation.

In the field of medicine there is continual research and development for the design of new equipment for monitoring body volume changes to measure internal physiological properties, such as the chest for problems dealing with sleep apnea and the abdomen for pregnancy labors. The present solutions require the use of belt and/or vest type sensing arrangements. For sleep apnea the vests and belts surround the chest torso such as disclosed in many United States patents, of which the following are sample patents: U.S. Pat. No. 5,329,932, issued Jul. 19, 1994, entitled "Method of and Apparatus for Monitoring Respiration and Conductive Composition Used Therewith," U.S. Pat. No. 6,142,953, issued Nov. 7, 2000, entitled "Respiratory Inductive Plethysmography Band Transducer," U.S. Pat. No. 6,413,225, issued Jul. 2, 2002, entitled "Quantitative Calibration of Breathing Monitors with Transducers Placed on Both Rib Cage and Abdomen," U.S. Pat. No. 6,461,307, issued Oct. 8, 2002, entitled "Disposable Sensor for Measuring Respiration," and U.S. Pat. No. 6,551,252, issued Apr. 22, 2003, entitled "Systems and Method for Ambulatory Monitoring of Physiological Signs." For pregnancy labors, the belts surround the abdomen such as disclosed in a Philips Medical Systems Nederland B.V. publication entitled "FM-2 Antepartum Portable Fetal Monitor." Each of these apparatus is bulky and as a result may be relatively uncomfortable to wear for extended periods of time, particularly if required to wear them overnight. Furthermore, although the apparatus may be portable, they are cumbersome, and may interfere with daily activities and sleep.

The use of commercial strain gauges to measure deformations or the body was found unworkable in that the attachment of such strain gauges to the body interfered with the movements of the part of the skin to which the gauges were attached rendering their use questionable.

There is a need to replace these massive and cumbersome belts and vest apparatus that encircle the body or cover large portions of the torso, and avoid short-term and long-term patient discomfort that may accompany their use. The apparatus should preferably be attached and worn with minimal discomfort, allowing the patient a significant amount of freedom of movement without impacting the tests underway. The apparatus should also preferably have a high degree of sensitivity to allow the equipment to detect small changes, particularly when testing infants, and be capable of continued operation as the patient changes positions.

It would be advantageous if the connection of the sensing apparatus to the body could be made similar to a "Band-aid" tape type arrangement so that the attachment can be simplified and made by technicians, and that the associated monitoring equipment can be easily set up and maintained in operation.

Further it would be advantageous if the sensor could be subject to miniaturization so that appropriate electronics and transmission circuitry could be designed attached to the body for radio, infrared, etc, transmission of data to remote locations. It would also be advantageous for portability purposes if such sensors and circuitry could be powered by small wrist-watch type batteries and still perform for time periods needed to complete the tests before replacement is needed.

In addition, it would advantageous if the monitoring apparatus was adaptable for use over a wide variety of portions of the body for observing a wide variety of physiological problems.

SUMMARY

The sensors, system, apparatus and methods disclosed provide means for monitoring movements or deformations of objects. As used herein the term movements means alterations of form or shape, or deformations, or displacements, of objects to be monitored, such as, but not limited to, contractions, expansions, shape changes, volume changes, twisting, stretching, and ripple and wave actions. The loose tolerance between moving sensor parts enables the sensor to be used in monitoring movements of delicate items. The sensor is particularly adaptable to miniaturization, wherein the mass of the sensor, the loose tolerance between moving sensor parts, and the flexible electrical connections thereto, enables the sensor to be used in monitoring deformations, contraction and expansion, or other shape changes of flexible membranes such as experienced when monitoring skin, with insignificant interference with the movements. The movements may be elastic such as the contraction and expansion of skin, or plastic movements wherein residues of the changes remain.

The sensor includes a coil having an input winding and an output winding concentrically wound about a common location, and an armature or core that extends with approximately equal positioning within both windings and moves within the coil to vary the sensor inductive reactance as exhibited by the output winding.

The value of the resistive, capacitive and inductive components can be selected so that the arrangement can operate as a critically damped, under damped, or over damped LRC circuit for providing definitive points for the measurement of changes in inductive reactance. The choice of L, R. and C determine the number of zero crossing points (polarity changes) and the magnitude of the negative portion of the signal The sensor is essentially Q insensitive in its design, enabling the sensor to be manufactured in a variety of sizes to fit various monitoring needs, and is particularly adapted to miniaturization in that the use of smaller wire and its inherent higher intrinsic resistance does not impact the sensor performance.

The sensor, because of its miniaturization feature, can be included, in accordance to another embodiment of the invention, as part of a "Band-aid" type of tape package that encapsulates the sensor and allows its application and attachment to the skin in the form of a bandage.

The sensor is adapted to be coupled to a monitoring circuit that is responsive to the changes in the inductive reactance of the sensor to provide outputs that are indicative of the movements.

A further feature of the monitoring circuit includes a control circuit to preset the monitoring circuit system parameters to adapt the operating range of the system to the scope of the displacement of the sensor.

The monitoring system is also adapted to provide two outputs, one of which is an absolute indication of the sensor positioning and the other provides a relative and more sensitive indication.

The monitoring circuit has the capability of providing high sensitivity operation by the use of amplification. In the event the monitoring circuit is driven into nonlinear operation by the scope of sensor movements, a control circuit adapts the system parameters of the monitoring circuit to accommodate to the scope of sensor movements.

Electrical pulses are applied to the sensor and decaying electrical responses are monitored that are a function of changes in inductive reactance of the sensor. The sensor provides, in response to an input pulse, an output signal that has a zero voltage cross point, or polarity change. The monitoring circuit uses the zero cross over point as a reference for initiating measurements of sensor displacements. The control circuit sets the monitoring circuit's initial operating parameters adjacent to the cross over reference and thereafter modifies its operation to follow subsequent cross over changes.

A magnitude based monitoring circuit selects a time slot between pulses to analyze the magnitude of the sensor responses to provide an output indicative of the relative movement of the items monitored. The control circuit controls the timing between the pulses and the time slot to adapt the system to handle the scope of responses from the sensor. The gain of the monitoring circuit can also be modified by the control circuit so as to adapt the system to the scope of sensor movements.

A further feature comprises a timer circuit that is initiated after the pulse is applied to the sensor and stopped when a selected magnitude of the sensor response is reached, wherein the count provides indications of the deformations being monitored. A control system can be added to adapt the system operating parameters to accommodate the scope of sensor responses.

A still further feature of the monitoring system comprises a combination of the time or count based system and the magnitude based system to provide two separate indications of deformations. A control system can be added to adapt the operating parameters of one, or both, the time based system and the magnitude based systems to accommodate the scope of sensor responses.

The combination of the sensor and the monitoring system provides a means by which data measurements of indications of movements can be achieved in very short periods of time allowing the system to be placed in a low power (sleep) mode of operation between data sets. This is particularly useful in battery powered portable apparatus wherein the sleep mode will significantly extend the operating life of the battery.

The sensing system is particularly adaptable for use in the measurement of deformation of skin such as contraction and expansion as a means for measuring local body volume changes, large volume changes, ripple or wave change action and shape changes when analyzing various internal body physiological properties, such as sleep apnea, baby crib death, pregnancy labor cramps, bladder incontinence, erectile dysfunction, muscle tension and contractions and limb movements. The sensor is also adapted to be attached to the body in arrays for providing multiple-directional analysis.

The sensor is adapted to be connected in various arrangements wherein the outputs can be arranged to monitor movements relative to a zero reference point and provide directions of movements relative to the reference point, or provide very accurate indications of movements, or temperature insensitive indications of movements.

BRIEF DESCRIPTION OF THE FIGURES

FIG. 15 is a basic block diagram of the sensor monitoring system of the invention.

FIG. 16 is a block diagram of the system of FIG. 15 modified for wireless operation.

FIG. 31 includes a schematic diagram of a sensor circuit of the invention including a single excitation winding and two pick up windings.

FIG. 32 includes waveforms for illustrating the operation of the sensor circuit of FIG. 31

DETAILED DESCRIPTION OF THE INVENTION

Although the sensor, system, apparatus, and methods of the invention shall be primarily described herein for use in monitoring movements a flexible membrane, such as for medical applications in monitoring small motions and deformations in skin, it should be understood that the use of the invention is equally applicable to monitor movements and deformations for a wide variety of objects involved in industrial and commercial applications.

There is continual medical research underway for ways to measure body internal pressures by external, non-intrusive means. The skin surface tension serves as a buffer between the internal and external body systems. External skin deformation provides indications of many body internal physiological properties. The external surface of the skin flexes in the form of deformations due to body volume changes, local volume changes, ripple or wave action, shape changes, and limb movements. For example, the volume of air in the lungs when breathing in and out is reflected in chest skin deformations in the form of contractions and expansions on the both back and front sides of the chest. Bodily functions that create changes in the body volume or shape can be monitored through such skin deformations. Such data can potentially be used to detect, diagnose, and provide bio-feedback for conditions such as incontinence, sleep apnea, erectile dysfunction, and pregnancy labor contractions. Further, muscle changes due to cramps, or relaxation such in the case of anesthesia, can also be monitored by measuring skin deformations. As another example, the rate and direction of local swelling could easily be monitored.

Figure 1:
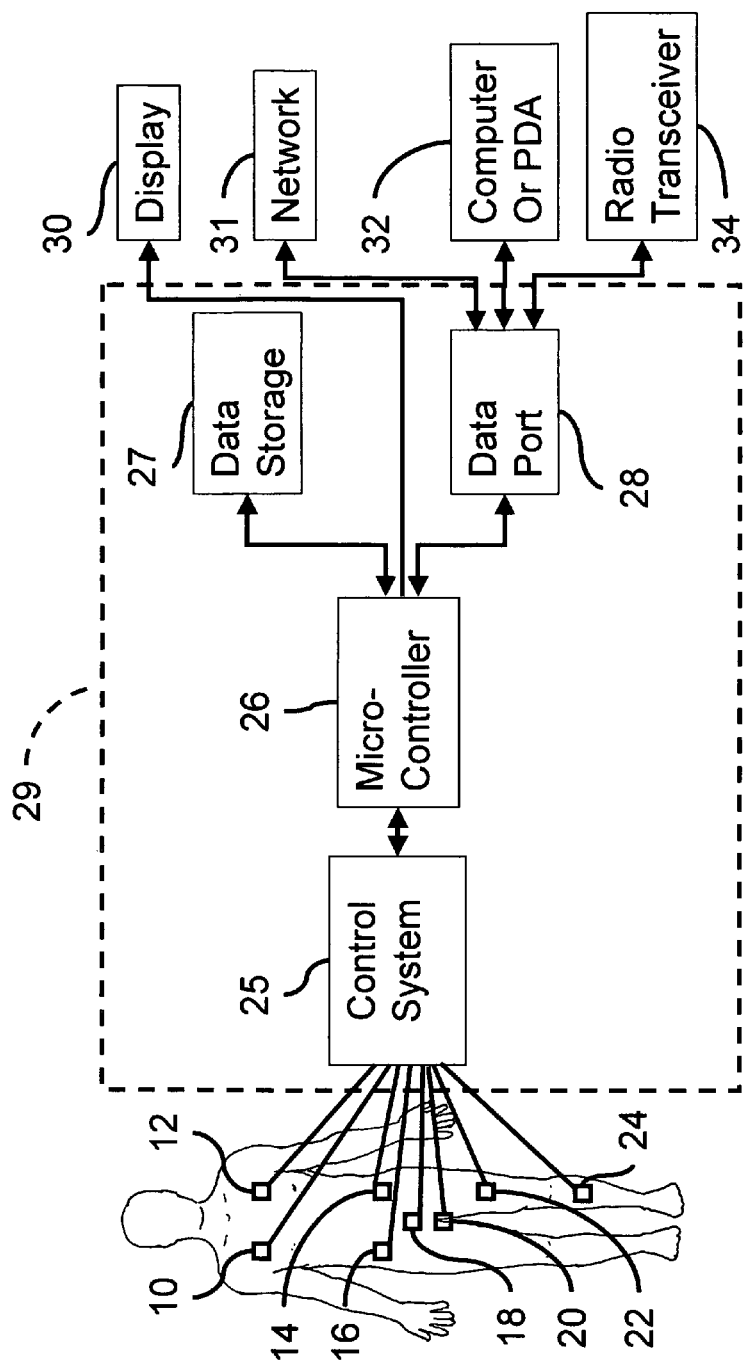
FIG. 1 illustrates the sensor system of the invention connected for monitoring skin deformations at various parts of the human body.

In FIG. 1 sensors 10-24 of the invention are shown attached to body skin at various body locations. Sensors 10 and 12 are attached to the chest to monitor skin deformations due to respiration to detect sleep apnea or to avoid baby crib death. Sensors 14 and 16 are attached to the abdomen to monitor skin deformations such as experienced with labor during pregnancy. Sensor 18 is attached to the skin adjacent the bladder to monitor urination needs. Sensor 20 is attached to the penis area to monitor erectile dysfunction. Sensors 22 and 24 are attached to monitor leg muscle tension. Although the sensors 10-24 have been illustrated as attached to the front of the body, they could also be attached to the body back and other locations where it is desirable to monitor skin deformations. A single sensor can be used at each location. Alternately a multiple of sensors can be used at each location if skin deformations are desired to be measured along plural directions.

A control system 25 is connected by wires to the sensors. The sensors output signals to a computer or microcontroller 26, which in turn modifies the signals for a display unit 30 for visual and/or audible information, or for control purposes. The output of the microcontroller 26 is also applied to a network interface 31 through a data port 28 for transmission to, and reception from, distant stations. Alternately the data can be transmitted directly to a computer or personal digital assistant (PDA) 32 or relayed and received wirelessly through a radio transceiver 34. Data can also be gathered in a non-clinical environment with a small data gathering system while the patient is mobile in an ambulatory mode. The ambulatory system for gathering data is denoted in the dashed box 29, although it may be useful in some instances to add components that are not inside the dashed box, such as a wireless connection. The data gathered can be processed through, and received by, the microcontroller 26 via the two-way communication to the network 31, or computer or PDA 32, or through the radio transceiver 34, or can include an infrared data link, an optical interface, or a microwave link, or a combination thereof.

Figure 2:
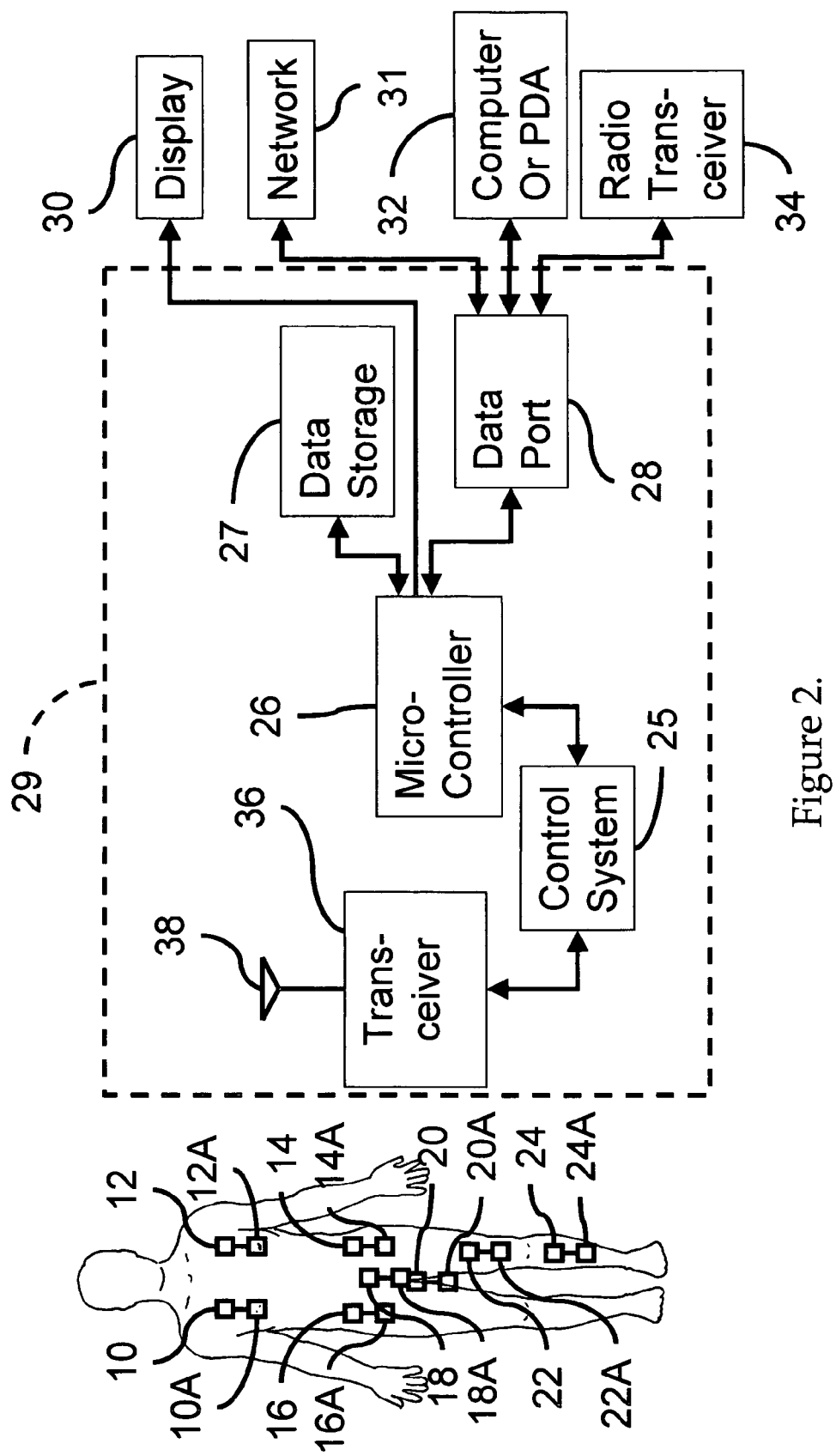
FIG. 2 illustrates the system of FIG. 1 modified for providing a wireless monitoring system.

FIG. 2 is similar to FIG. 1 except that the sensors 10-24 are connected to monitor-radio transceiver circuits 10A-24A for sending signals to, and receiving signals from, a remote transceiver 36 via an antenna 38 eliminating the wire connections of FIG. 1.

Figure 3:
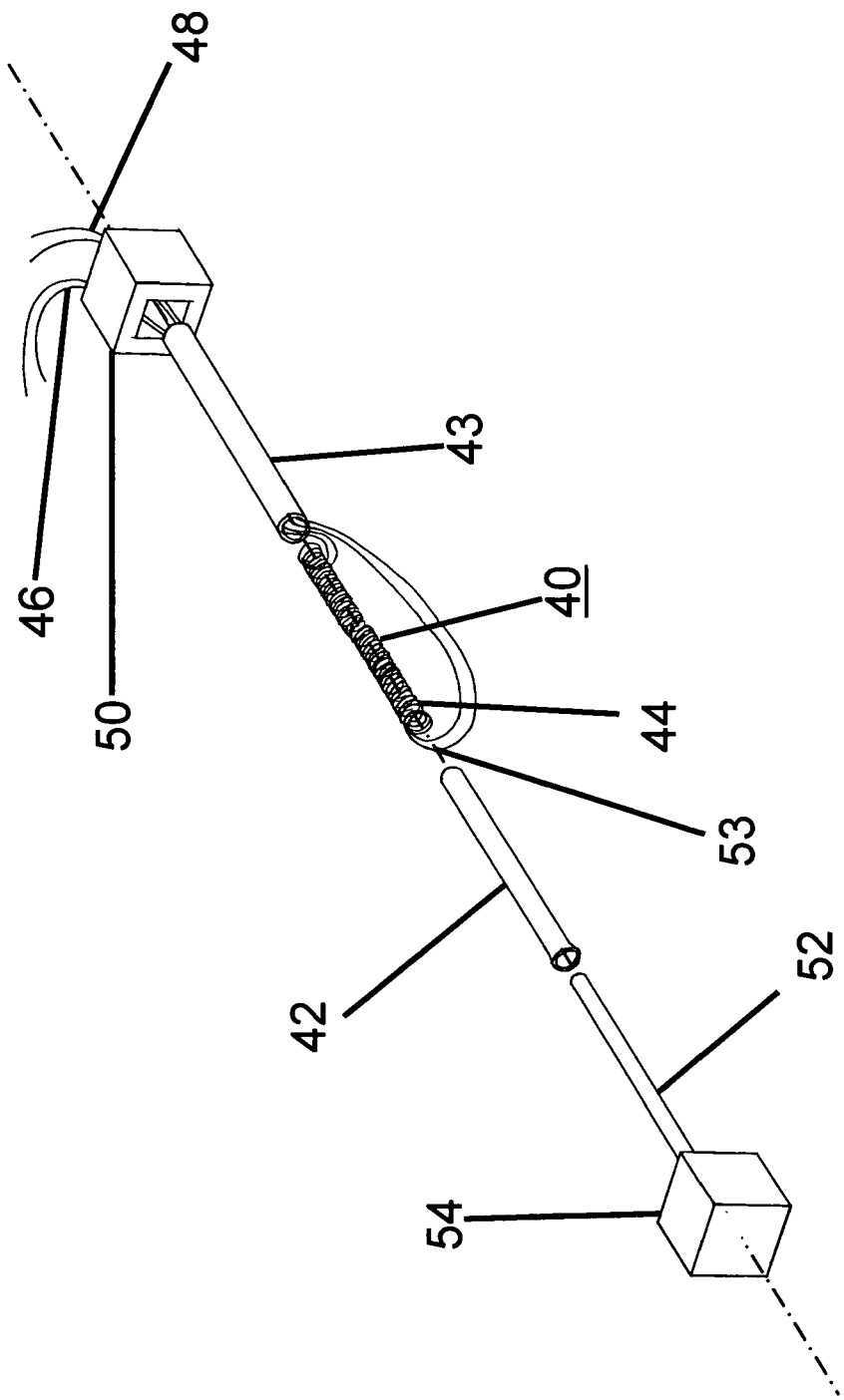
FIG. 3 shows an exploded view of an embodiment of a sensor of the invention.
Figure 4A:
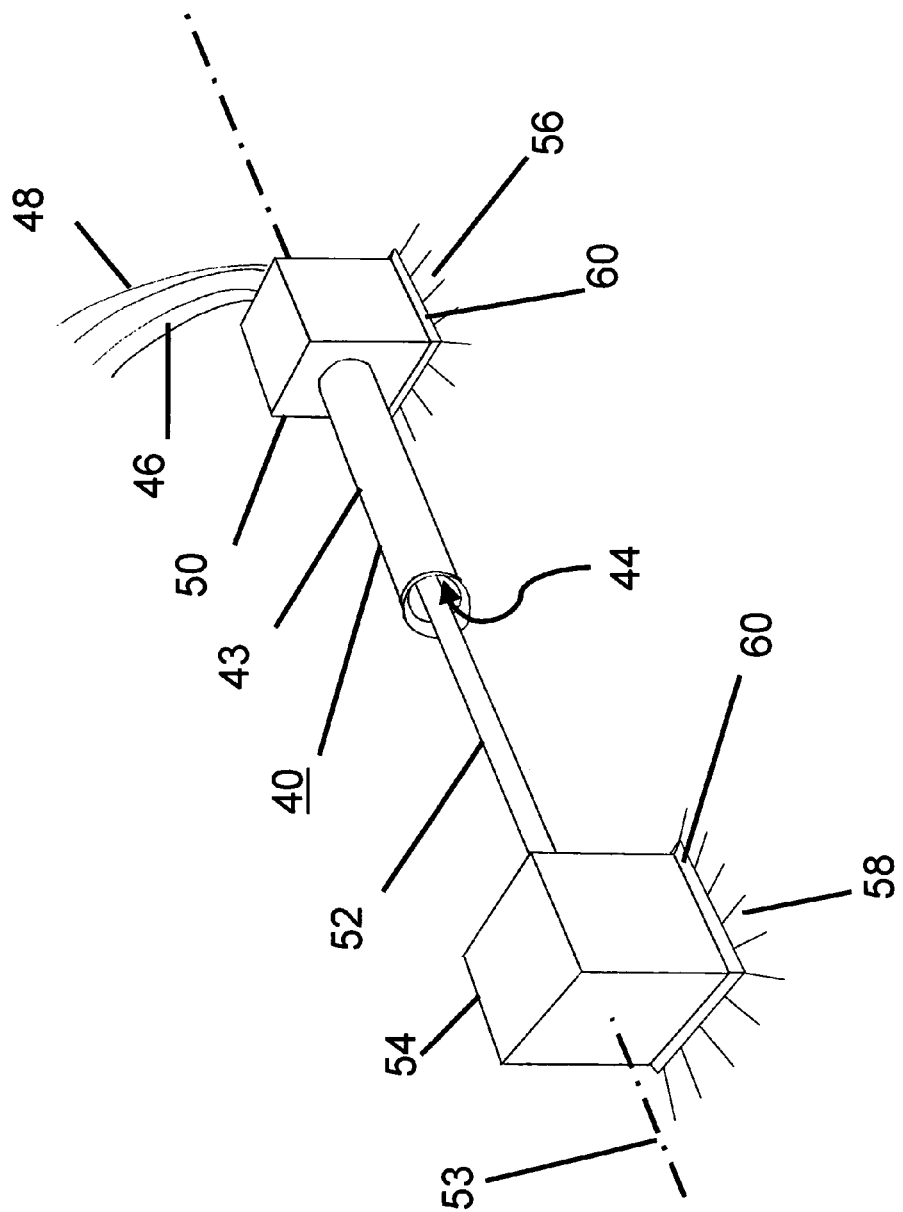
FIG. 4A shows the sensor of FIG. 3 in assembled form.

FIG. 3 illustrates an exploded view of an embodiment of a sensor 40 of the invention, while FIG. 4A shows the sensor assembled. The sensor 40 includes an inner elongated rigid thin tube or bobbin 42 of a non-magnetic material such as brass, stainless steel, or an insulator such as plastic. A coil 44 includes two separate windings (excitation winding 44A and pick up winding 44B of FIG. 10) of a copper wire concentrically wound about the tube 42 having two sets of leads 46 and 48, two for each winding, extending out of an outer tube or shield 43 made of material similar to tube 42. Winding 44A, for the purpose of describing the invention, is designated the input or excitation winding and is adapted to receive electrical signals, while winding 44B is designated as the output or pick up winding that is adapted to output the response of the sensor to the electrical signals, however either winding can function as the excitation winding of pick up winding depending on the sensor design. A mount 50 is attached to one end of the coil 44. Alternately the mount 50 could be attached to the tube 43.

Figure 4B:
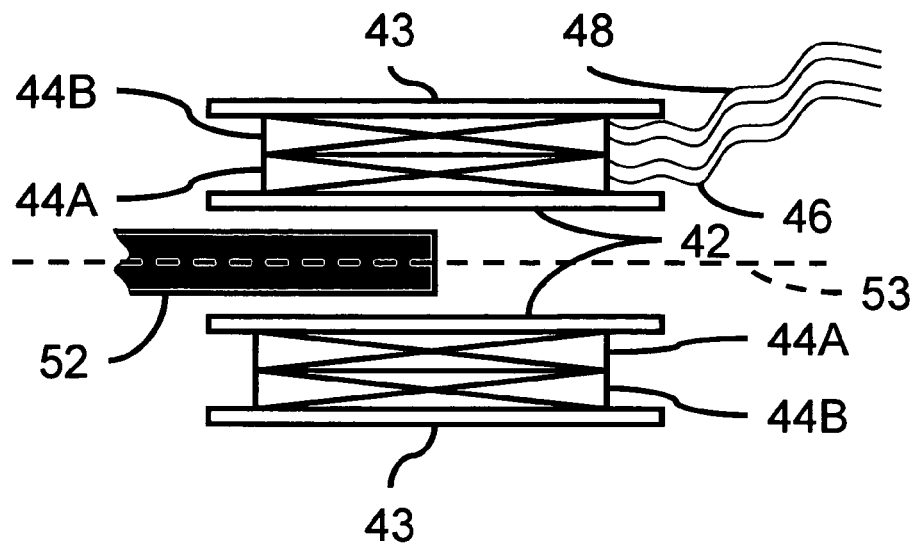
FIG. 4B is a cross sectional view of a portion of the sensor of FIG. 4A illustrating the two winding of the coil one on top the other, and the loose mechanical coupling between the coil and the core.
Figure 4C:
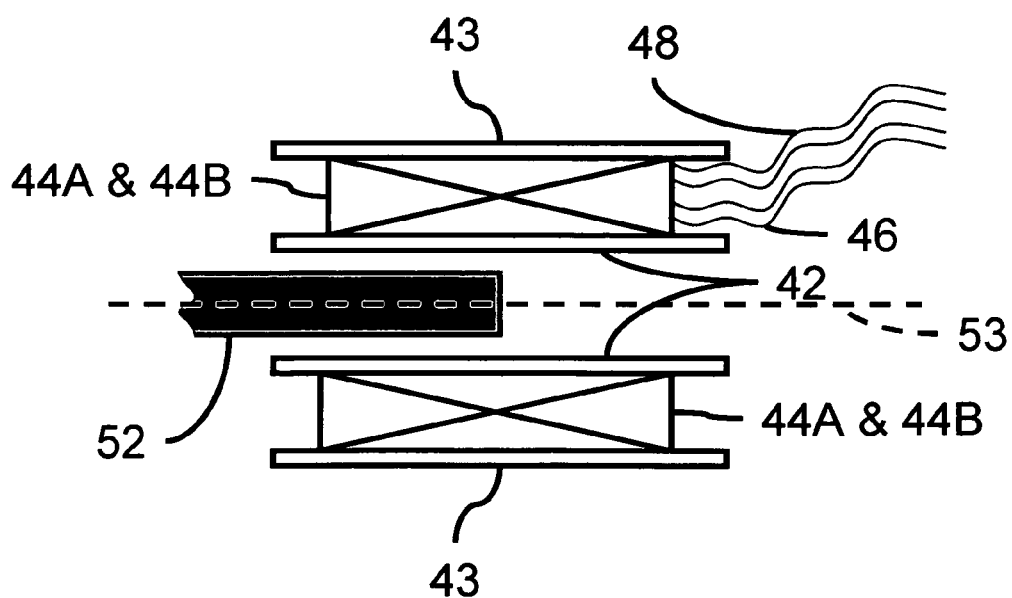
FIG. 4C is a cross sectional view of a portion of the sensor of FIG. 4A illustrating the two windings of the coil wound simultaneously, and the loose mechanical coupling between the coil and the core.

A metallic core or armature 52, preferably a soft (non-permanent) magnetic material is preferable for such as of ferromagnetic or paramagnetic material with low magnetic hysteresis and low eddy currents is adapted to extend within the coil 44 and move along the longitudinal axis 53 of the sensor with approximately equal positioning or displacement within both windings. Although the core 52 is shown as a continuous metallic unit, depending upon the design of the sensor, the metallic core could be attached to an insulating extension rod. A conductor could also serve has the core 52 although increased signal amplification could be required. As illustrated in FIGS. 4B and 4C (not in scale) the core 52 fits loosely within the tube 42 for unhampered free movement in rotation and longitudinally along the axis 53, and to allow for some off-axis parallel and transverse movement of the core (wobble) reducing the need for high tolerance fits between the core 52 and the coil 44 since any movement of the core transverse to, and rotationally about, the axis 53 due to the loose fit does not materially impact the linearity or sensitivity. This freedom of movement allows for ease of assembly and attachment and aids in the unhampered detection by insignificant interference with the deformations of the membrane being measured. The external end of the core 52 includes a mount 54. Although the tubes 42 and 43, coil 44, and core 52 are illustrated having round cylindrical shapes, the various items of the sensor 40 could be formed in different shapes for example, rectangular, and triangular, but matching so as not to disrupt the free longitudinal movement of the core 52. Although the mounts 50 and 54 are illustrated having a square shape, the mounts can be formed of different shapes such as rectangular, triangular or circular and in the case of the core, part of the core can itself be bent to provide a mounting arrangement.

The core 52 becomes the preferred path for magnetic field lines in that part of the coil 44 that the core occupies. FIGS. 4B and 4C illustrate the coil 44 wound about the tube 42 so that windings 44A and 44B are wound about the same tube location so as to achieve approximately the same winding geometry and location. In both FIGS. 4B and 4C the windings are concentrically wound about the tube 42. In FIG. 4B the winding 44B is wound over the winding 44A (although the locations of the windings could be reversed). In FIG. 4C both winding 44A and 44B are intertwined by simultaneously winding the wires about the tube 42.

The mounts 50 and 54 are adapted to be attached to separate movable parts or portions 56 and 58 of an object, as illustrated in FIG. 4, wherein the movements between the portions 56 and 58 are to be monitored. In the case of monitoring skin deformations, the attachment may be made by a medical adhesive 60. The relative displacement between the core 52 and the coil 44 and the changes in inductive reactance exhibited by the sensor 40 changes as the skin deforms. For example, the sensor inductive reactance increases as the core 52 moves deeper within the coil 44. The sensor inductive reactance decreases as the core moves outward. Hence, the inductive reactance of the sensor 40 varies as a function of the relative displacements between core 52 and the coil 44 and therefore as a function of the deformations of the portion of the flexible membrane between mount attachments.

The sensor 40, with its mounts 50 and 54, forms a "bar bell" type configuration that contacts the membrane under test only at the two separated points or portions 56 and 58. Both parts of the sensor 40, the coil 44 and the core 52, are free to move relative to each other. With the sensor 40 attached to the flexible membrane, such as skin, the loose mechanical coupling or fitting of the core 52 within the coil 44 allows the core to freely rotate, and to move within a limited degree parallel and transverse to the axis 53, as the core moves longitudinally along the axis to follow the deformations of the membrane. It has been found with the sensor 40 of the invention that these rotational, parallel, and transverse movements of the core 52 cause insignificant changes in the sensor inductive reactance. This allows the tests to be made along the direction of the longitudinal axis 53 despite that the measured substrate may exhibiting some twisting or movement of a patient under test.

Figure 5:
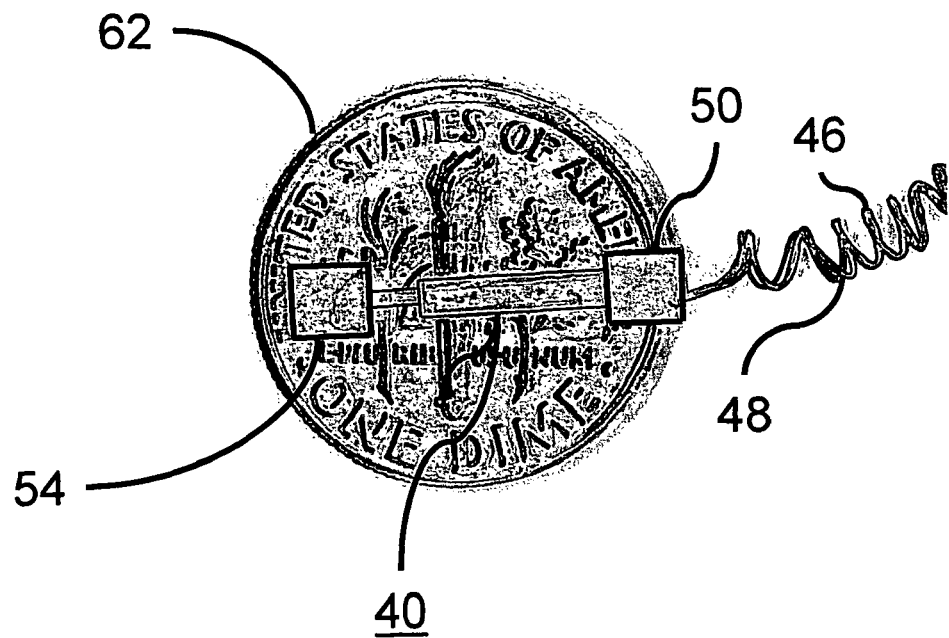
FIG. 5 shows a miniaturized version of the sensor of FIGS. 3 and 4.

In FIG. 5 an embodiment of a miniaturized version of the sensor 40 is compared to a United States dime 62. The sensor windings 44A and 44B are constructed of approximately 100 turns each of a very fine wire such as #40 copper insulated magnetic wire (outside diameter of 0.0035 inches of which 0.0005 inches is insulation), both wound concentrically about the axis 53 of the tube 42 in the same direction (or in opposite directions) with one winding on top the other fitting within the grooves of the other winding as in FIG. 4B, or simultaneously intertwined over a common part of the tube 42. Either winding can serve as the input. The arrangement is such that both windings occupy essentially the same space and geometry toward achieving a unity voltage ratio. The use of the thin wire results in increased parasitic resistance that lowers the sensor Q factor, needed to reduce sensor size and to provide mechanical isolation or decoupling between the measurement electronics and the sensor, but presents insignificant problems. The air core inductance of the sensor is about 2 μHenrys. The tube 42 is of stainless steel 42 mils inside diameter and 50 mils outside diameter. The outer tube 43 is of stainless steel 72 mils inside diameter and 83 mils outside diameter. The space between the coil and the inside of the outer tube 43 is filled with epoxy for mechanical stability. The core 52 is of steel wire on the order of 25 mils in outside diameter (about that of a sewing pin) and which such diameter is approximately 60% of the inside diameter of bobbin 42 thereby providing a very loose fit or mechanical coupling there between. With the loose mechanical coupling as shown in FIGS. 4B and 4C (not in scale), the coil 44 and core 52 are to move freely relative to each other longitudinally and rotationally along the axis 53, and to wobble about the axis with minimal frictional resistance. Depending upon the attachment of the sensor and the object being monitored, the core 52 as it moves within the coil 44 can engage one side to the tube 42 and slide along the tube, or tilt to contact the tube at two positions, or not contact the tube. The core has a relative permeability of about 80 and takes up about 25% of the cross sectional area of the coil 44.

The length of the coil 44 is about 9 mm. In scaling down the size of an inductive sensor, thinner wire and less cross sectional area is employed for the coils, raising their resistances, decreasing their inductances, and significantly decreasing the sensor Q value. However, with the analysis techniques employed by the apparatus of the invention as described below, sensitivity is maintained even for sensors with low inductance and high resistance (and the resulting low Q) such as the exemplary sensor of FIG. 5.

The coil 44 wires extend through spaces in the square opening in the mount 50 and thereafter curl or form bends and preferably extend transverse to the longitudinal movement of the sensor (axis 53). The flexibility of the wires 46 and 48 allows them to flex in directions along, and transverse to, the axis 53, and to flex to accommodate any sensor rotational movements. This arrangement provides a high degree of mechanical isolation or decoupling between the sensor and the measuring apparatus to be connected thereto, reducing the possibility of interfering with the sensor movements.

The mounts 50 and 54 can be for example metal blocks 125 mils cubed. Although the mounts 50 and 54 are illustrated as rigidly secured to the coil 44 and the core 52, if desired a flexible connection can be used to further reduce the likelihood of interference with the deformations of the skin in situations when a curved surface or irregularities are to be monitored. The weight of the sensor so described is approximately 2.5 grams. With the analysis techniques employed by the apparatus of the invention as described below, the sweet spot or the effective scope of sensor linear operation is greater than one half the length of the coil, over which the sensor movement exhibits nearly linear inductive reactance changes. With the sensor of the invention, both the coil and core are free to move unrestrained to follow movements longitudinally and in rotation about the axis 53. Reduced in size, the sensor is particularly adaptable for monitoring skin deformations such as contractions and expansions since the combined mass of the coils, core and mounts, the loose coupling between the core and coil, and the flexibility of the electrical connections imposes an insignificant amount of interference with the deformations in the movement of skin there between, or movements of other types of items being monitored. Any significant amount of interference could otherwise impact the accuracy of the measurements. With the use of the sensor 40 of FIG. 5, the inductance of the coil 44 was increased in the order of tenfold between air core inductance and full core 52 insertion and with the analysis techniques employed by the apparatus of the invention as described below, sensitivity was achieved in the micron range and with relative sensitivity of 100 parts per million with linear operation over more than one half the length of the coil 44.

It should be understood that the size and construction of the sensor 40 of the invention could be tailored to suit its intended use. For example, number of windings of the coils 44A and 44B can be increased or decreased, the ratio of turns between each coil can differ, the coils can be wound in different directions, the size of the wire can changed in general or from winding to winding, and the coils can be wound simultaneously rather than separately. Further, to obtain a further degree of linearity, the windings can be made denser at the ends where the magnetic fields tend to diminish.

Figure 6:
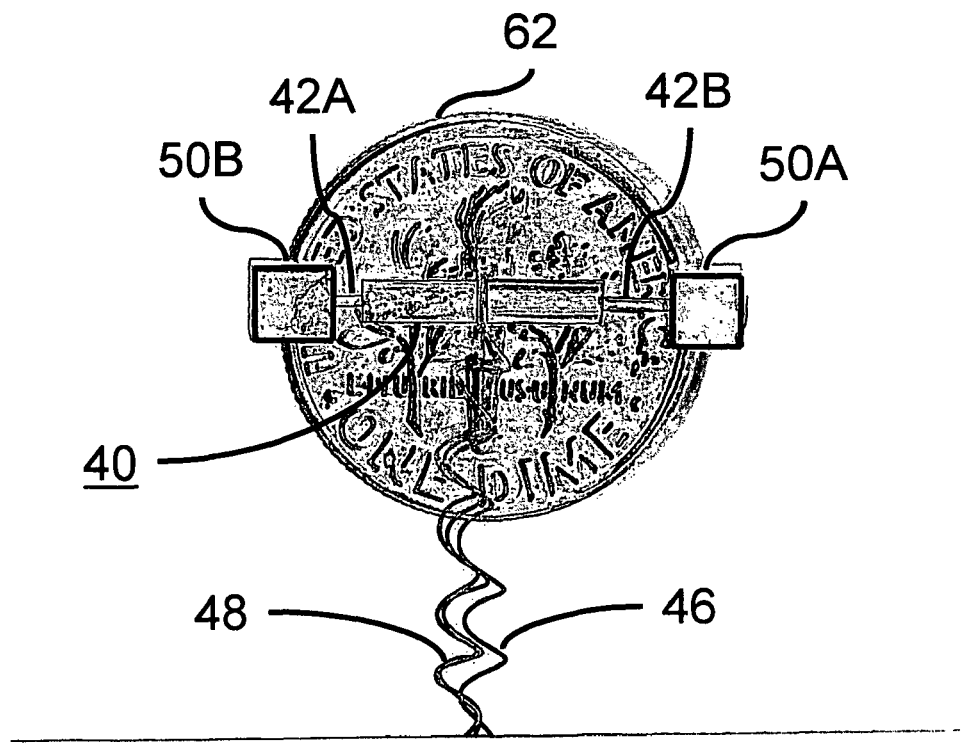
FIG. 6 shows an embodiment of a miniaturized version of the sensor including two cores and a single coil.

In the embodiment of FIG. 6 the miniaturized version of the sensor 40 of the invention, the sensor includes the coil 44 with the flexible electrical connections extending from the center of the coil but do not extend through the gap between the coil 44. Only the cores 42A and 42B include attachment mounts 50A and 50B for providing for the monitoring of two relative moving points.

Figure 7:
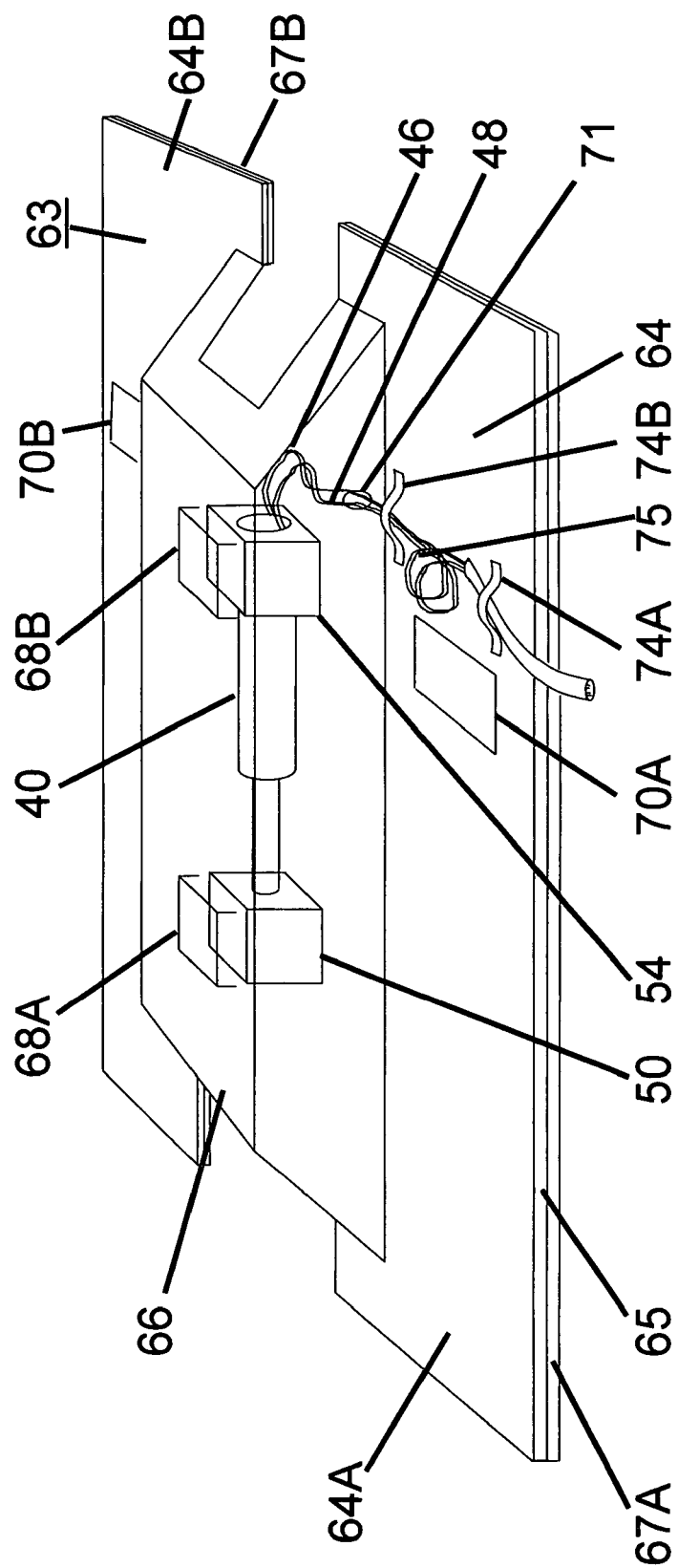
FIG. 7 is a perspective view of the sensor included in a tape type bandage attachment for positioning the sensor on body skin.
Figure 8:
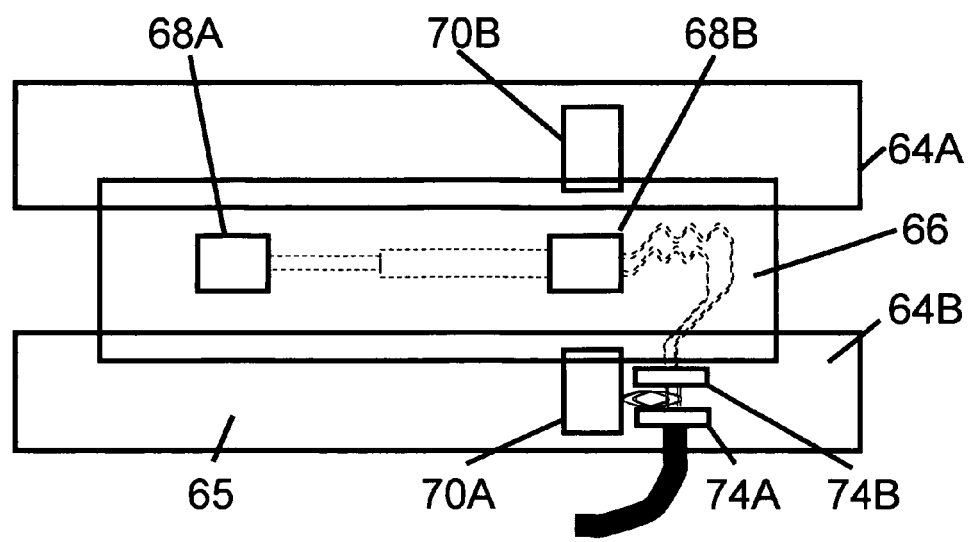
FIG. 8 is a top view of the bandage type sensor attachment of FIG. 7.

FIGS. 7-10 illustrates a "Band-aid" tape type bandage assembly 63 for the sensor 40 for easy attachment to a flexible membrane such as skin. FIG. 7 is a perspective view of the unattached bandage assembly 63 including the sensor 40 positioned within the bandage. The bandage assembly 63 provides an easy means by which the sensor 40 can be attached to the skin as a unit such that monitoring of the skin deformations can be performed while the sensor is protected from outside interference by the bandage. The bandage assembly 63 could be totally enclosed with a plastic or paper enclosure (not shown).

Figure 9:
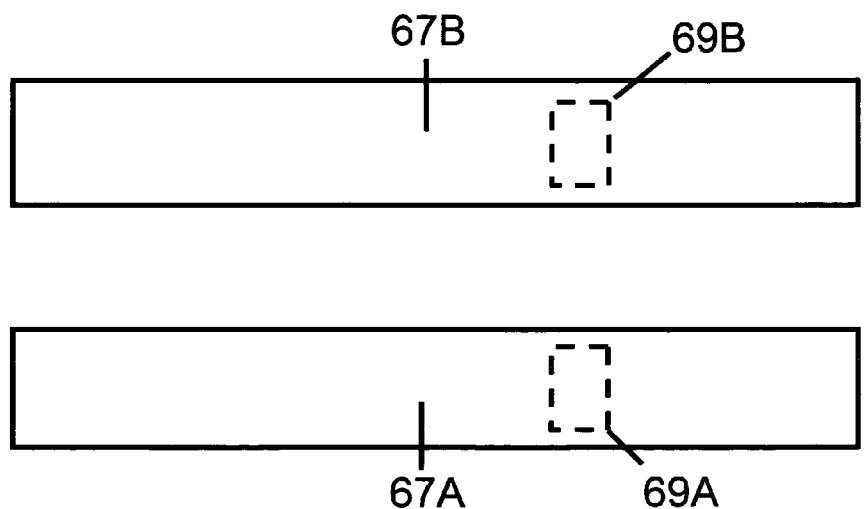
FIG. 9 is a view of bottom layer of the bandage type tape sensor attachment of FIG. 7.
Figure 10:
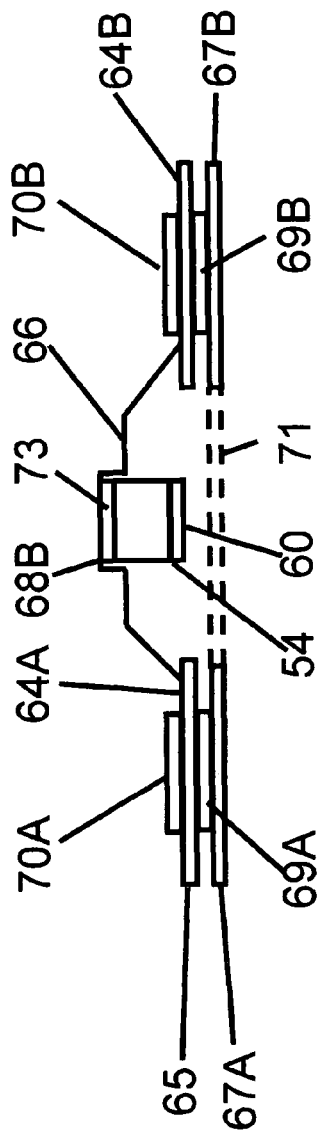
FIG. 10 illustrates a side view of the bandage type sensor attachment of FIG. 7.

The bandage arrangement 63 is comprised of a flexible tape type top layer including two strips 64A and 64B and a resilient thin plastic nodule type projection 66 connection to the two strips and extending away there from. The nodule 66 partially encases the sensor 40. The nodule 66 is preferably of a clear material for viewing the attachment of the sensor to the skin surface and its operation, but it may be opaque. Two caps or projections 68A and 68B are formed in the nodule 66 and extend outwardly there from. The sensor mounts 50 and 54 are loosely captured by resilient forces of the caps 68A and 68B or by a weak adhesive 73 (FIG. 10). The caps of the bandage arrangement keep the sensor core 52 and the coil 44 in preferred registration (approximate midway insertion). The bottom layer comprised of two strips 67A and 67B are attached to the top strips 64A and 64B by glue points 69A and 69B (FIG. 9). The bottom strips 67A and 67B make a weak attachment with the glue points 69A and 69B so that the bottom strips can be readily removed while the glue points remain attached to the top strips 64A and 64B. Although the bottom layer is illustrated as comprised of two strips 67A and 67B, the bottom layer could be a single contiguous layer (as illustrated by the dashed lines 71 in FIG. 10) that is attached to both the top strips 64A and 64B. Further, although the top layer is illustrated as two strips 64A and 64B, the top layer could be a single contiguous layer with an opening therein of a size through which the sensor could extend. The two top strip arrangement with the spacing in between however has a lower likelihood of causing any interference with the deformations of the skin since the top strips 64A and 64B extend along the bandage on opposite sides of the sensor 40 and parallel to the direction of movement of the sensor. The exterior sides of the top strips 64A and 64B also include the touch points 70A and 70B respectively for finger pressure during bandage attachment.

The bandage type sensor arrangement is applied to skin by first removing the bottom strips 67A and 67B, and then set in place by pressing on the touch points 70A and 70B to become attached to the skin by the glue points 69A and 69B. The caps 68A and 68B are pushed down causing the nodule 66 to flex so that the bottom of the mounts 50 and 54 engage the skin and adhere thereto by the adhesive 60 (FIG. 10), which can be included as part of the bandage arrangement or applied to the mounts just before attachment to the skin. When pressure is removed, the caps 68A and 68B spring back and release the mounts 50 and 54 while the sensor remains secured to the skin.

The curled sensor wires 46 and 48 extend through an opening 71 in the nodule 66 in a direction transverse to the sensor longitudinal axis, curl or wind through a loose clamp 74B to form a loop 75, and are held in place by a tight clamp 74A from which they extend from the bandage mounting. Such arrangement provides for an effective mechanical isolation or decoupling of the sensor from the system control circuit 25 (FIG. 1) so as to avoid mechanical forces from being exerted on the sensor that might interfere with the skin under test.

Hence as can be seen, the bandage type sensor mounting arrangement of the invention can be easily placed on the skin and the sensor attached to the skin with the sensor in its preferred registration (approximately midway rod insertion). A nurse or technician can simply remove the bottom strips 67A and 67B, place the bandage arrangement over the portion of the skin in the direction to be monitored, push on the touch points 70A and 70B to secure the bandage arrangement to the skin by the adhesive layers 69A and 69B, and push down on the caps 68A and 68B and release them as the sensor mounts 50 and 54 adhere to the skin. Connections can be made to the control system 25 via the flexible wires 46 and 48 without disrupting the sensor attachment or without creating any mechanical interference that might otherwise impact the operation of the sensor. With the glue points 69A and 69B located opposite only one mount 54, the glue points, as they hold the bandage arrangement in place, will not interfere with the contraction and expansion of the skin being monitored.

Figure 11:
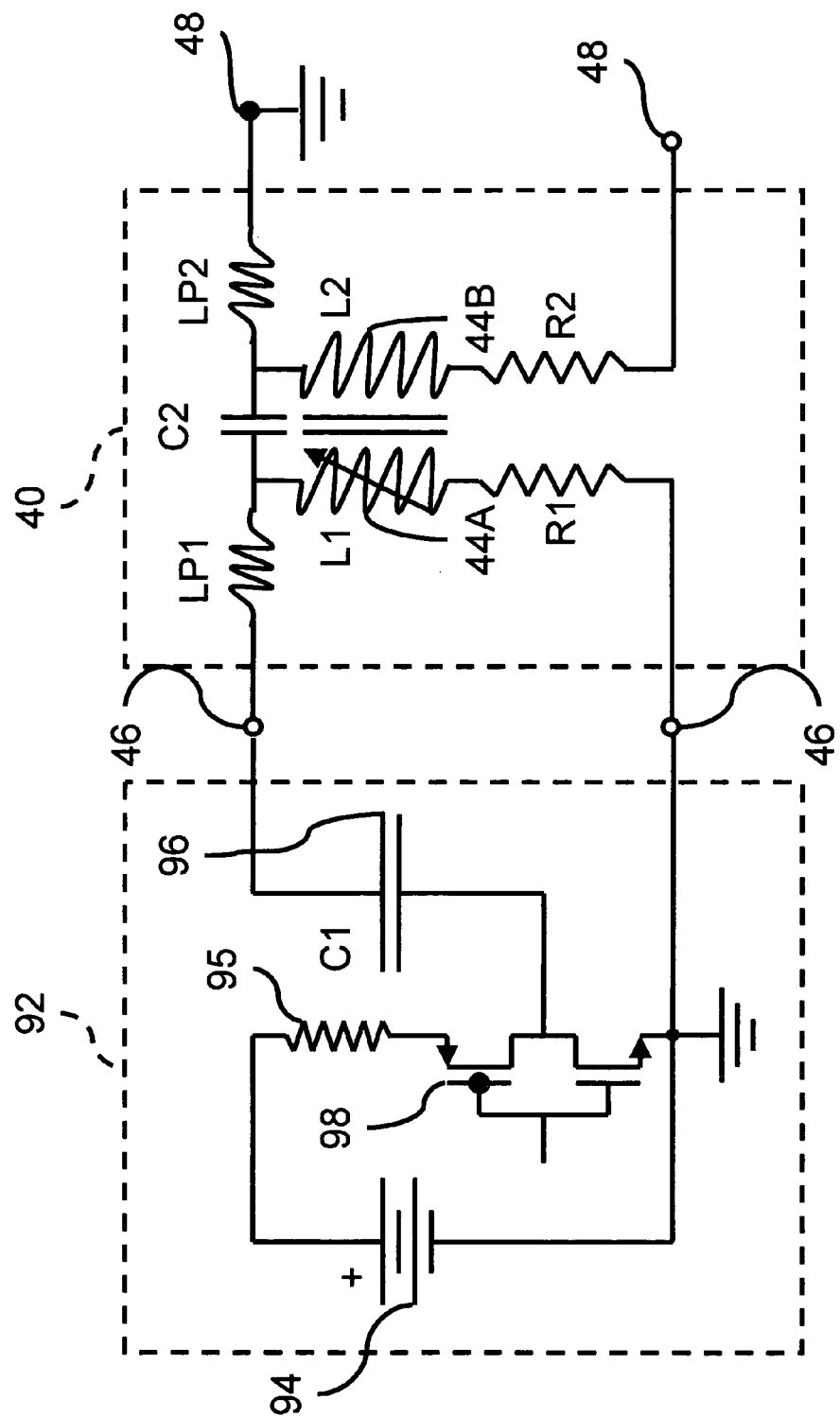
FIG. 11 is an electrical schematic drawing of the sensor of FIGS. 3 and 4 and a circuit for applying pulses to the sensor.

FIG. 11 is a schematic diagram of the sensor circuit of FIGS. 3 and 4 in accordance with one embodiment of invention in which the sensor is driven by a pulse type generator 92. Circuit 92 is illustrated as an electrical equivalent circuit, including a power source illustrated as a battery 94, a capacitor 96, and a switching semiconductor 98 such as a power CMOS inverter (although other semiconductor circuit designs could be used). Capacitor 96, designated C1, has a value in the order of 4.7 microfarads. The windings 44A and 44B have been designated L1 and L2 for mathematical analysis purposes. The intrinsic resistances of the windings 44A and 44B are designated R1 and R2 for mathematical purposes. The windings 44A and 44B have a parasitic capacitance C2 and parasitic inductances LP1 and LP2.

Figure 12:
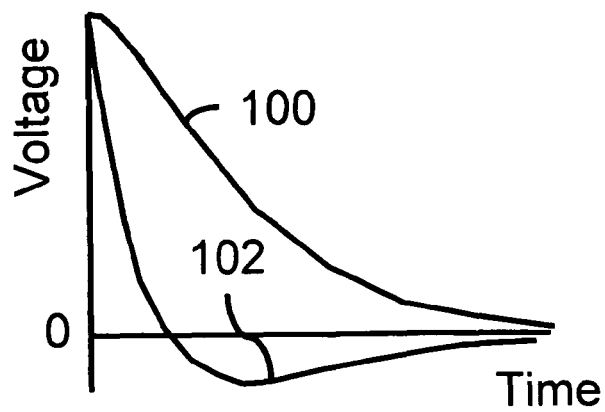
FIG. 12 illustrates voltage versus time curves across the input and output of the sensor schematic of FIG. 11 in response to the application of a pulse.
Figure 13:
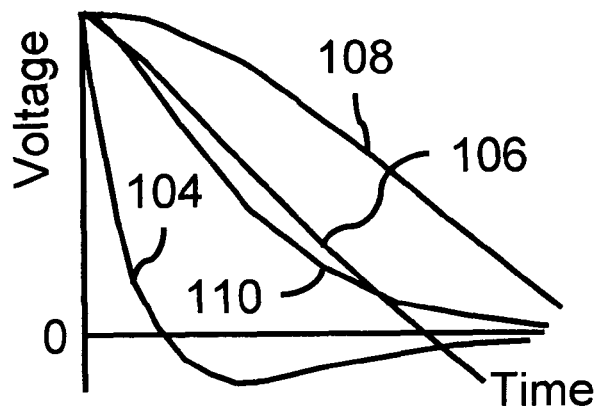
FIG. 13 illustrates voltage versus time curves of input and output responses of the sensor of FIG. 11 to the pulses with two different displacements of the sensor.
Figure 14:
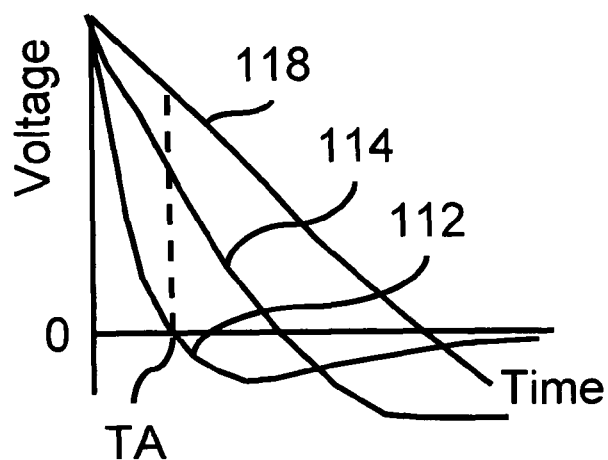
FIG. 14 illustrates voltage versus time curves of the output of the sensor of FIG. 11 to pulses for three different displacements of the sensor.

When semiconductor 98 is switched into its charging condition, the capacitor 96 is charged to the voltage value of the battery 94 (3.3 volts) through the winding 44A and the resistor 95 having a value of 1 Kohm so that the capacitor's charge time constant is about 4.7 milliseconds. When the semiconductor 98 is switched to the discharge condition, the charge across the capacitor 96 is discharged via the sensor leads 46 through the input winding 44A and the sensor outputs a decaying type of response from the pick up winding 44B across leads 48 as illustrated in FIGS. 12-14. The discharge time through the sensor 40 of the miniaturized type described with regard to FIG. 5 is in the order of 10 microseconds, depending upon the various reactive impedances and resistances exhibited by the sensor. When the capacitor 96 is subsequently recharged, the current through the winding 44A is reversed advantageously through resistor 95 eliminating some magnetic hysteresis created in the core 42, through slow charging of the capacitor 96. It should be understood that other switching arrangements can be used in which the capacitor 96 is not recharged through the winding 44A. The power consumption of the sensor per capacitor 96 charge and discharge is very low, estimated to be in the order of 5×10$^{-5}$ Joules, greatly reducing the power supply demands for portability. The series resistance of the capacitor 96 is on the order of 0.003 ohms, which is designed to not materially impact the discharge of the circuit.

The voltage at the output leads or nodes 48 is the voltage essentially across the inductor L2 due to the induced voltage across L1. When the pick up winding 44B is connected to a high impedance circuit, C2 and R2 have negligible effect on the circuit. In the extreme of (R1 C1) small compared with (L1 C1)$^{-1/2}$ the current is sinusoidal and the voltage observed on output leads or nodes 48 is sinusoidal with a frequency proportional to (L1 C1)$^{-1/2}$. In other regions of operation, the behavior is more complex, but in all cases the resultant output voltage at output leads or nodes 48 has at least one zero-crossing point, or polarity change, which is advantageously used in the design of the control circuit 25. For example, the voltage can be sampled just prior to the zero crossing point in order to get a sensitive measure of any changes in the inductive reactance of the coil. Further, the zero crossing point is independent of the magnitude of the excitation pulse voltage applied to winding 44A and the time for zero crossing is a deterministic function of R, L, and C.

For a sufficiently small value of LP1, the active sensor circuit of FIG. 11 for mathematical analysis can be simplified as a series RLC circuit consisting of R1, L1 and C1 since the passive coupling to the output winding 44A is negated by the use of a high impedance across leads 48. With equal turns in windings 44A and 44B, when the capacitor 96 is discharged, the induced voltage across inductor L2 is generally equal to the voltage across L1, and by the use of a high impedance across leads 48 the voltage across leads 48 is close to the voltage across inductor L1 (unity induced voltage ratio), since the voltage drop across R2, C2 and LP2 are negligible.

The treatment of series RLC circuits is well known in the literature, and consists of three regions depending on the ratio of (RC)$^2$ to 4LC. There are three regions including over-damped, critically damped, and under-damped. The over-damped and under-damped regions are separated by a critically damped point where (RC)$^2$ is equal to 4LC. An increase in the inductance from the critically damped point causes the circuit to become under-damped, and a decrease in the inductance from the critically damped point causes the circuit to become over-damped. Ideally in all cases the voltage across the inductor L1 initially is at the power source voltage, and since the initial current is zero the voltage drop across the resistor R1 is therefore zero.

If the circuit consisting of R1, L1, and C1 is very under-damped, then the voltage differential at nodes 46 substantially equals the voltage differential at nodes 48, and the time at which both voltages cross zero after the discharge of capacitor C1 is:

$$t_{V_L=0} = \frac{2LC}{\sqrt{4LC - R^2C^2}} \left[ \mathrm{atan}\left(\frac{\frac{2L}{R} - RC}{\sqrt{4LC - R^2C^2}}\right) + \mathrm{atan}\left(\frac{RC}{\sqrt{4LC - R^2C^2}}\right) \right]$$

$$t_{0U} \cong \pi/2 * \sqrt{LC}$$

In the case that the circuit consisting of R1, L1, and C1 is critically damped, the voltage across nodes 46 decays to zero but does not changes sign, while the voltage across inductor L1 (and that essentially across nodes 48) is:

$$V_L = V_0\left(1 - \frac{t}{\sqrt{LC}}\right)\exp\left(-\frac{2t}{RC}\right)$$

and crosses zero at a time:

$$t_{0C} = \sqrt{LC}$$

In the heavily over-damped case there is relatively little response across nodes 46 to inductive changes, as the circuit is dominated by an RC decay. However, the voltage across nodes 48 is very dependent on the inductance. Again the voltage differential at nodes 46 does not change sign while the voltage at nodes 48 crosses zero at a time:

$$t_{V_L=0} = \frac{LC}{\sqrt{R^2C^2 - 4LC}} \ln\left[\frac{RC + \sqrt{R^2C^2 - 4LC}}{RC - \sqrt{R^2C^2 - 4LC}}\right]$$

$$t_{0O} \cong L/R * \ln(R^2C/L)$$

The inductive sensor of the invention is not transformer sensitive in that the ratio of the voltages between the input excitation winding 44A and the output pick up winding 44B is based on the ratio of the number of turns in the windings and does not materially change with changes in the relative dispositions of the coil 44 and the core 42.

The relative sensitivity of the sensor can be examined by differentiating the equations for the time dependence of the voltage with respect to the inductance. While a general solution is tedious, the over damped, critically damped, and under damped regions will be discussed. The fractional change in detected voltage for an inductance change relative to the current inductance value is the sensitivity. For the extremely over damped region, the maximum sensitivity is:

$$\frac{dV}{V_0} = \frac{dL}{L}e^{-1} = 0.37\frac{dL}{L}$$

and occurs at a time after the discharge of the capacitor:

$$t = \frac{L}{R}$$

When the system is critically damped the maximum sensitivity is, $$\frac{dV}{V_0} = 0.39 \frac{dL}{L}$$

and occurs at a time after the discharge of the capacitor $$t = \frac{L}{R} = \frac{\sqrt{LC}}{2}$$

When the system is extremely under damped, the sensitivity at the first maximum in sensitivity is:

$$\frac{dV}{V_0} = 0.91 \frac{dL}{L}$$

and occurs at a time after the discharge of the capacitor:

$t \cong 2\sqrt{LC}$

It should be noted that these are the sensitivities without amplification and with a unity voltage coupling ratio on the coils. This sensitivity of the sensor is quite high and essentially independent of resistance (or Q). Hence, with the Q insensitive sensor as described herein, the size of the sensor can be designed to fit a wide variety of monitoring purposes without facing Q restrictions. This is particularly important when the sensor is scaled in size for miniaturization with the use of smaller sized wires without significant limitations caused by the intrinsic resistance of the wire that would otherwise impact the efficiency of the sensor.

The FIGS. 12-14 are general representations of the decaying sensor responses for typical traces resulting from the application of an input pulse from the capacitor 96 to the sensor 40. For simplifying the description of the sensor, the following explanations will be directed to critically damped or over damped sensors, however it should be understood that will also apply to under damped sensors except that in such case both windings 44A and 44B will exhibit zero crossing points. As seen, with a unity sensor voltage ratio (due to equal turns in the windings 44A and 44B), the magnitudes of the initial voltages at the input leads 46 and output leads 48 are about the same. In FIG. 12 the curve 100 is the voltage across the input leads 46, and the curve 102 is the resulting voltage across the output leads 48. With a critically-damped or over-damped arrangement of the resistance, capacitance and inductance of the sensor circuit the curve 100 does not have a zero crossing (polarity change). The voltage across the output leads 48 (curve 102) decays at a greater rate as compared to the voltage across the leads 46 (curve 100) and the curve 102 has a zero crossing point that is used to provide a well defined function of sensor inductance over the entire range of inductance L. A method can be used to ascertain the approximate zero crossing time by taking one or more measurements with fixed coil impedance. For subsequent measurement pulses, the voltage can be measured at set time near the previously ascertained zero crossing point. With this method, a voltage can be measured that is sensitive to subsequent small changes in inductance, particularly with the use of signal amplification. Further it is asserted that the choice of a time slightly prior to the zero crossing point, such that the initial monitored voltage is 10 to 20% of the supply voltage, will give a nearly linear voltage response to small inductance changes.

Therefore the measurement based on the pickup winding 44B can be used across a wide range of inductance of the sensor. Even when the circuit is over-damped (low Q) and there is limited response across nodes 46, while the voltage and zero crossover timing across nodes 48 provide a strong indication of the inductance. Further, it is practical to develop a time based measurement algorithm, or a voltage based measurement algorithm, of an algorithm that is a combination of both, as for example finding a zero crossing time as a gross indication of the inductance, and measuring subsequent changes in voltage at or near that time for a sensitive indication of inductance changes.

FIG. 13 shows various sensor responses exhibited by the sensor 40 of FIG. 5 at the input and output leads 46 and 48 over an order of magnitude of sensor impedance change due to displacements of the core 52 relative to the coil 44. The curves 108 and 110 represent sensor input voltages across leads 46 and the curves 104 and 106 represent voltages across the output leads 48. The curves 104 and 110 are characteristic of lower sensor inductance, and curves 106 and 109 are characteristic of an order of magnitude increase in sensor inductance. The curves 104 and 110 correspond to the air core inductance of the sensor, and the curves 106 and 108 correspond to the core 52 fully inserted into the coil 44. Both curves 104 and 106 have zero crossings while curves 108 and 110 do not.

The FIG. 14 shows the voltage across the output leads 48 for three different values of inductance of the sensor 40. The curve 112 corresponds to the core 52 approximately 20% inserted into the coil 44, the curve 114 corresponds to the core approximately 50% inserted into the coil, and the curve 118 corresponds to the approximately core 80% inserted into the coil. All three curves exhibit zero crossings. By sampling the voltage at an appropriate time near the zero crossing, such as at time TA after the application of the pulse to the sensor, a fairly monotonically varying output signal can be obtained proportional to relative dispositions between the core 52 and the coil 44 as the output of the sensor varies between curves 112 and 118.

FIG. 15 discloses a basic block diagram of an apparatus of the invention for monitoring the inductive reactance changes of the sensor 160 in response to the deformations of items being monitored. Further, for ease of explanation, similar items in the following Figures, where practical, will have the same reference numbers. A pulse generator 159 applies electrical signals to the sensor 160. A monitor circuit 162 identifies the changes in the inductance of the sensor 160 and provides digital signals to a microcontroller 164, which in turn analyzes the digital signals and provides an output indicative of the movements monitored to a computer 174, such as a lap top computer, through an interface 165 which translates signal and/or timing between that required by the computer and that used by the microcontroller. The computer 174 provides the human interface as a control means for the operation and read out of the monitoring system, stores data in long term memory, and translates the data for control, visual and/or audible indications from the display 166 and provides programming of the microcontroller 164.

For portable or ambulatory use, the monitoring circuit 162 and the microcontroller 164 are powered by a power source using two 3.3 volts watch type batteries connected in series. The resulting 6.6 volt node is connected through a standard DC regulator circuit to maintain a constant 3.3V output. Two large capacitors (100 µF) are included in the power circuit, one between the 6.6 volt node and ground and the other between the 3.3V regulator output and ground for supplying high currents for short periods of time, such as could be needed, for example, to write data to the FLASH data storage. The regulator is gated so it does not supply power when hooked up to an exterior 3.3 volt source, such as supplied by the computer 174. To reduce the drain on the batteries, a separate timing arrangement is used to allow the monitoring circuit 162 and the microcontroller 164 to switch to a "sleep" mode of operation between data acquisition sets as described below. On the other hand if portability is not important, then a fast transient response power supply having a capacitive output could be used. Further, it is preferred if the output impedance of the power supply is lower than the impedance of the sensor, otherwise the impedance of the power supply would add to the sensor impedance resulting in a lower delay time. It is also preferred if the inductance of the power supply be negligible with respect to the inductance of the sensor so that the power supply does not exhibit a voltage drop when applying a pulse to the sensor.

With a miniaturized embodiment of the sensor of FIG. 5 and with a bounded scope of displacements due to skin deformations, the monitor circuit 162 includes signal amplification (such as 5-100×) to achieve the degree of sensitivity desired. As a result the amplification circuits may at times be driven into saturation or below zero volts (high or low saturation) limiting the range of the system operation. The system of FIG. 15, as described above, depending on system sensitivity, will still at times require a fairly accurate manual pre-setting of the sensor near its midpoint and/or the manual adjustment of the system parameters.

A further feature of the invention includes the use of a control circuit 168 (illustrated as connected by a dashed lines in FIG. 15) for automatically adjusting the monitor circuit 162 timing and sensitivity parameters to fit within the scope of sensor impedance changes. Although the control circuit 168, the microcontroller 164, interface 165, computer 174 and the display unit 166 are illustrated as separate blocks for purposes of ease of explanation, portions of these blocks can functionally be included in the microcontroller 164 or the computer 174 and operate by use of software programs.

FIG. 16 is a modification of the block diagram of FIG. 15 for use with the remote monitoring arrangements of FIG. 2. The monitor circuit 162, the microcontroller 164, and the control circuit 168 are packaged with a transceiver 170 so as to be adapted to be attached to the body near the sensor 160. The transceiver circuit 172 converts the received output of the transceiver 170 into digital form for use by the computer 174 for outputting the monitored results to the display unit 166. The transceiver 172 also transmits data to the transceiver 170.

Figure 17:
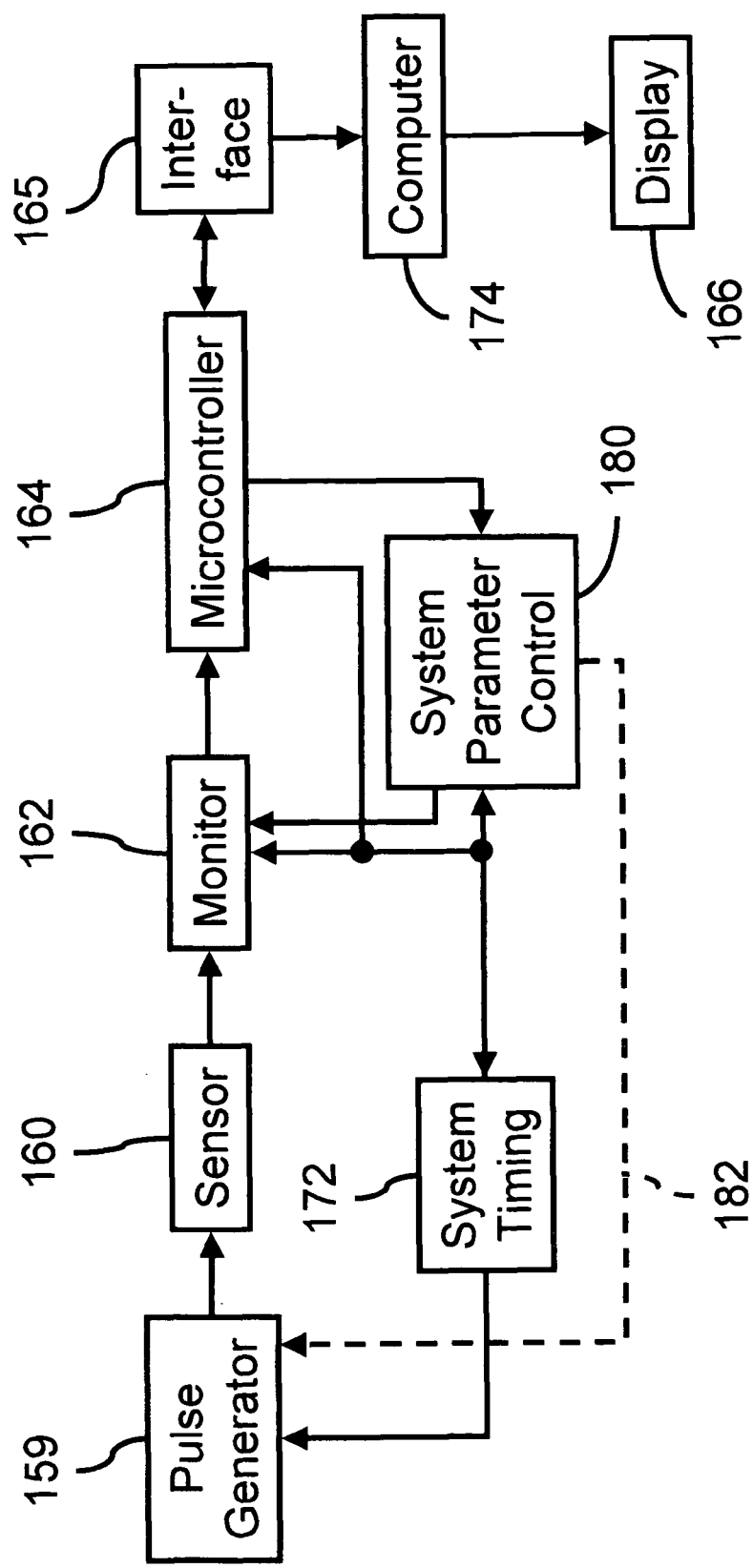
FIG. 17 is an expanded block diagram of the system of FIG. 15.

In the expanded block diagram of FIG. 17 the pulse generator 159 periodically applies pulses to the sensor 160 at a rate controlled by a system timing circuit 172 that includes a low frequency timer for accurately initiating a test for data acquisition set at a programmable period typically between 2 seconds and 1/32 of a second, and a high frequency clock for use during the data acquisition functions. A decaying type of response from the sensor 160 is detected by the monitor circuit 162, is digitized and provides two digital data outputs to the microcontroller 164, one in the form of a rough or gross, and the other a fine or definitive, indications of sensor displacements. The microcontroller in turn analyzes the data and outputs information via the interface 165 to the computer 174 to the display unit 166. The microcontroller 164 includes a microprocessor with typical supporting components such as communications and programming interfaces, control registers, data and code storage as FLASH and RAM memories, and clock and timing generation and is programmed by codes written, compiled and downloaded from the computer 174 via a commercial ATMEL board as the interface circuit 165, to perform the functions as described below. The control circuit includes a system parameter control circuit 180, also synchronized by the high frequency clock of the system timing circuit 172, that is responsive to an output from the microcontroller 164 to adjust the timing between the analysis of the monitor circuit 162 and the application of pulses to the sensor 160 for conditioning the system timing parameters for midrange operation. Alternately, the pulse generator 159 timing can be changed as illustrated by the dashed line 182, or both the timing of the monitor circuit 162 and the pulse generator 159 can be changed. The system parameter control circuit 180 can also be used to adjust the sensitivity of the system by adjusting gain. Although the system parameter control 180 is illustrated as a separate block for explanation purposes, it should be understood that the system parameter control 180 functions could be included in and performed by software in the microcontroller 164.

Figure 18:
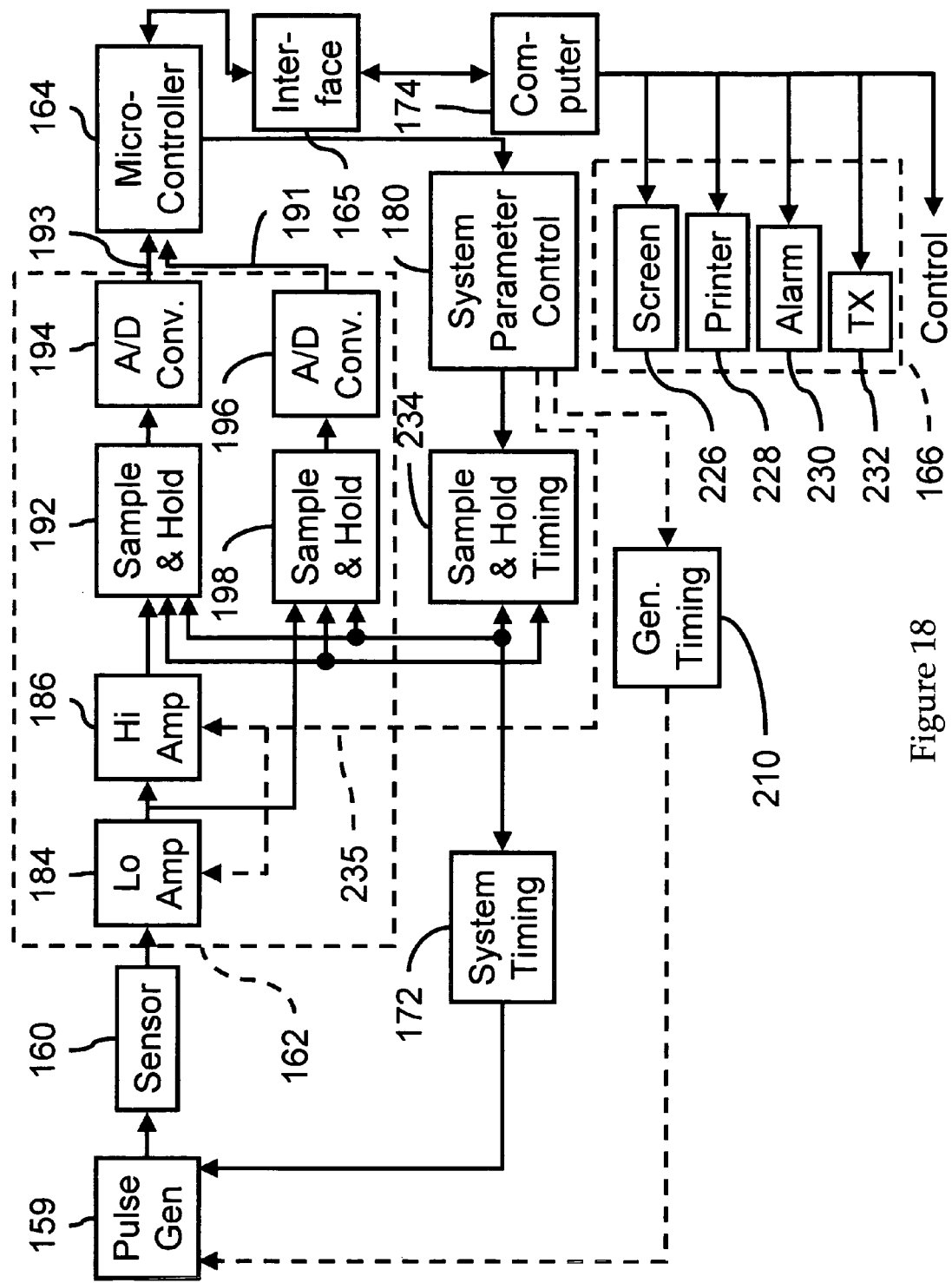
FIG. 18 is a more detailed block diagram of the system of FIG. 17.

The monitor circuit 162 is shown within the dashed block in FIG. 18. The monitor circuit includes a low gain amplifier 184 driving a high gain amplifier 186, the outputs of each are applied to separate analog memory circuits such as for example sample and hold circuits 198 and 192, respectively. The high and low gain amplifiers have inputs for placing the amplifier circuits in a standby low power mode of operation when the system is put in a power savings sleep mode of operation as described below. The low gain amplifier 184, or the high gain amplifier 186, or both amplifiers, can have a variable gain feedback loop, manually or electronically operable, for adjusting the system sensitivity parameters. The outputs of the sample and hold circuits 192 and 198 are applied to separate A/D converter circuits 194 and 196 respectively, each of which outputs digital signals to the microcontroller 164 via the low gain data line 191 and via the high gain data line 193. The circuits are preferably CMOS with inputs set high or low during periods of inactivity so as not to draw a significant amount of current. The microcontroller analyzes the digital signals and sends an output indicative of sensor displacement to the computer 174 for outputting to the display unit 166, including items such as a screen 226, printer 228, alarm 230 and transceiver 232 or outputting a control signal. The timing of the data acquisition functions of the monitor circuit 162 and that of the microcontroller 164 are controlled by the high frequency clock.

The microcontroller 164 also performs a binary analysis of the digital signals to determine if the timing between the application of the pulse and the latching of the sample and hold circuits 192 and 198 falls within system midrange operation, and if needed, changes the timing of the sample and hold timing circuit 234 via the system parameter control circuit 180 until an approximate operation is reached within system midrange. Alternately, the system parameter control circuit 180 can control the timing of the pulse generator 159 via the timing control circuit 210, or both the timing of the pulse generator 159 and that of the sample and hold circuits 192 and 198.

Either the low and high gain amplifiers 184 and 186, or both, may be adjusted to control the sensitivity of the system by the system parameter control circuit 180 via the dashed connection 235.

The low gain output 191 is used to provide a gross indication of the absolute displacement, while the high gain output 193 provides the high sensitivity output of the relative displacements, and in particular changes in the relative displacements with time. The relative displacement is important to infer changes in the larger system. For example, if the relative displacement of the sensor indicated a change of 1%, and the sensor attach points 56 and 58 are one inch apart, then this would infer a change in circumference of 0.4 inches about a body circumference of 40 inches, assuming uniform contraction and expansion.

Figure 19:
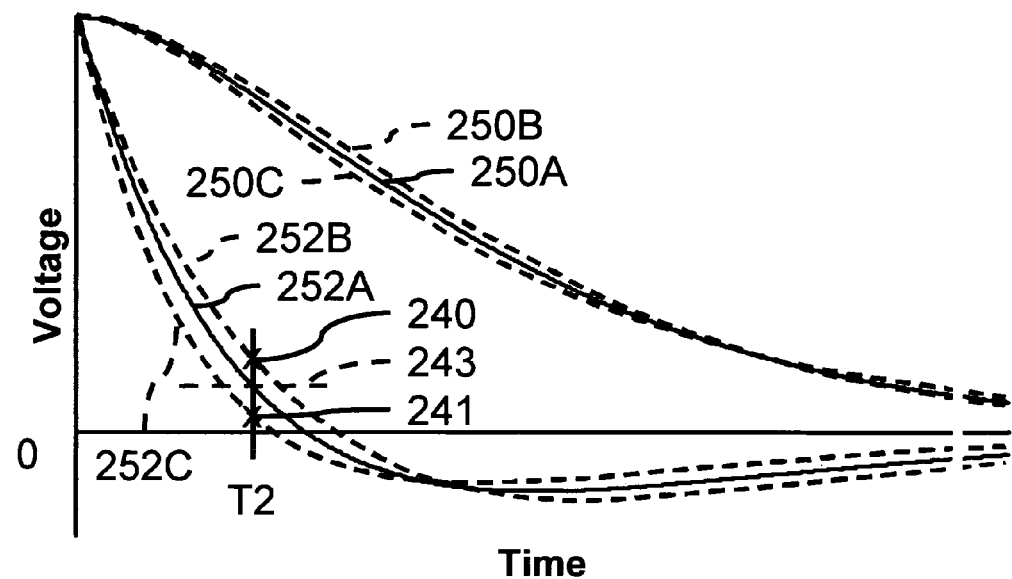
FIG. 19 includes curves illustrating input and output responses of the sensor to trigger pulses with different sensor displacements.

The operation of the monitor circuit 162 is further explained with reference to FIGS. 19 and 20 in which the sensor 160 is critically damped or over damped. In FIG. 19 the curves 250C and 252C show the voltage across terminals 46 and 48 respectively when the core 52 is partially inserted into the coil 44, while the curves 250A and 250B and 252A and 252B represent the voltage across terminals 46 and 48 respectively with increasing core insertions. The curves 252A, 252B and 252 have zero volt crossing points while the curves 250A, 250B and 250C do not. However if an under damping arrangement is used all curves will have zero crossings.

With regard to sensor linearity and sensitivity, it is preferred that the monitoring circuit of the invention monitors the output of the sensor relative to time T2 adjacent to the zero cross over point within a range of sensor outputs between 10% to 30% of the scope of curves 252A, 252B and 252C. As illustrated in FIG. 19, the midpoint of system operation is designated by level 243, while levels 241 and 240 represent the 10% and 30% points respectively. However it should be understood that the monitoring system can operate over a larger range of levels to cover a larger scope of sensor movements.

Figure 20:
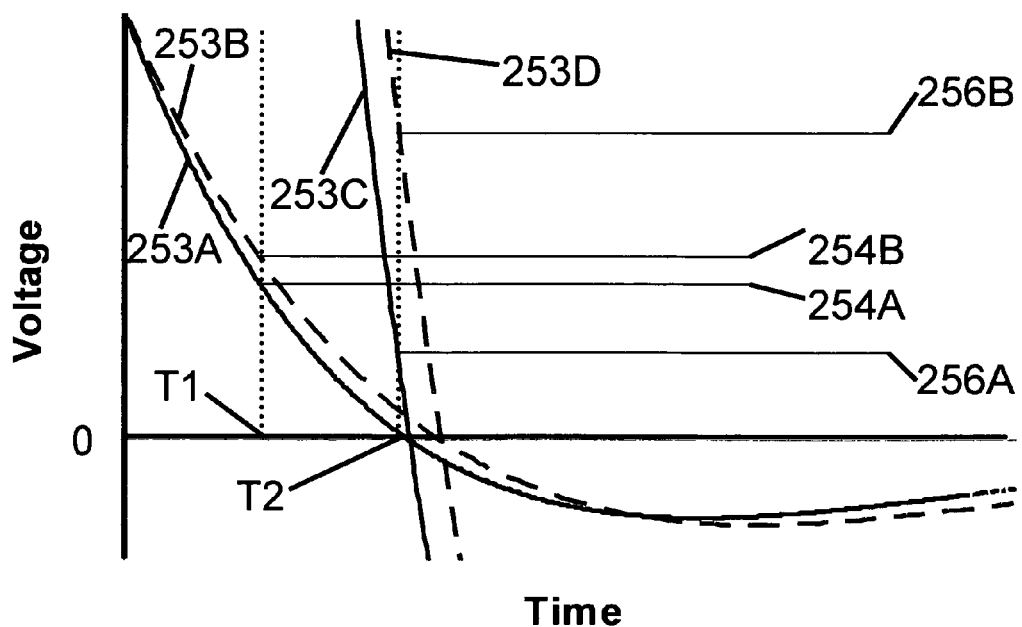
FIG. 20 illustrates the low gain output and the high gain output of the monitoring system of the invention with different sensor displacements.

In FIG. 20 curves 253A and 253B represent the magnitude of the low gain amplified signals as latched at time T1 and stored as DC values 254A and 254B in the sample and hold circuit 198, for a small relative change in core 52 insertion. Curves 253C and 253D represent the high gain amplified signals (in this case about 10× the low gain amplification) as latched at time T2 and stored as DC values 256A and 256B in the sample and hold circuit 192 for the same small change in insertion. In this instance the small change in insertion has generated a voltage change of the difference between the low gain curve 254A and 254B, while the high gain circuit has provided a much larger change in voltage, that being the difference between 256A and 256B. This illustrates the greater sensitivity provided by the high gain amplifier 186.

In operation, the low gain sample and hold circuit 198 is latched to store a sample of the magnitude of the output from the low gain amplifier 184 at time T1 and stores that DC value until a subsequent time T5 (times T1-T5 represent successive system timing periods). The high gain sample and hold circuit 192 is latched to store a sample of the magnitude of the output from the high gain amplifier 186 at a later time T2 and stores that DC value until time T5.

At times T3-T4 the output from the sample and hold circuit 198 is digitized by the A/D converter 196, while during times T4-T5 the output from the sample and hold circuit 192 is digitized by the A/D converter 194

With the initial system timing parameters set, and in the event that the core 52 was not positioned for system midrange operation, the output of the high gain amplifier 186, or both amplifiers 184 and 186 could be driven into saturation (either high or low). Further, even if the sensor was set for midrange operation, depending upon on the scope of movements of the objects being monitored and the system sensitivity selected, the range of relative movements between the core 52 and the coil 44 may be great enough so as to drive the high gain amplifier in and out of saturation or below zero volts, or both. Furthermore, even if properly set initially, movements of the monitored items, such as in the case of the body, may change the sensor setting as a person changes body positions. Hence, without the control circuit 168 of FIG. 17, subsequent manual resetting of the sensor, or manual adjustment of the system parameters, may be periodically required.

Figure 21:
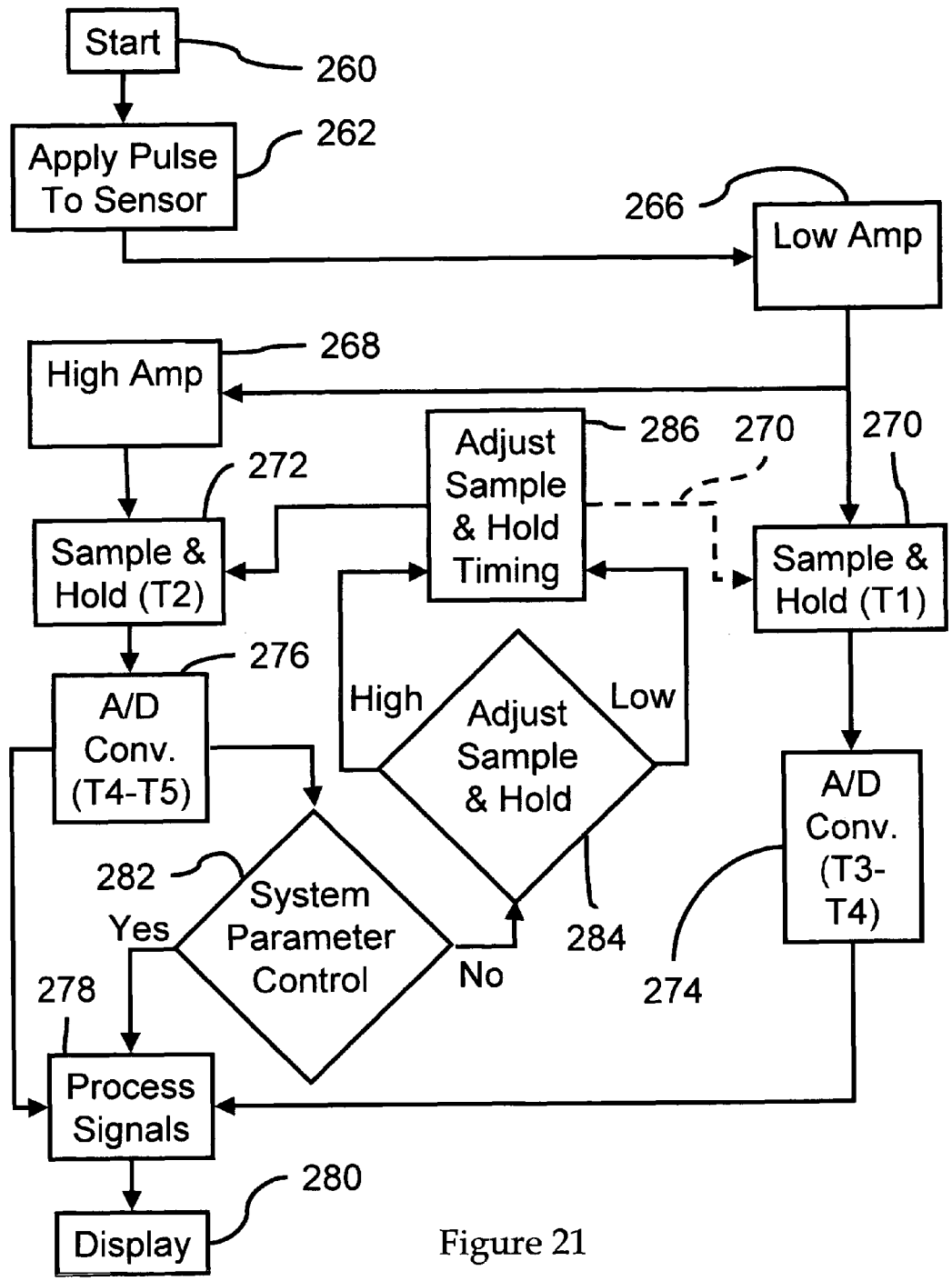
FIG. 21 is a flow diagram for the operation of the bock diagram of FIG. 18 including an arrangement for controlling system timing parameters according to the invention.

FIG. 21 illustrates a process flow chart for the control circuit 168 of FIGS. 17 and 18 illustrating the arrangement of the invention for automatic adjustment of system parameters. The system starts with step 260, applying a pulse to the sensor 160 by step 262. Step 262 applies the response from the pick up winding 44B of the sensor to the low gain amplifier step 266. The amplified output is applied to the high gain amplifier 186 in step 268. Upon occurrence of time T1 after the application of the pulse in step 262, in step 270 the sample and hold circuit 198 is latched to store the DC level from the low gain amplifier at T1. Upon the occurrence of the subsequent time T2 in step 272 the sample and hold circuit 192 is latched to store the DC level of the high gain amplifier at T2. Thereafter at times T3-T4 in step 274 the output from the sample and hold 198 is digitized to provide a first (gross) output indicative of the sensor displacements in digitized form, while at subsequent times T4-T5 in step 276 the output of the sample and hold 192 provides a second more sensitive or definitive output indicative of sensor displacements in digitized form. The digital outputs of steps 274 and 276 are processed in step 278 to create the data for outputting to the computer 174 for the display step 280.

The output of step 276 is also applied to a system parameter control step 282. If the step 282 detects a system midrange operation condition, it signals a YES to the step 278 to output valid data. If system midrange operation was not detected, step 282 signals a NO to the adjust sample and hold timing step 384 to provide one of two outputs, HI and LO, to the change the latch timing parameters of the sample and hold circuits in step 286. The step 286 adjusts the timing of T2 in a direction toward reaching system midrange operation. Time T1 remains fixed so that the output of the low gain amplifier can be observed while the timing of T2 is changed, or can also be adjusted as illustrated by the dashed line 270. The process is repeated until system midrange operation has been achieved.

Figure 22:
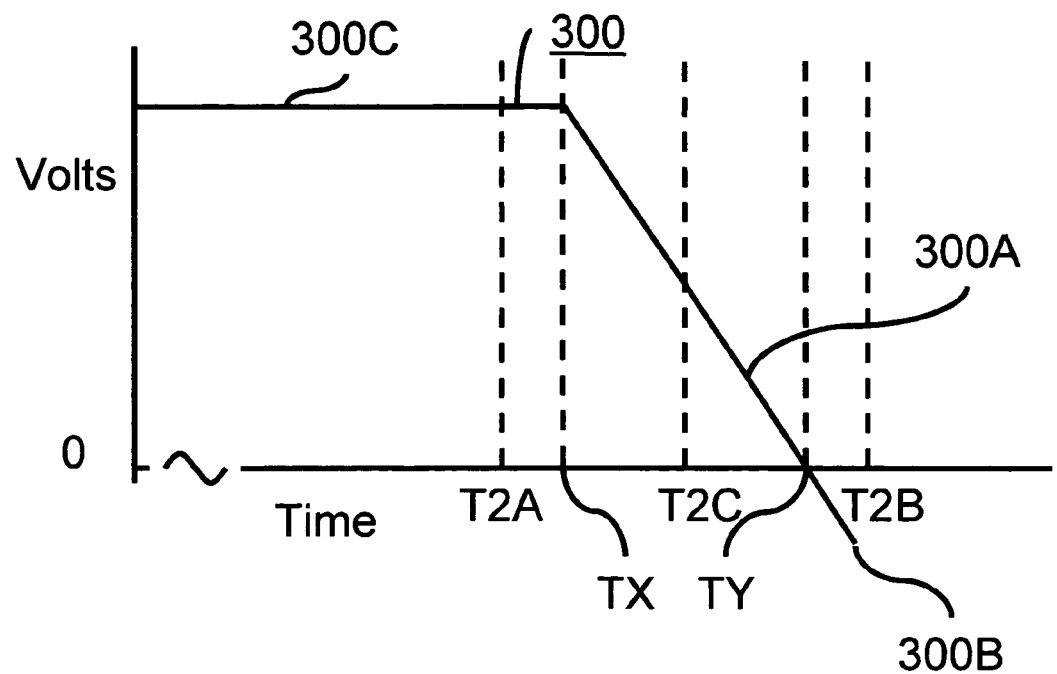
FIG. 22 includes an illustration of the saturation and zero crossover or polarity change operation of the high gain amplifier.
Figure 23:
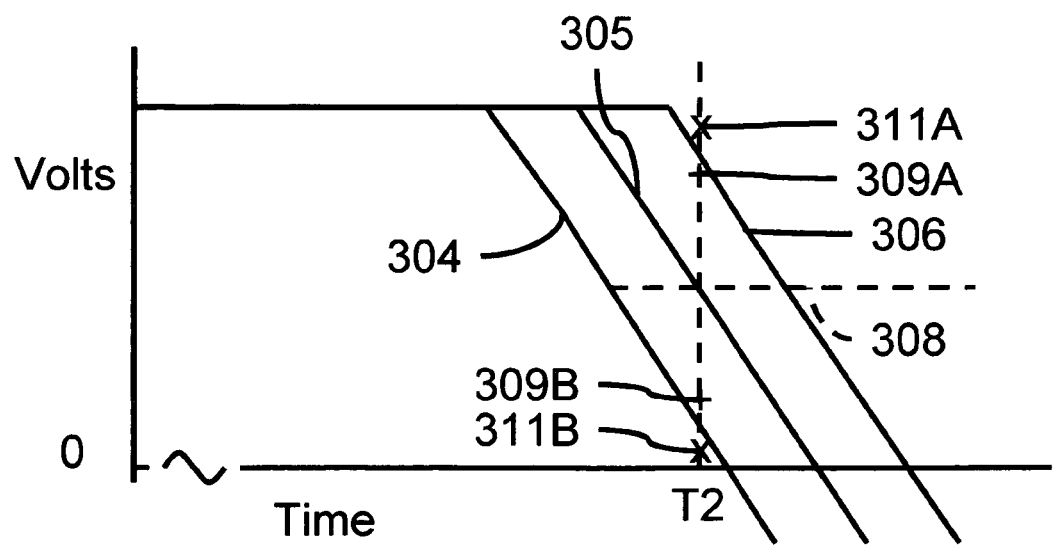
FIG. 23 includes an illustration of the output of the high gain amplifier showing a system selected range of operation.

FIGS. 22 and 23 provide a further explanation of the automated system midrange operation acquisition process of the invention. In FIG. 22 the curve 300 represents the DC output from the high gain amplifier 186 corresponding to selected output levels of the decaying sensor signals, amplified by for example a factor of 5×-100×. The amplifiers output a range of DC signal magnitudes between saturation 300C at time TX and zero volts at time TY (the zero cross over point monitoring system reference). Operation from saturation 300C and zero cross over defines full scale available system sensitivity depending upon the gains selected for the amplifiers. The monitoring system of the invention selects a point of operation adjacent to the zero cross over such as time T2C where a well defined region of the decaying signal reflects the inductive reaction of the input winding and changes therein due to the relative displacement of the coil 44 and core 52 that generally follows the equations:

$$V_L = V_0 \left[ \begin{array}{l} \dfrac{(RC+\alpha_O)}{2\alpha_O} \exp\left(-\dfrac{RC+\alpha_O}{2LC}t\right) - \\ \dfrac{(RC+\alpha_O)}{2\alpha_O} \exp\left(-\dfrac{RC+\alpha_O}{2LC}t\right) \end{array} \right]$$

for the under damped case or, $$V_L = V_0 \frac{RC}{\sqrt{LC}} \exp\left(\frac{-R}{2L}t\right)\left(\left(\frac{RC - \frac{2L}{R}}{\alpha_U}\right)\cos\left(\frac{\alpha_U}{2LC}t + \phi\right) + \sin\left(\frac{\alpha_U}{2LC}t + \phi\right)\right)$$

for the over damped case where:

$$\phi = -a\tan\left(\frac{RC}{\alpha_U}\right)$$
$$\alpha_O = \sqrt{R^2C^2 - 4LC}$$
$$\alpha_U = \sqrt{4LC - R^2C^2}$$

L=the inductance of the input winding 44A
C=the capacitance of capacitor 96
R=the resistance of resistor R1

Although a zero cross over point has been selected as the operation reference point it should be understood that a reference level above and below zero (positive or negative) could be selected as the reference point.

Assume at the start of the monitoring process that the position of the core 52 within the coil 44 is such that the output from the high gain amplifier at time T2A, in response to the sensor output, produces a saturated signal as designated 300C. The microcontroller 164 acknowledges the saturation digital value and performs a binary analysis recognizing that the timing between the application of the pulse to the sensor and the latching of the sample and hold circuit 192 needs to be increased. Assuming further that the microcontroller 164 changes the latch timing to time T2B, in which case the curve 300 falls below zero volts designated as 300B. The microcontroller 164 recognizes that the modification to the latch timing was too great, and selects a shorter delay (one half of the difference). The process continues by incremental steps in shorter time segments until the time T2C is reached generally midway between the high gain amplifier 186 saturation and zero output.

With regards to FIG. 23, with the system midrange timing operation selected, the output from the high gain amplifier 186, for example, can vary over the sensor operating range as illustrated between curves 304 (lower core 52 insertion), and curve 306 (higher core 52 insertion). Curve 305 is at the midrange position. Level 308 is ideal system midrange operation, however the selected midrange of voltages may vary, for example between the system midrange levels 309A and 309B (selected, for example, to operate over 60% of the range of high gain amplifier output, between levels 311A and 311B) as long as the voltage detected does not swing into saturation or fall below zero.

Assuming that the sensor moves and changes its initial midrange setting, such as in the case when monitoring body skin and the patient changes body position, the system midrange timing setting initially selected may need to be changed wherein and the curves 304 or 306 at time T2 may reach saturation, or drop below zero. The microcontroller 164 identifies the out of range conditions and will reset the timing parameters for operation adjacent a new zero cross over point as new system midrange operation. Hence the monitoring system of the invention is adapted to change its operating parameters to adapt the monitoring system to reset its operation reference point to a new zero cross over point. With this arrangement accurate measurements of coil 44 and core 52 relative displacements have been made over 80% of the range of the sensor. The range of the sensor can be expanded for example by compensating for non-linearity introduced near the ends of the coil 44 by increasing the windings of wire near the ends.

On the other hand, if a series of movements detected by the sensor at time T2 are so large as to drive the output of the high gain amplifier 186 beyond both saturation and below zero, the microcontroller 164 can reduce the gain parameters of the system, such as for example lower the gain of the low gain amplifier, or the high gain amplifier, or both.

Figure 24:
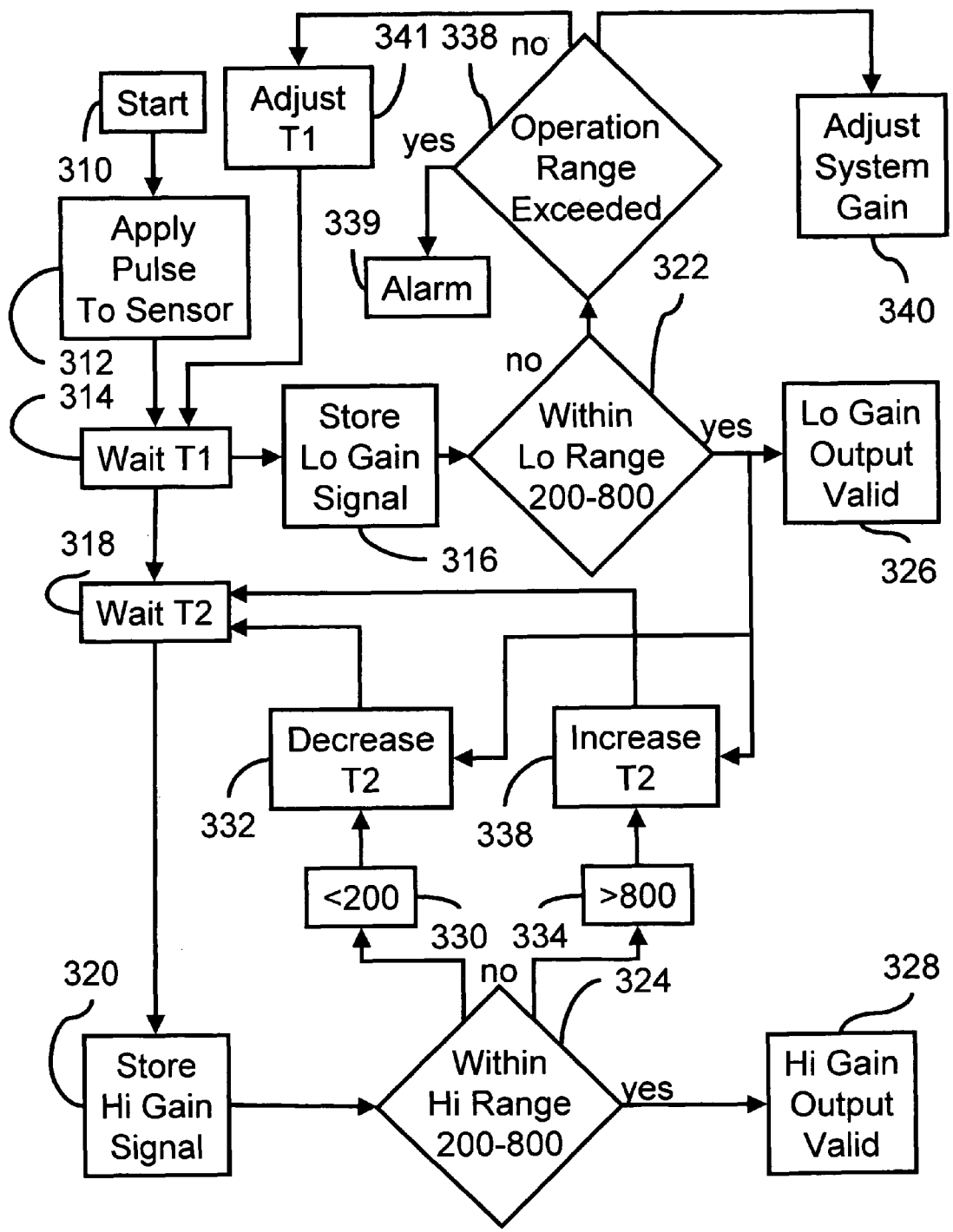
FIG. 24 is a flow diagram of the operation of the system including an arrangement for controlling the system timing and gain parameters according to the invention.

FIG. 24 is a software flow diagram describing the binary analysis used by the microcontroller 164 for selecting system timing and gain parameter settings. The start step 310 initiates step 312 to apply a pulse to the sensor 160. After the time delay of T1 of step 314, step 316 allows the sample and hold circuit 198 to latch and store the magnitude of the low gain amplifier signal present at T1 and to continue to store the signal until time T5. After the delay of T1, at time T2, step 318, the step 320 allows the sample and hold circuit 192 to latch and store the magnitude of the high gain amplifier signal present at T2 and to continue to store the signal until time T5.

During times T3-T4 a step 316 outputs a range of binary signals between digital values of 0-1023 (such as with a 10 bit A/D converter) corresponding to the magnitudes of the signals stored in the low gain sample and hold circuit 198 as latched at time T1. During times T4-T5 the step 320 outputs binary signals between digital values (such as 0-1023) corresponding to the magnitudes of the signals latched in the sample and hold circuit 192 at time T2. A reduced range of digital values of 200-800 (out of 0-1023) has been selected for system midrange operation (corresponding to the range of DC levels between points 309A and 309B of FIG. 23). It should be understood that the digital values set forth above are exemplary and other values could be used.

If the output received by step 324 is within the range or 200-800, a YES signal is sent to step 328 indicating the high gain output is valid enabling the microcontroller 164 to output definitive output signals indicative of the sensor displacements to computer 174. If the output received by step 324 is less than the digital value 200, a NO signal is applied to step 330, which applies an enable signal to step 332 to decrease the timing of T2 in step 318. If the output received by step 324 is greater than the digital value 800, a NO signal is applied to step 338, to increase the timing of T2 in step 318. It should be noted that the initial system timing and gain parameters control process could take place even while the sensor is being attached to the monitored item and while it is moving (such as skin contraction and expansion during breathing). The other enabling signal for steps 332 and 338 is received in the form of a YES output from step 322 indicating that the low gain was within the binary range of digital values 200 to 800. The YES output of step 322 is also applied to step 326 indicating that the low gain output is within the range of operation (valid output) enabling the microcontroller 164 to output the gross output signals of system operation. If the output received by step 322 is less than the digital value 200 or greater than 800, a NO signal is applied to step 338 which applies a YES signal to the alarm step 339 and to the system gain adjust step 340, in which case the gain of the low gain amplifier 184 is adjusted.

Alternately, if the scope of movement of the core 52 within the coil 44 exceeds the range of the high gain amplifier 186, instead of adjusting the gain of the low gain amplifier 184, step 324 can adjust the gain of high gain amplifier to encompass the expanded range of movement (not shown). Also, if desired, the time T1 can also be adjusted via the adjust T1 step 341.

Hence it can be seen that the control circuit 168 controls the operating parameters of the sample and hold circuit latch timing relative to the input signal and/or the gain of the amplifiers, for matching the linear impedance changes within the scope of the sensor displacements to the range of selected digital signals (200-800) for achieving system midrange operation. With both the amplifier gains set for a desired degree of sensitivity (such as 100×), and with the range of digitized sample and hold DC magnitudes selected for midrange operation (such as 200-800 out of 0-1023 corresponding to 0.65 to 2.58 volts out of a supply of 3.3 volts) for midrange operation, the control circuit 168 varies the timing between latching and the application of a pulse to the sensor (T2 and if desired T1) so that when the scope of the magnitudes of impedances of the sensor outputs fall within the selected digital range (200-800) for midrange operation. If the sample and hold magnitudes exceed the selected range, near saturation or near zero output, (above 800 or below 200) the latch timing will be reset to encompass the change of magnitudes. If the sample and hold magnitudes exceed the selected range both above and below (above 800 bits and below 200 bits) the sensitivity of the system can be reduced by decreasing the gain of the amplifiers. The objective is to adjust the system timing and sensitivity for operation optimized for monitoring the scope of displacements.

Figure 25:
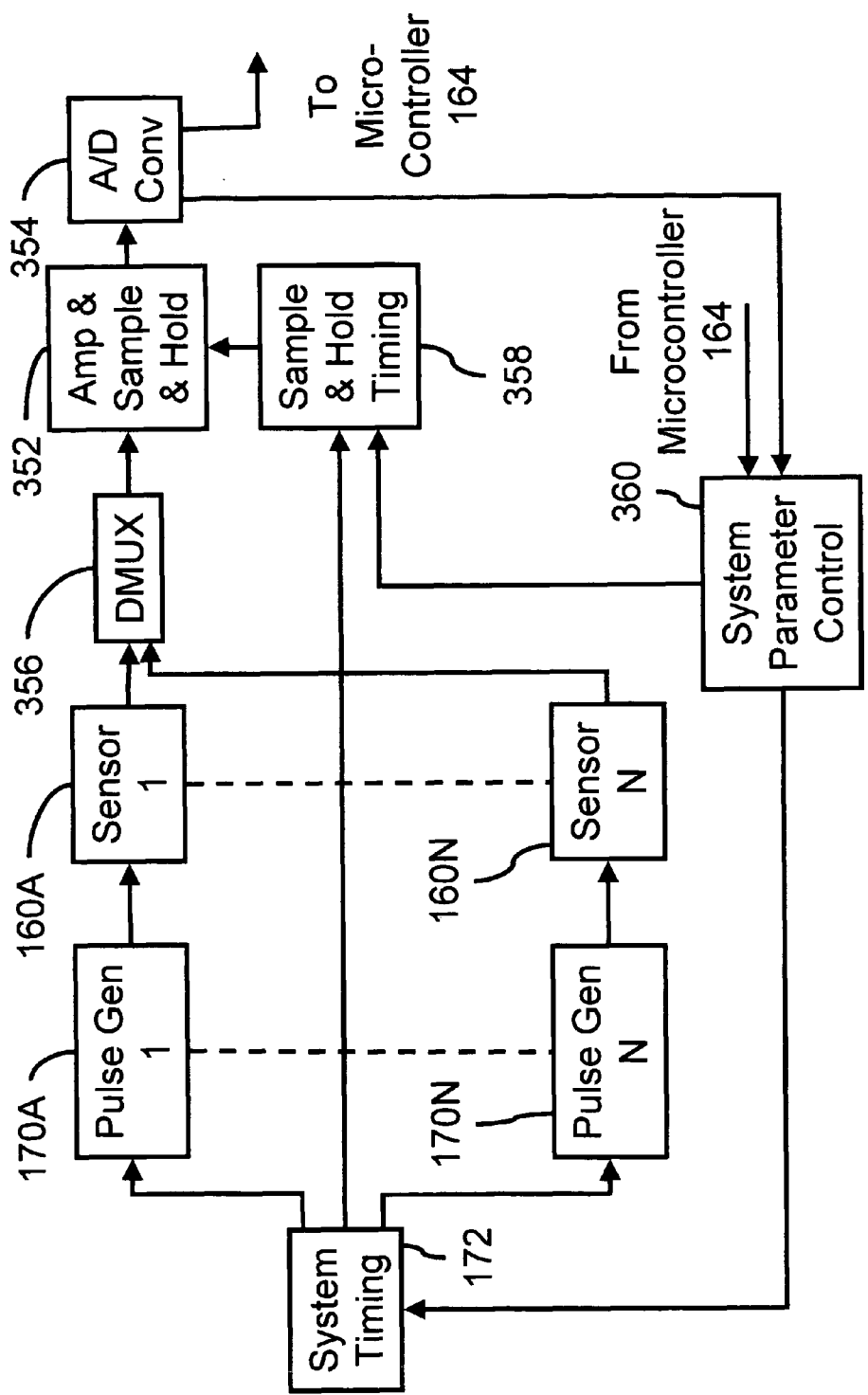
FIG. 25 illustrates an embodiment of the invention for monitoring with the use with multiple sensors.

In accordance with the invention a plurality of sensors can be arranged in a positional array representing topographical movements in several directions and locations, such as for example, of the skin of the stomach of a woman in labor, and computer 174 algorithms can be used to coordinate all the data for an overall diagnosis. FIG. 25 shows a monitoring arrangement in which multiple sensors are employed, such as for example measuring displacements in various directions. The pulse generators 170A-170N apply pulses to separate sensors 160A-160N. Each sensor 160A-160N outputs signals via the DMUX 356 to the amplifier and sample and hold circuit 352 and A/D converter circuit 354 to the microcontroller 164. Timing circuit 358 controls the latch time of the sample and hold circuits 352 under the control of the microcontroller 164 via the system parameter control circuit 360.

The timing sequence for the multi-sensor embodiment of FIG. 25 for multiple sensors can include the following steps:
1) initiate the data test cycle of sensor 160A by interrupting the system sleep power saving mode of operating and toggling the amplifiers on,
2) apply pulse to sensor 160A,
3) after a delay of about 2.5 μsec (T1) connect the output of low gain amplifier to its sample and hold circuit,
4) after a delay of about 1.5 μsec disconnect and therefore latch the average output of the low gain amplifier during step 3,
5) after a delay of 0-15 μsec (variable T2) connect the high gain amplifier to its sample and hold circuit,
6) after a delay of about 1.5 μsec disconnect and therefore latch the average output of the high gain amplifier during step 5,
7) perform an A/D conversion of the low gain sample and hold voltage (100 μsec),
8) perform an A/D conversion of the high gain sample and hold voltage (100 μsec),
9) place the system in the power savings sleep mode and toggle amplifiers off until the initiation of the next sensor test cycle,
10) repeat steps 1-9 for the rest of the sensors,
11) commence re-charging all the capacitors in the pulse generators (1.5 msec),
12) store digital data from all sensors in dedicated data FLASH memory (8 msec),
13) transmit data to computer (1 msec), and
14) place system in power savings sleep mode and toggle the amplifiers off until the next test cycle is initiated.

Since the A/D converters are sensitive to ground bounce noise, the charging and discharging of the pulse generators capacitors should not take place while the A/D conversion process is underway. The consistency of timing from the discharge step 1 to the latch steps 4 and 6 is critical, so that a crystal oscillator as opposed to an RC oscillator is preferred for use as the system high frequency clock.

The timing involved in the monitoring system of the invention has the advantage of providing a responsive system for monitoring rapid changes. On the other hand if the system is used to monitor relatively slow changes such as monitoring breathing, the increased time in sleep mode with the reduced duty cycle will conserve battery power.

FIGS. 26A through 26D include flow diagrams that illustrate the functions of exemplary software programs for the invention. The software programs include a main program and subroutines that are used to control the operations of the system, including the power saving sleep mode of operation to reduce power drawn from the batteries. The monitoring circuit 162 and the microcontroller 164 have several different clock domains for the CPU, input/output, FLASH, and A/D converters. All these domains run off a high frequency crystal clock (some at stepped down frequencies). The asynchronous system timer runs off a low frequency crystal clock. When the system is being used in the ambulatory mode, and the sleep mode is initiated, all clock domains are shut down, except the asynchronous timer and the current consumption drops from milliamps to microamps. When the microcontroller 164 is connected to transmit data to the computer 174, the input/output domain requires operation and standby current is in the milliamp region. However this does not impact the battery power supply since the interface 165 between the microcontroller 164 and the computer 174 has its own power supply and a 3.3 volt output. The programs used in this invention were written for an 8 bit microcontroller using "C++" and machine language programming, and code for the computer was written with "Visual Basic". However, the invention is not limited by this selection of electronics, microprocessor, programming language or any of the programming methods described herein.

Figure 26A:
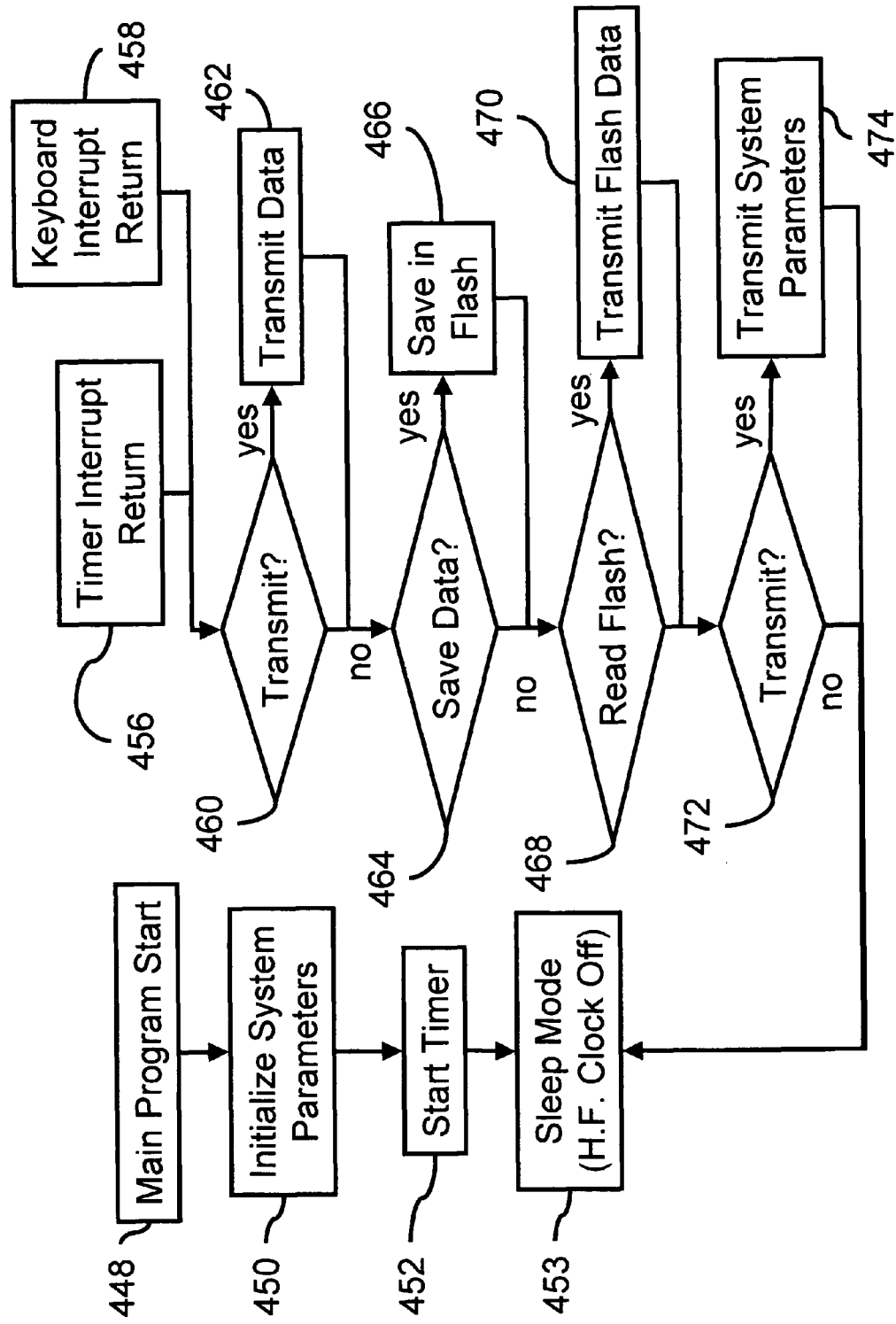
FIGS. 26A-26D include software flow diagrams for use in the system of the invention including a power savings feature.

The flow diagram of FIG. 26A begins for the main program beginning at start 448. The system parameters are initialized in step 450 in which key system variables such as capacitor discharge and sample and hold latch timing are set to starting values and system buffers are cleared. In step 452 the system timer is started and the system is put into the sleep mode 453. In this mode, various operations requiring power consumption are disabled to save power while waiting for an interrupt signal. An interrupt signal can come from the system timer interrupt 456 or the computer keyboard interrupt 458 which are described with regard to FIGS. 26B, 26C, and 26D.

When the functions called by an interrupt are complete, the system returns to either timer interrupt return 456 or keyboard interrupt return 458 depending on the type of interrupt. After returning from the interrupt, a flag to test whether to transmit data is checked in step 460. If yes, data is transmitted in step 462. The system then moves to test whether to save the data in step 464. If yes, data is saved in FLASH memory 466. The system then moves to test whether to read the data in stored in FLASH memory in step 468. If yes, the data is read in step 470. The system then moves to test whether to transmit the system parameters 472. If yes, the system parameters are transmitted in step 474. The system then moves back to step 453 to enter sleep mode and begin the process again. The system timer continues to run continuously and asynchronously so that the period between measurements is not impacted by any of the decision tree steps 460, 464, 468 or 472 or by the initiation of sleep mode.

Figure 26B:
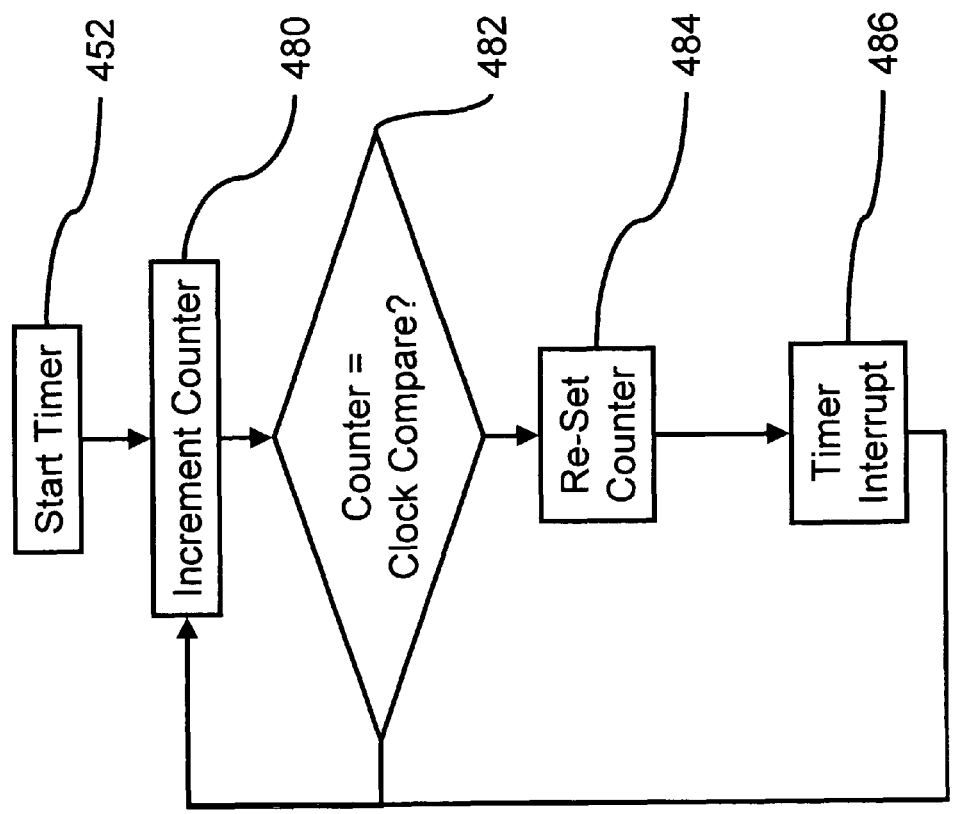

In FIG. 26B, the functions of the system timer are illustrated beginning with step 452 to start the timer. In step 480, a counter established a set point for a timed interrupt and is incremented. In step 482, the counter is compared with the system timer. If the counter value is less than the timer value, the system returns to incrementing the counter in step 480. When the value of counter equals the clock value, the system moves to step 484 to reset the counter. Then the timer interrupt step 486 is then executed moving the system from the sleep mode 453 (FIG. 26A) to the timer interrupt 486 shown in the process flow of FIG. 26C.

Figure 26C:
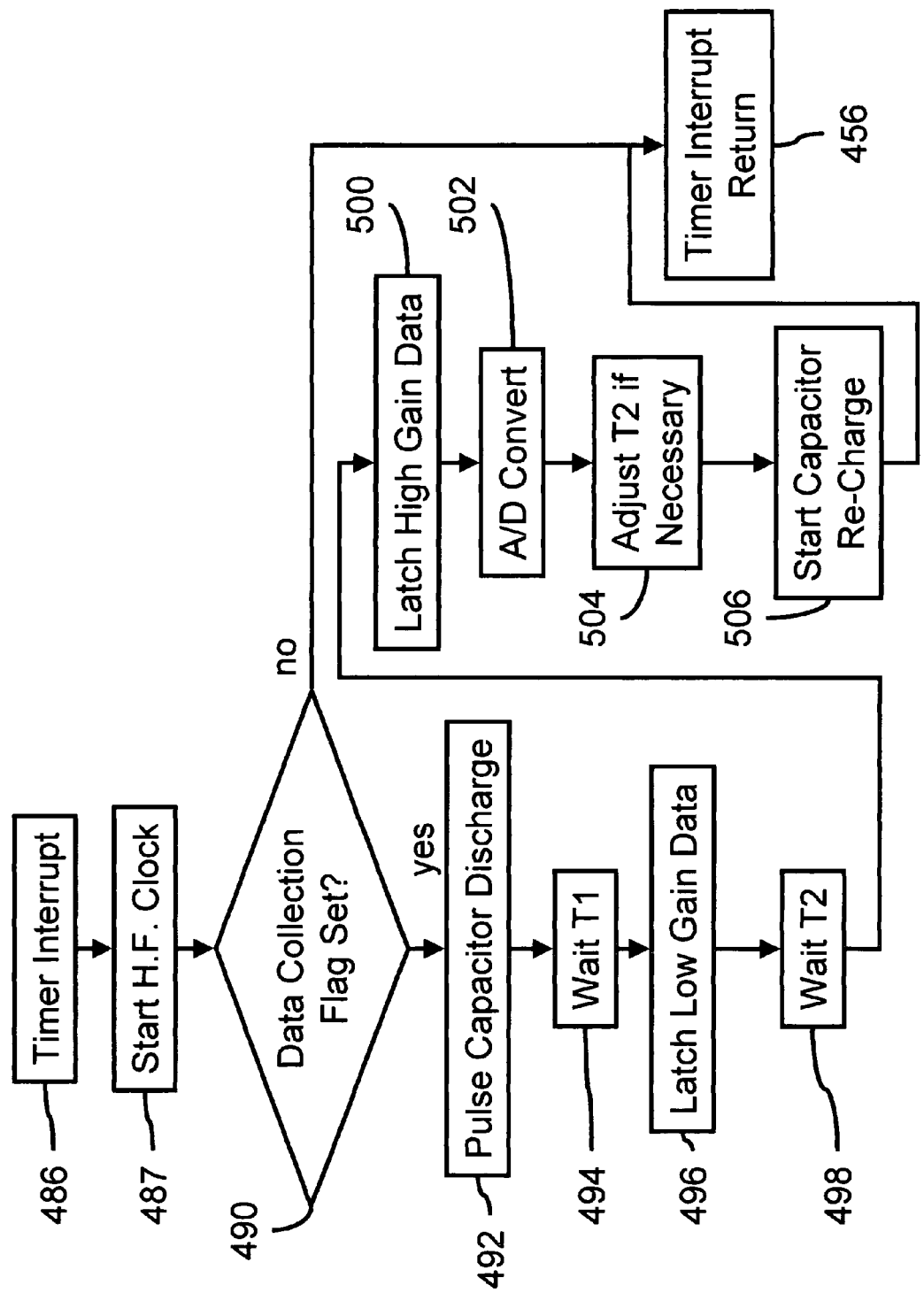

In FIG. 26C, the timer interrupt subroutine begins at block 486 that starts the high frequency clock of step 481. A test is performed in step 490 to determine if the data collection flag has been set to "yes." If "yes," the system progresses to step 492 in which capacitor 96 is discharged. This initiates the beginning of the data generation process. After the capacitor discharge step 492, the system will wait time T1 in step 494, to latch the low gain data in step 496. The system will then wait time T2 in step 498 to latch the high gain data in step 500. The system will perform an analog to digital conversion process of the latched low gain data in step 496 and then the high gain data of step 500. The timing T2 may need to be adjusted. This operation is performed in step 504. The capacitor 96 (FIG. 11) is then re-charged in step 506, and the system returns to the main program at step 456, timer interrupt return in FIG. 26A.

Figure 26D:
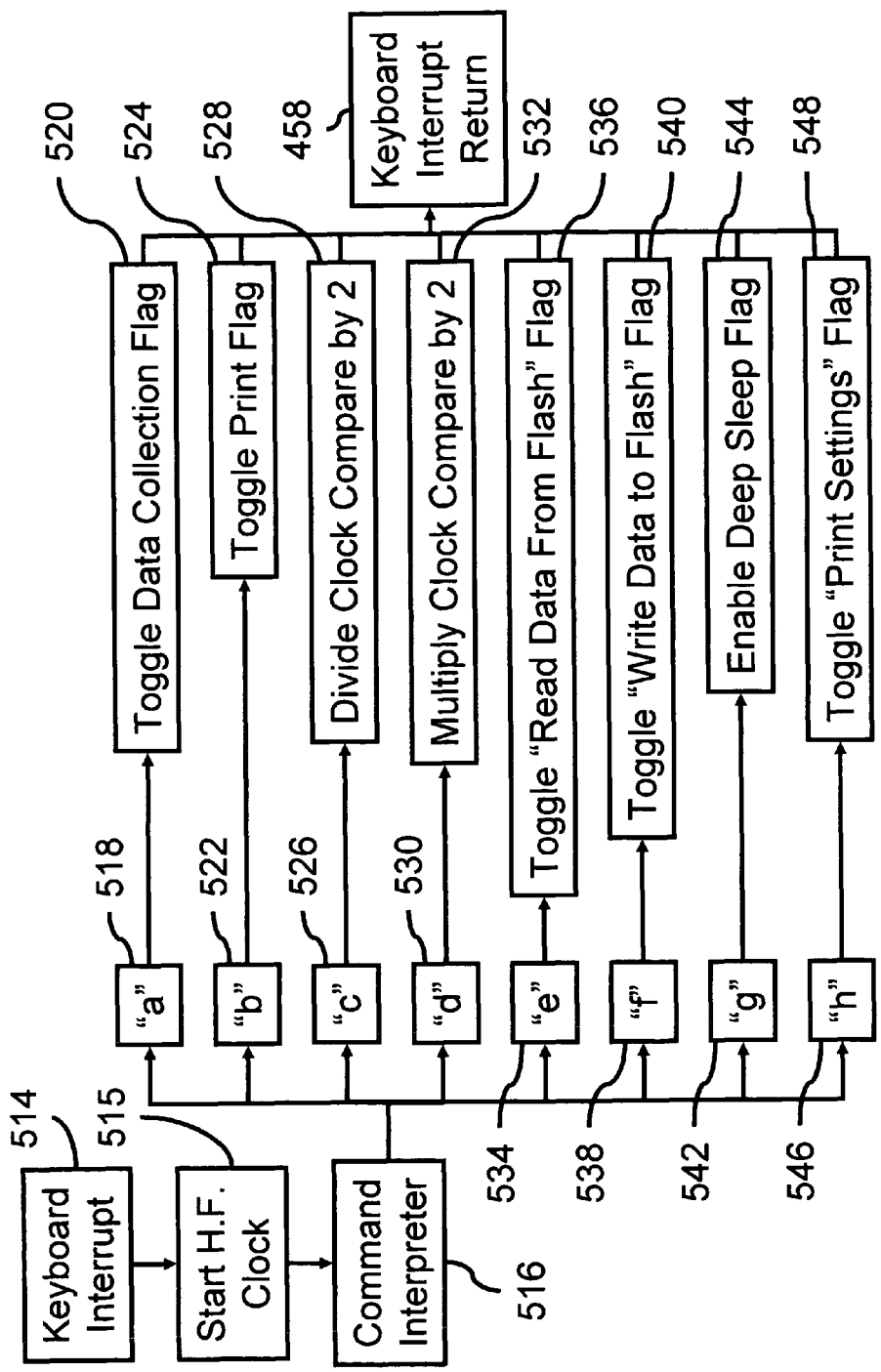

The process flow for a keyboard interrupt of the computer 174 is demonstrated in FIG. 26D. The keyboard interrupt 514 is a manual interrupt to the system that starts the high frequency clock in step 515. The command interpreter step 516 responsive to the high frequency clock signal enables data to be received from the keyboard. A number of keyboard inputs are assigned specific commands that the system can execute. A keyboard input of an "a" 518 will toggle the data collection flag to on (or off) in step 520. A keyboard input of a "b" 522 will toggle the system to print (or not to print) data in a real time mode in step 524. A keyboard input of "c" 526 will reduce the frequency of the data collection step by one half of the current frequency of step 528. An input of "d" 530 will cause the system to double the data collection frequency as show in step 532. If the system receives a keyboard input of "e" 534 it will read the data from the microcontroller 164 FLASH memory as in step 536. An input of "f" 538 will cause the system to store data to the FLASH memory in step 540. An input of "g" 542 from the keyboard will toggle the power consumption during sleep mode 453 as in step 544. An input of "h" 546 will toggle the print settings flag in step 548. A plurality of additional keyboard inputs are included in this invention and the capability of providing manual input to the system is not limited to the features described herein. Upon completion of the process initiated by the keyboard interrupt, the system will move to the keyboard interrupt return 458 and back to the processes associated with the main program illustrated in FIG. 26A. In addition, certain of these commands may be given by the microcontroller 164 due to external input. For example, the system can determine through an input whether or not it is connected to an external connector and toggle the sleep setting and the "print" setting accordingly. As another example, the system can determine through an input whether or not it is connected to an external connector, and if not connected automatically commence storing the data to non-volatile FLASH memory.

Figure 27:
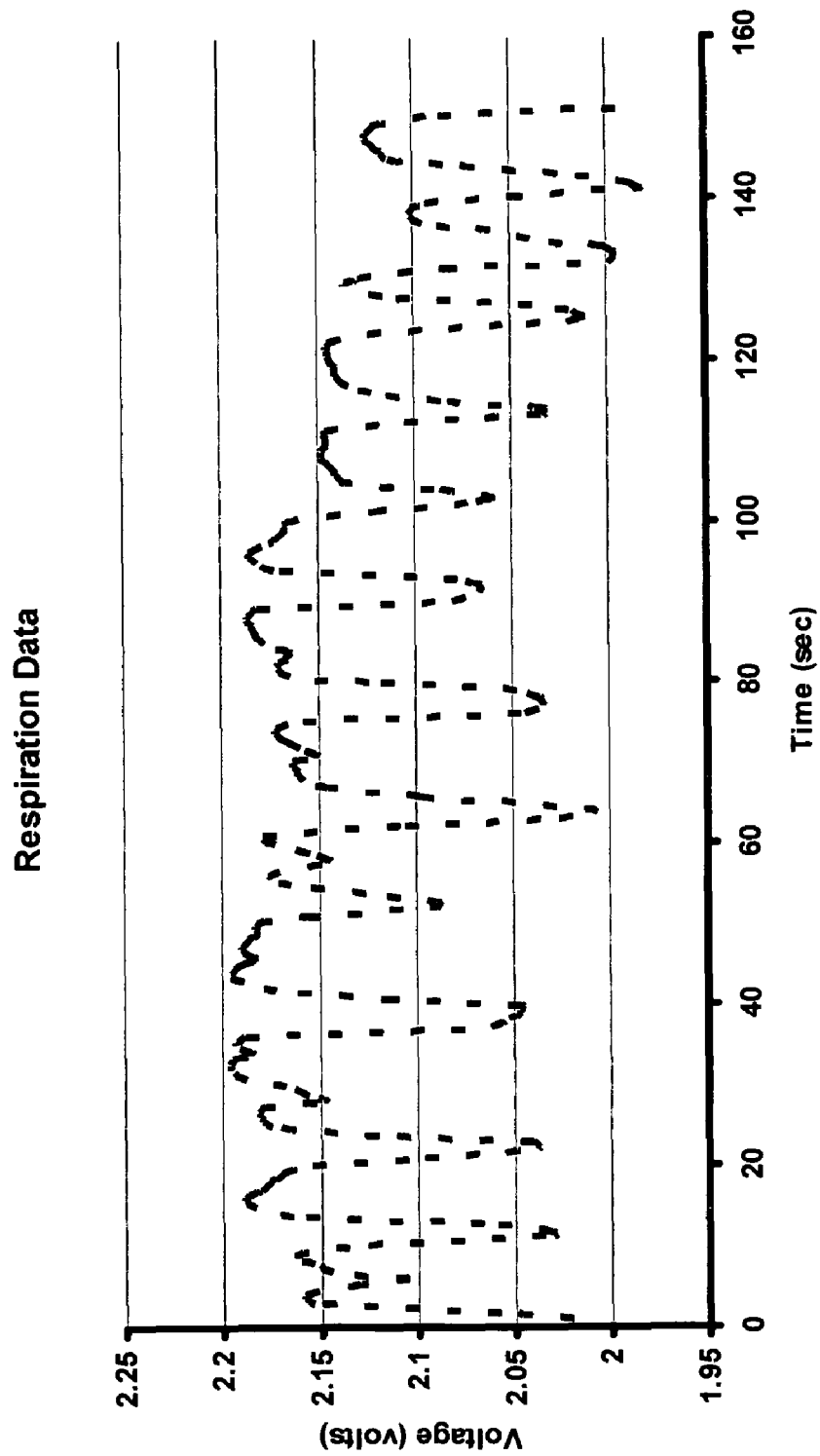
FIG. 27 is a plot of the output of the system of the invention when measuring breathing.

FIG. 27 shows a plot of voltage versus time of the output of the system of the invention with a sensor connected to the body chest to measure respiration illustrating as twelve cycles of breathing over 139 seconds with 130 data outputs from the high gain sample and hold 192 with a timing pulse applied approximately each second. The system midrange operation for the test was approximately 2.1 volts.

With a one second data test cycle, the system full power operation of the invention is about 990 milliseconds for a test data duty cycle of about 0.1% of the test and thereafter placed in a sleep mode significantly reducing the power drain on the system watch type batteries.

Figure 28:
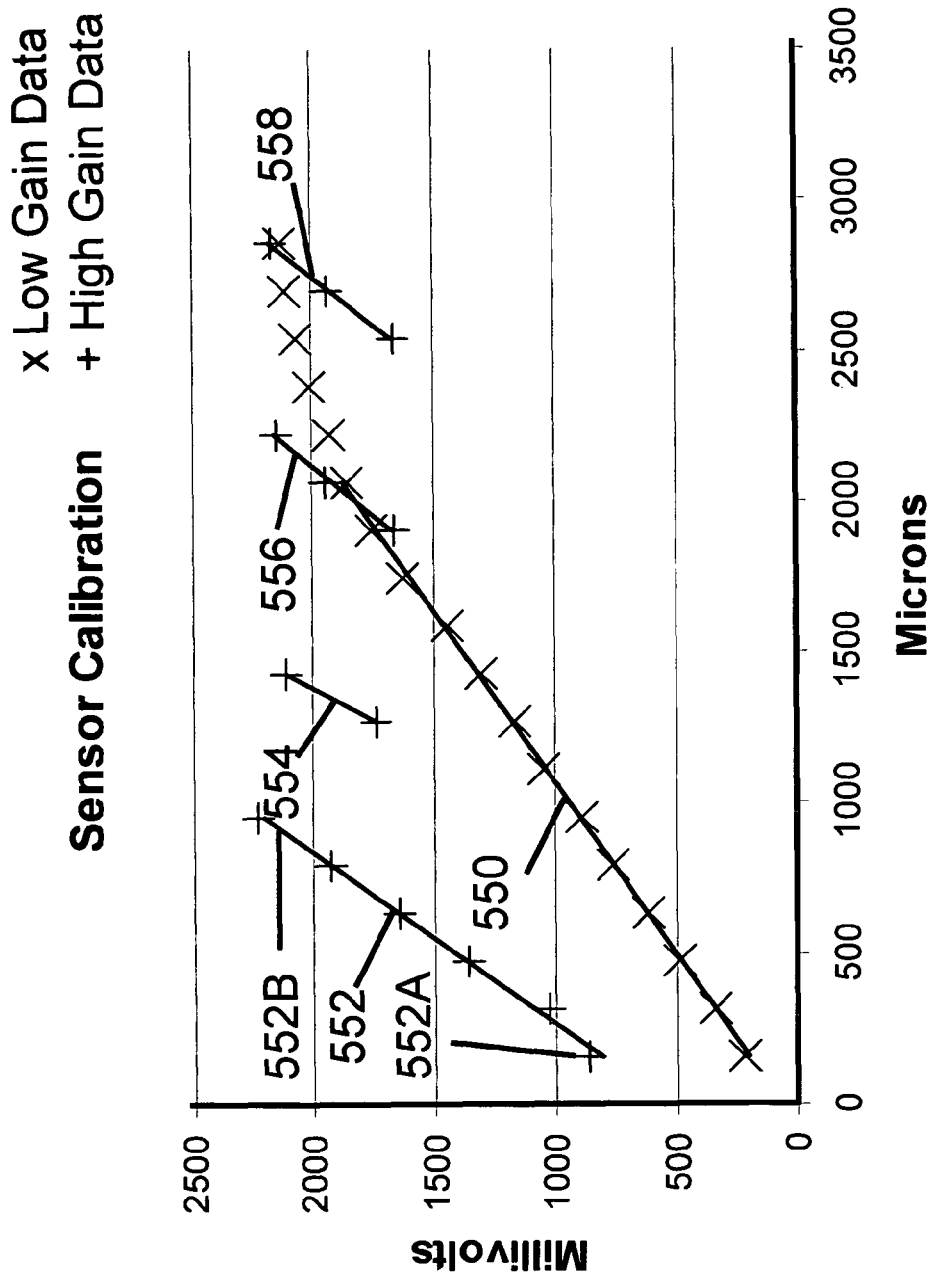
FIG. 28 illustrates the output of the monitoring system of the invention with step type changes in sensor displacement including the operation of the control system for changing the timing parameters of the system.

FIG. 28 is a plot of system operation as a function of the insertion of the sensor rod 52 within the coil 40 in about 125 micron steps to illustrate the automated system timing parameter changes. Curve 550 illustrates the low gain data output (2× amplification). Curves 552-558 illustrate the high gain data output (added 10× amplification).

In this instance, the low gain output was found to be relatively linear over a sensor displacement in the range of 2000 microns.

With regard to the high gain output, starting at point 552A (low initial core insertion) the system output increases relatively linearly with rod insertions in steps of about 125 microns over approximately 625 microns of displacement until point 522B. Core insertion beyond point 522B (1000 microns) results in out of range condition and the control system initiates a change of timing parameter sequence and the system jumps to follow the curve 554 with a new system midrange setting. The timing parameter of the system was changed again beyond approximately 1500 microns to jump and follow curve 556, and again at approximately beyond 2150 microns to jump and follow curve 558, providing generally linear system operation for over 2500 microns.

Figure 29:
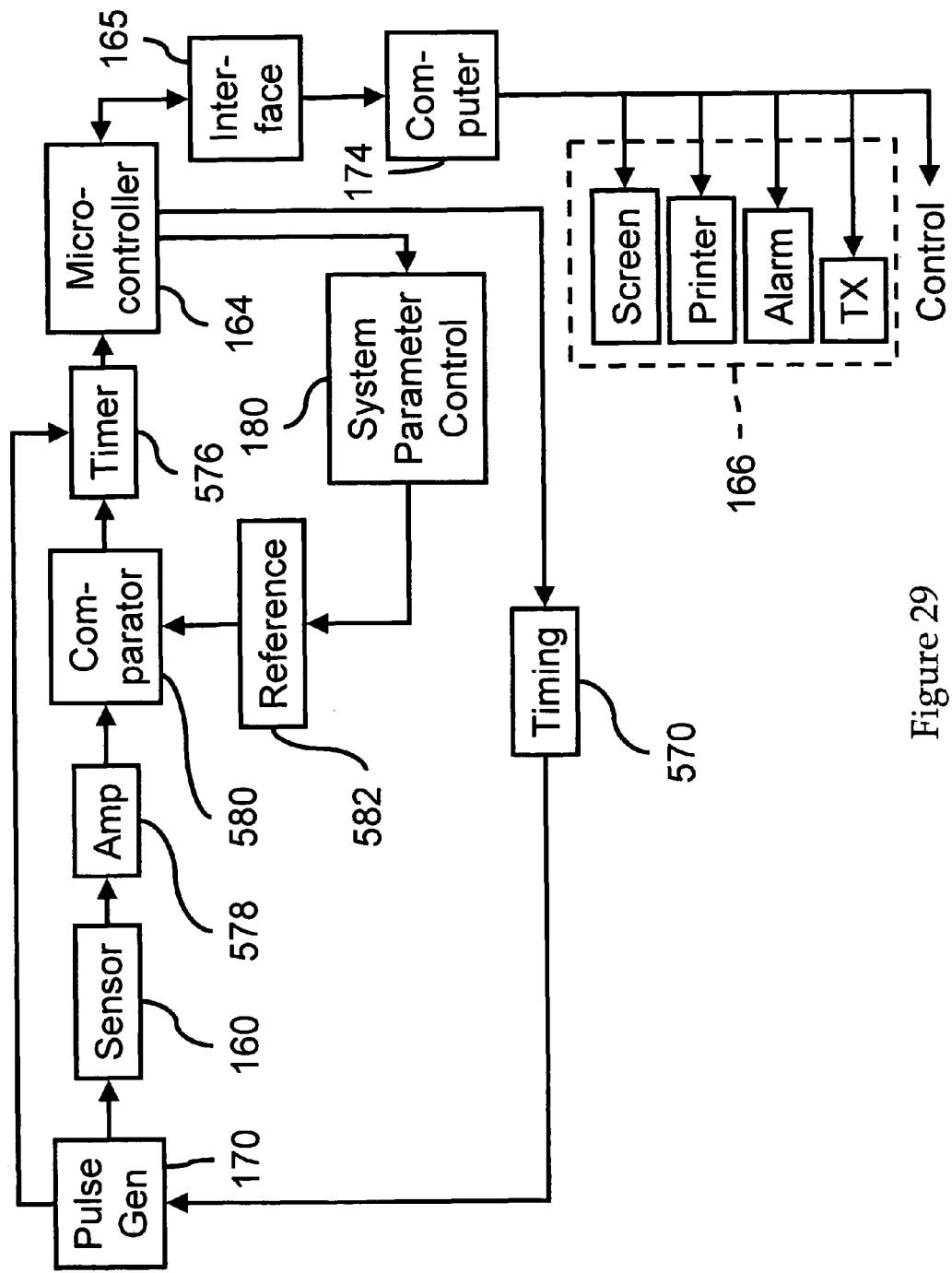
FIG. 29 includes another embodiment of the system of the invention including a time-based concept.

Up to this point, the invention has primarily discussed an arrangement wherein the voltage magnitude of the output from the sensor has been measured at a set time or times. Since the output from the sensor is voltage magnitude vs. time, it is equally viable for the deformation by measuring the time at which the output crosses a set voltage magnitude. FIG. 29 discloses an embodiment of the monitoring system of the invention including a time based system in contrast to the magnitude based system of FIG. 18. Under the control of the timing circuit 570 a pulse is applied to the sensor 160 by the pulse generator 170 and also starts a timer circuit 576. The decaying response of the sensor 160 is applied to an amplifier 578. Depending upon the sensitivity desired, the amplifier 578 can be deleted. The output of the amplifier is applied to a comparator circuit 580. The comparator circuit compares the magnitude of the output from the amplifier 578 to the level from the reference circuit 582. The reference can for example be a selected voltage reference or selected digital level. If the reference is a digital level, the comparator will include an A/D converter and can, for example, use a digital level of 512 (half of 0-1023). When the voltage input goes below the reference, a comparison is validated, and the count reached by the timer circuit 576 is applied to the microcontroller 164 to provide an indication of displacement of the sensor 160. The microcontroller 164 outputs displacement indications to the computer 174 that applies displacement data to the display unit 166. Since the operation of the system of FIG. 29 is time based, depending upon the sensitivity desired, the frequency of the system clock may need to be significantly increased over that for the system of FIG. 18. The microcontroller 164 can also control the magnitude of the output from the reference circuit 582 (via the system parameter control 180) to provide a midrange parameter control for the system.

Figure 30:
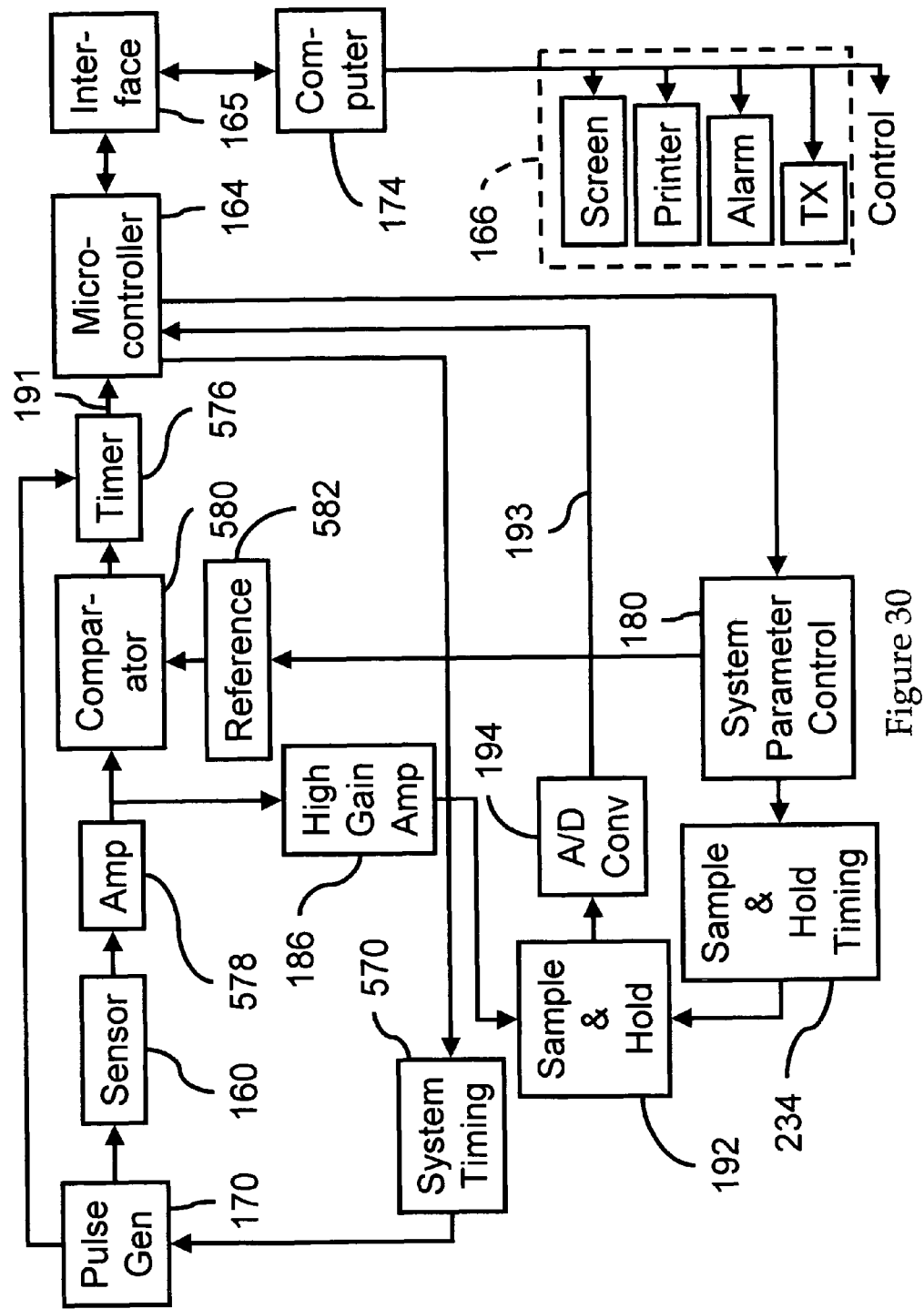
FIG. 30 includes another embodiment of the system of the invention including the time-based concept for the gross output and the voltage based concept for the high sensitivity output.

FIG. 30 is a combination of the systems of FIGS. 18 and 29. The time-based system of FIG. 29 is used to replace the low gain circuitry of FIG. 18 (sample and hold circuit 198, and A/D converter 196) to provide the low gain data (general indication of the sensor displacement) while the high gain data processing remains the same.

The amplifier 578, comparator 580 and timer 586 operate as previously described with respect to FIG. 29 to provide the low gain data to processor 164 on line 191. The amplifier 186, sample and hold 192, A/D converter 194, system parameter select 180, and sample and hold latch timing 234 operate as previously described with respect to FIG. 18. With this arrangement, the binary searches provided by the microcontroller 164 can be eliminated, since the system can utilize the information provided by the timer 576 in order to set the sample and hold timing 234.

The sensor and monitoring apparatus of the invention has been described above for monitoring relative movements without correlation to a zero reference point or starting point, which for many uses reference points are not needed. Further, since the sensor of the invention is Q insensitive, any changes in the intrinsic resistance of the windings due to variations in temperature do not materially vary the inductive reactance exhibited by the sensor. However the inductive reactance exhibited by the sensor varies with changes in the permeability of core with variations of temperature. In many uses the sensor will be in environments that do not experience significant temperature changes, therefore core sensitivity to temperature will not impact the use of the sensor.

Figure 33:
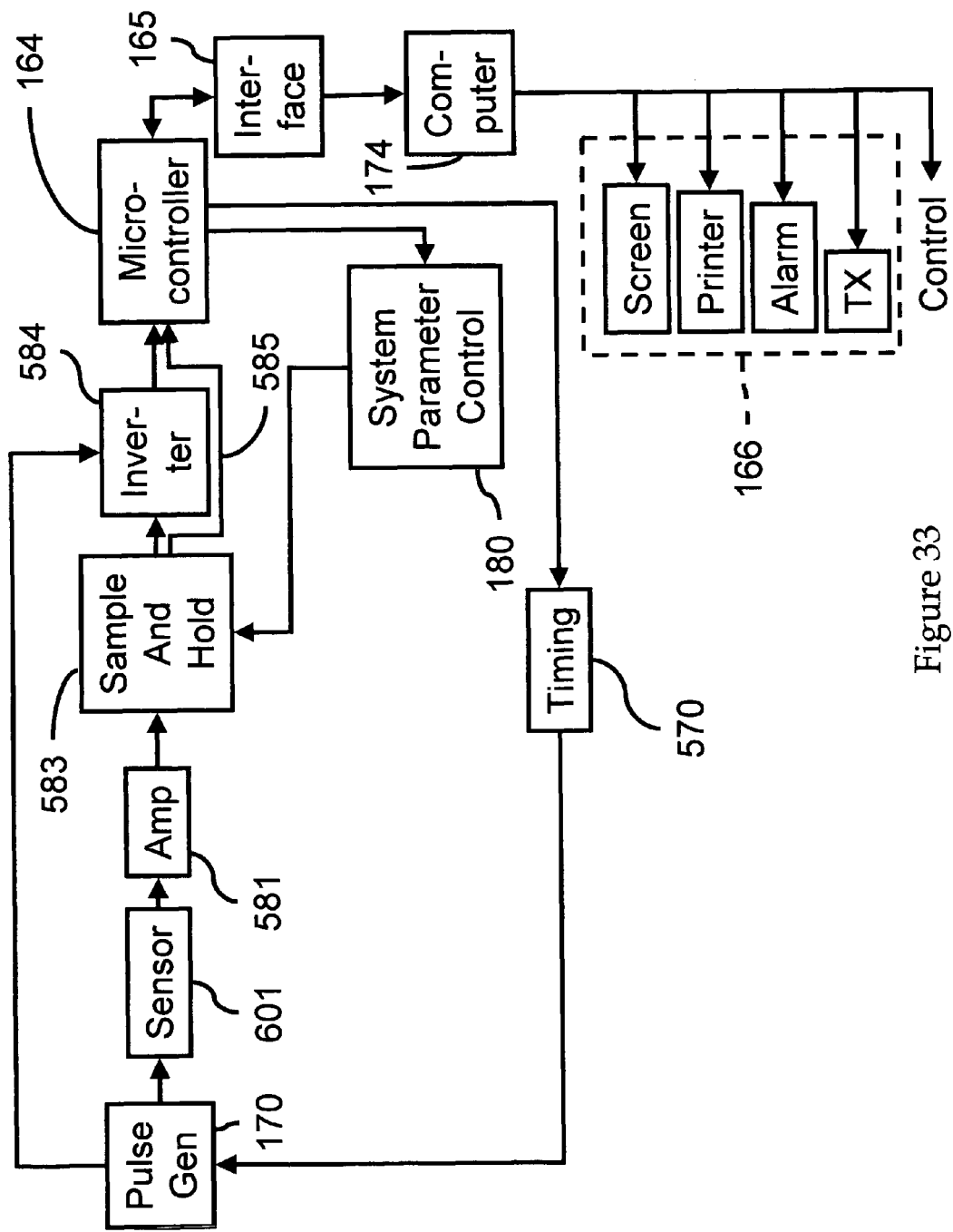
FIG. 33 is a block diagram of a monitoring system for use with the sensor circuit of FIG. 31.
Figure 35:
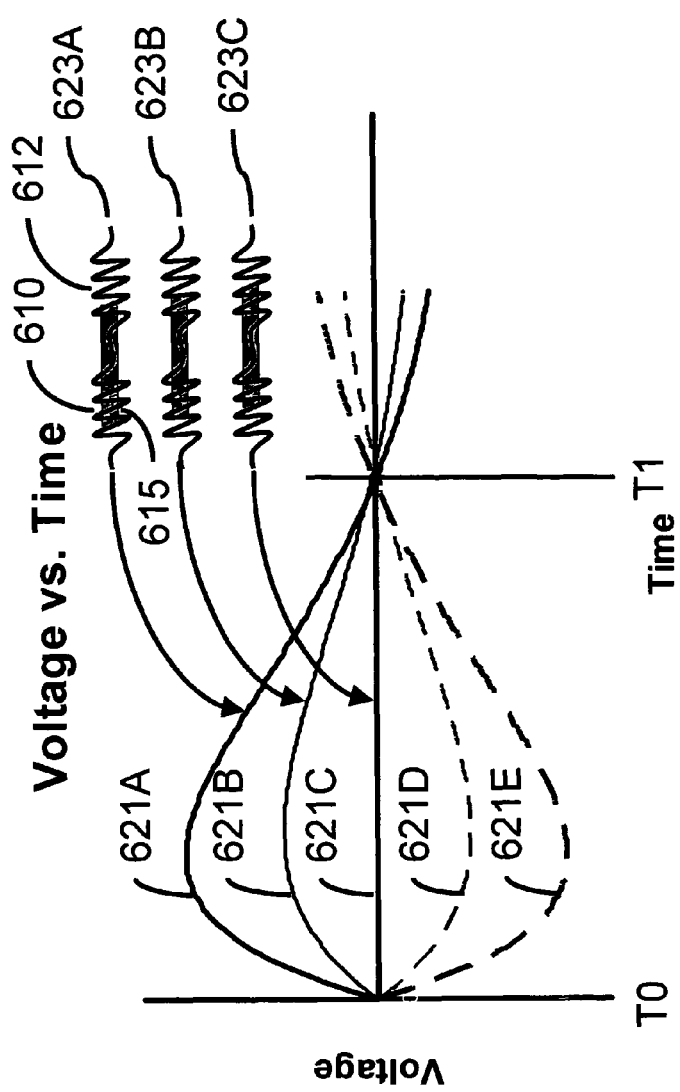
FIG. 35 includes waveforms for illustrating the operation of the sensor circuit of FIG. 33.

FIGS. 31, 33, and 35 include sensor circuit arrangements employing multiple coil windings and a single core adapted to be positioned with the sensor windings that, depending upon the specific configuration, provide: indications of movements relative to a reference position, very accurate indications of movements, generally temperature insensitive operation, directions of movements, and temperature measurements. The outputs of FIGS. 33 and 35 are provided that are proportional to the ratio of inductive reactance of the input excitation windings and not impedance.

FIG. 31 includes a sensor circuit 601 wherein the excitation winding is divided into two separate windings 604A and 604B that function as a single winding and a single core 603 (illustrated symbolically by two arrows) adapted to move and extend into the windings 604A and 604C approximately equally, and to extend into windings 604B and 604D approximately equally. A pulse from the capacitor 96 is discharged through resistor 600, the series connected windings 604A and 604B, and the resistor 602. The two pick up windings 604C and 604D are connected in series to oppose each other. The circuit provides a sensor arrangement wherein at sensor midpoint core position the output of the pick up windings are nullified, thereby providing an accurate position sensor circuit arrangement that is essentially temperature insensitive, particularly if the voltage is sensed as close as possible to the capacitor discharge. The reason for the insensitivity to temperature at the initial discharge is that this embodiment gives a voltage out that is the supply voltage (the voltage across the capacitor 96) multiplied by the ratio of the difference of the inductance between the windings 604A and 604B to the sum of the inductance of those same windings, hence independent of the core relative permeability and coil resistance. The zero crossing time can also be monitored as a sensitive indication of temperature drift.

FIG. 32 includes a plot of the waveform outputs of the sensor circuit arrangement of FIG. 31. The position of core 603 relative to the two excitation windings 604A and 604B is illustrated for three examples of core disposition. In the position 611A the core 603 has a deep displacement within winding 604A (and lesser in 604B) having an output represented by curve 609A, in the position 611B the core 603 is less displaced within winding 604A having an output represented by curve 609B, and in the position of 611C the core 603 is equally displaced in windings 604A and 604B having an output represented by curve 609C. With similar larger displacement within winding 604B, the outputs are represented by the curves 609D and 609E. As can be seen, when equal core displacement is achieved, a zero signal is outputted, and hence an accurate indication of position is provided which can be used as a control signal for controlling the position of the item being monitored.

FIG. 33 is a block diagram of a monitoring circuit of the invention for use with the sensor circuit 601 of FIG. 31. A pulse is applied by the generator 170 to the series excitation windings 604A and 604B of the sensor 601. The difference output from the pick up windings 604C and 604D, as illustrated by the curves of FIG. 32, can have a positive or negative polarity, depending upon the positioning of the core 603. Because of the polarity changes from the sensor 601, the amplifier 581, the sample and hold 583, and the inverter 584 are bipolar signal responsive circuits. Alternately the ground connections of the sensor circuit 601 can be replaced with an offset power supply voltage to allow the output from the sensor circuit 601 to vary about a positive reference. Since the microcontroller 164 only responds to signals of a singular polarity (usually positive), the inverter circuit 584 provides a positive output when the sensor circuit output is negative as so identified by the sample and hold 583 via the connection 584 to the microcontroller 164.

Figure 34:
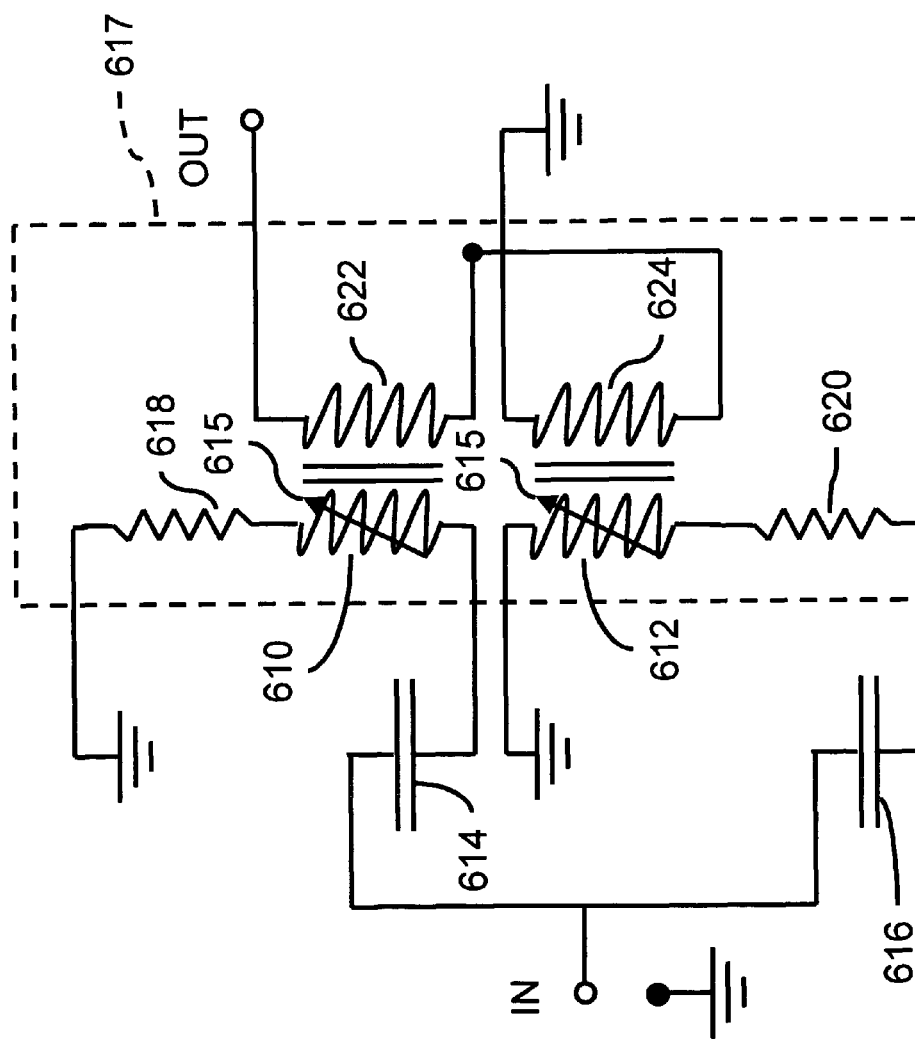
FIG. 34 includes a schematic diagram of another embodiment of a sensor circuit of the invention including two excitation windings and two pick up windings.

The sensor circuit 617 of FIG. 34 includes two excitation windings 610 and 612 including a single core 615 (illustrated symbolically by two arrows) adapted to extend into both windings and separate capacitors 614 and 616 to apply pulses of current through winding 610 and resistor 618 and winding 612 and resistor 620 respectively. Separate pick up windings 622 and 624 are connected in series opposition to subtract signals.

FIG. 35 includes a plot of the waveform outputs of the sensor circuit arrangement of FIG. 33. The position of core 615 relative to the two excitation windings 610 and 612 is illustrated for three examples of disposition. In the position 623A the core 615 has an effective deeper displacement within winding 610 and lesser in winding 612, having an output represented by curve 621A, in the position 623B the core 615 is less displaced within winding 610 and more in winding 612 having an output represented by curve 621B, and in the position of 623C the core is equally displaced in windings 610 and 612 having an output represented by curve 621C. With similar larger displacement within winding 621, the outputs are represented by the curves 621D and 621E. As can be seen, the curves of FIG. 35 are of positive and negative polarity and are initially close to zero volts at time T0 and have a zero crossing at time T1. A very accurate measurement of displacement, with a very low signal to noise ratio, relative to directions about a reference point, can be achieved by integrating the output between times T0 and T1, particularly in noisy situations for improved signal to noise ratio. The integrated waveform itself would not be strictly temperature insensitive at other than the neutral state, since subtraction of the signals does not effectively nullify temperature effects in an offset condition. The peak value of the waveforms are temperature insensitive, particularly when the individual windings are in an over damped condition. An indication of temperature drift can be achieved by monitoring the zero crossing time.

Figure 36:
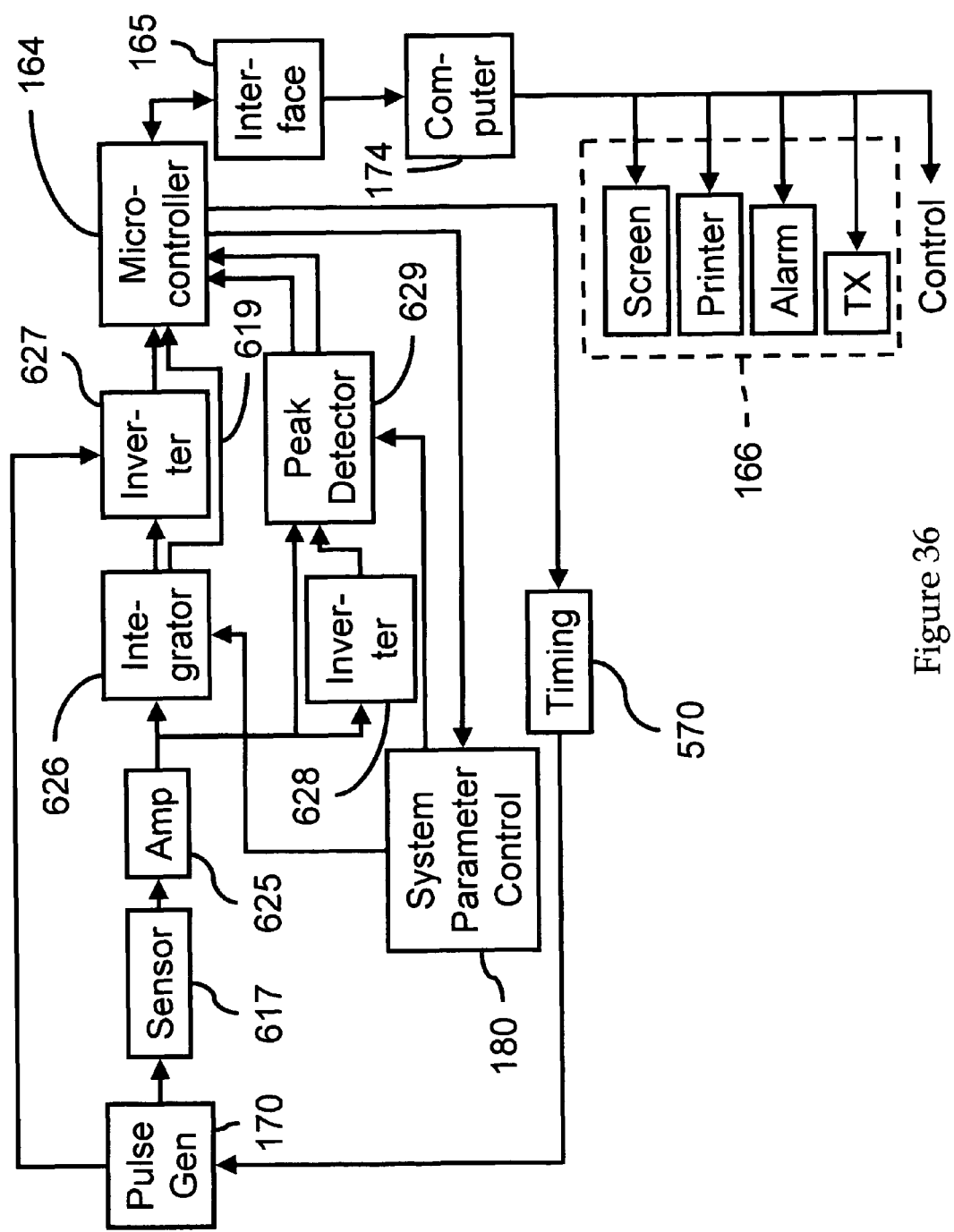
FIG. 36 is a block diagram of a monitoring system for use with the sensor circuit of FIG. 34.

FIG. 36 is a block diagram of a monitoring circuit of the invention for use with the sensor circuit 617 of FIG. 34. A pulse is simultaneously applied by the generator 170 to both the excitation windings 610 and 612 of the sensor 617. The difference output from the pick up windings 622 and 624, as illustrated by the curves of FIG. 35, have two zero volt crossings and can have a positive or negative polarity, depending upon the positioning of the core 615. Because of the polarity changes from the sensor 617, the amplifier 625, the integrator 626, the inverters 627 and 628 and the peak detector 629 are bipolar signal responsive circuits. Alternately the ground connections of the sensor circuit 617 can be replaced with an offset power supply voltage to allow the output from the sensor circuit 617 to vary about a positive reference. Since the curves of FIG. 35 have two zero points, the signal output from the sensor 617 can be integrated between two points to provide an output signal to the inverter 627 having increased signal to noise ratio. Since the microprocessor 164 only responds to signals of a singular polarity (usually positive), the inverter circuit 627 provides a positive output when the sensor circuit output is negative as so identified by the integrator 626 via the connection 619 to the microprocessor 164. The signal from the integrator 626 is applied to the peak detector 629 directly or through an inverter 628. The peak detector having a sample and hold circuit for each polarity selects the peak value of a curve to provide an output that is independent of temperature. The system parameter control 180 controls the start, stop and reset of the integrator 626 and the peak detector 629. Care should be taken to control the value of the parasitics in the sensor circuit, as an imbalance in the parasitics can for example prevent the voltage at time To from being zero and build in a finite slope in curve 621C. Compensation circuitry can be added to offset such imbalance.

Figure 37:
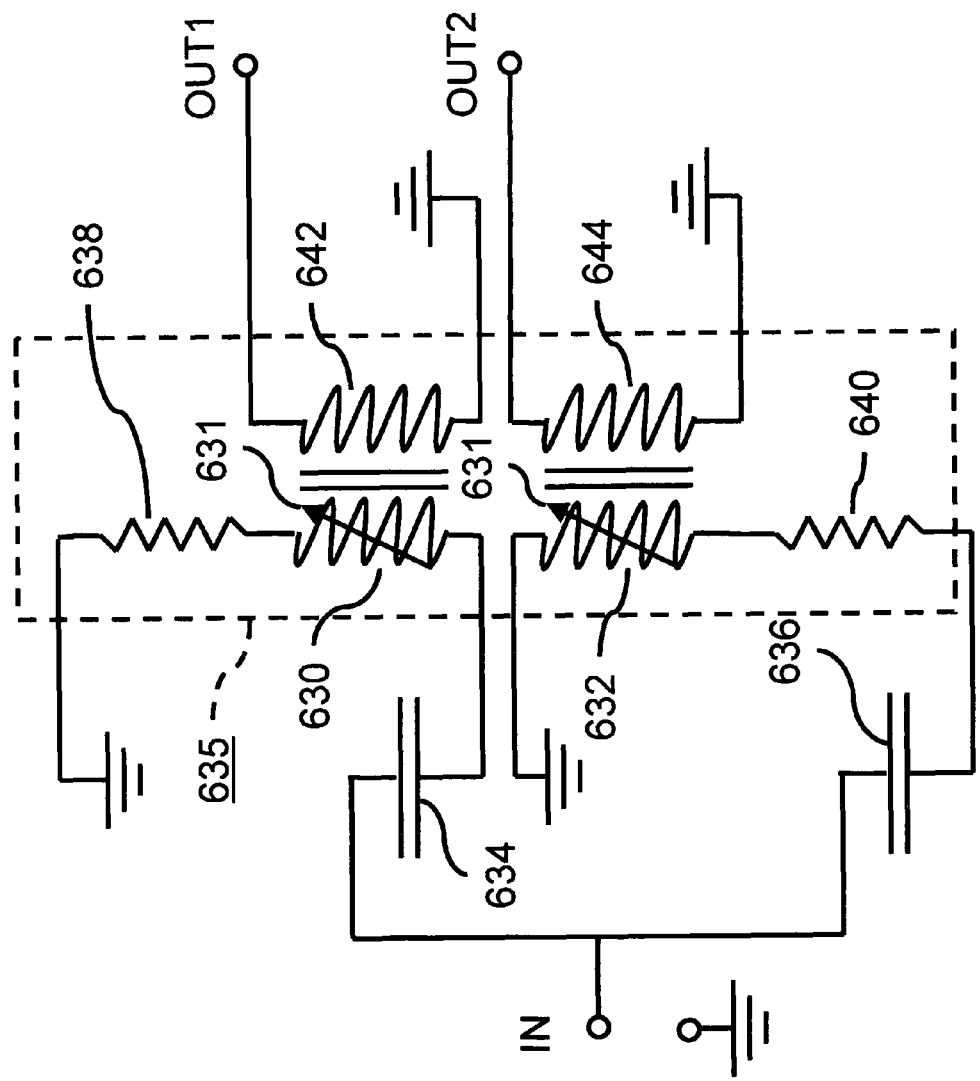
FIG. 37 includes a schematic diagram of another embodiment of a sensor circuit of the invention including two excitation windings and two pick up windings.

The sensor circuit 635 of FIG. 37 includes two sensors, each having excitation windings 630 and 632 and separate pick up windings 642 and 644 respectively and a single core 631 (illustrated symbolically by two arrows) adapted to extend into both windings. Separate capacitors 634 and 636 apply current pulses through the winding 630 and resistor 638 and winding 632 and resistor 640 respectively. The pick up windings 642 and 644 provide separate outputs are responsive to the pulse excitation of windings 630 and 632 respectively. The zero crossing time, or other convenient decay time of each pick up winding is monitored to provide a time based measuring system. The ratio thus obtained gives an indication of displacement that is temperature insensitive.

Figure 38:
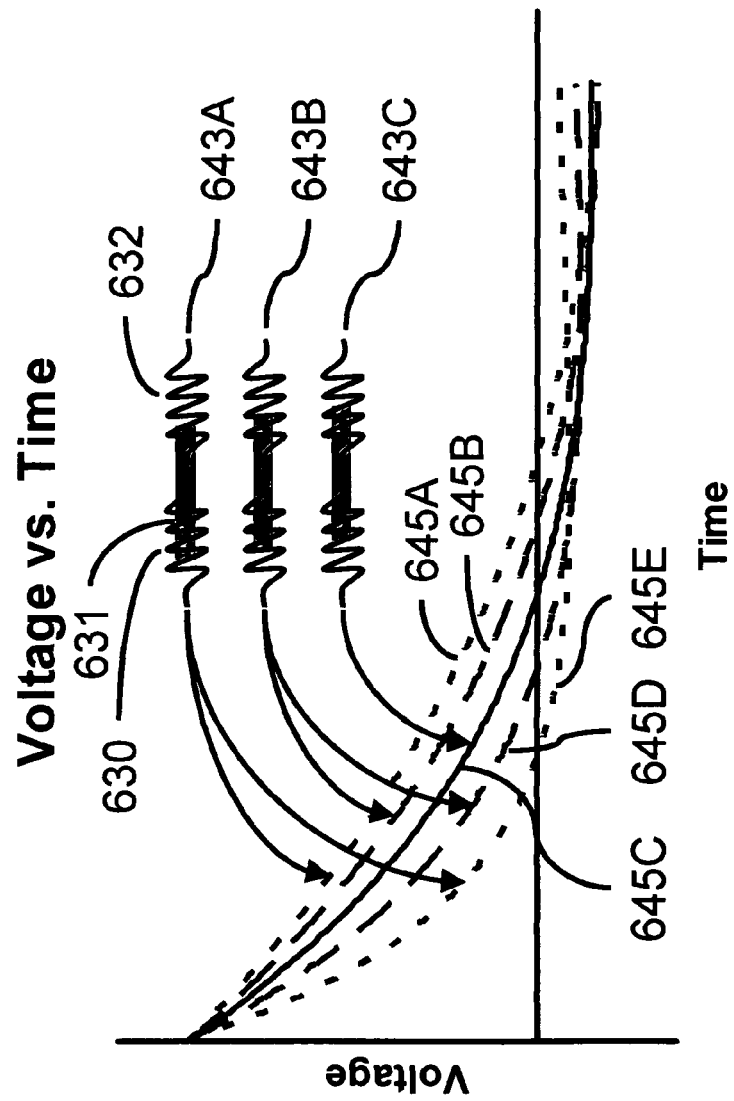
FIG. 38 includes waveforms for illustrating the operation of the sensor circuit of FIG. 37.

FIG. 38 includes a plot of the waveform outputs of the sensor circuit of FIG. 35. The position of core 631 relative to the two excitation windings 630 and 632 is illustrated for three examples of disposition. In the position 643A the core 631 has a deeper displacement within winding 630 and lesser displacement in winding 632 having outputs represented by curves 645A and 645E, in the position 643B the core 631 has moved toward the neutral position having outputs represented by curves 645B and 645D, and in the position of 643C the core 631 is in the neutral position equally displaced in windings 630 and 632 having an output represented by curve 645C. As can be seen the two sensor have separate outputs with two separate zero crossings. A very accurate of displacement can be achieved by measuring the time when each curve crosses zero, and then ratioing the zero crossing times to provide an accurate indication of displacement that is essentially temperature insensitive. Again ratioing provides constant readings despite changes in the relative permeability of the core, particularly in the over damped condition. In addition, the average of the zero crossing times can be monitored as an indication of the temperature.

The two separate outputs from the sensor circuit 635 can be applied to separate monitoring circuit of FIG. 29 for processing. Triggers can be established such that at times from T0 to the individual sensor output crossing points are monitored, or alternately the time between zero and the first sensor output crossing point can be obtained followed by obtaining the time between the first sensor output crossing point and the second sensor output crossing point.

Although the circuits disclosed in FIGS. 31, 34 and 37 are illustrated with separate resistors, it should be understood that these resistor can represent the intrinsic resistance of the windings or external resistors. Further since the capacitive pulsing of the sensors are illustrated as series circuits, the position of the resistors and winding can be interchanged. While the capacitors are shown as separate capacitors in FIGS. 31, 34 and 37, meaningful measurements can also be made by combining these two capacitors into a single capacitor. In addition, input coils (shown in alliance) and the pick up coils (shown in opposition) can be rearranged wherein the input coils are in opposition and the output coils are in alliance.

In the embodiments of the system apparatus of the invention described above the microcontroller 164 outputs digital data indicative of the sensor displacement to the computer 174, which can be, for example a standard lap top computer including a screen and an alarm for providing visual and audible outputs of the display unit 166. The computer 174 also provides a control signal that can be used for controlling the movements of the object being monitored. However it should be understood that the microcontroller 164 and the computer 174 can be combined in a single unit specifically tailored to function as a single piece of specialized medical monitoring equipment, such as found in medical testing apparatus only needing to be plugged in to power and the sensors attached to the patient under test.

The invention provides solutions for applications requiring the monitoring delicate items or flexible membrane, such as skin, with insignificant interference from the monitoring apparatus. By insignificant interference it is meant that the sensor, its size, its mass, its loose fitting parts (for longitudinal, rotation and wobble) and the flexible electrical connections thereto does not place restrictive forces on the portion or part of the membrane under test having a magnitude that would detrimentally impact the accuracy of the measurements.

The invention, as described in previous embodiments, may be attached to the human skin in a variety of positions and in multiple locations. In its miniaturized form the tiny, lightweight sensor does not require the cumbersome use of jackets or belts that inhibit freedom of movement and are uncomfortable for long periods of time. This invention permits sensitive surveillance in the micron range allowing monitoring for small changes in breathing patterns of a sleeping infant or adult while barely perceptible the wearer.

The design of the sensor provides the capability of making sensors small in size allowing their placement on nearly all areas of the body such as the chest, abdomen, neck, back, and penis, legs, arms among others, allowing invention to be used for observing a wide variety of physiological symptoms. In an embodiment, the sensor may be attached to the skin with a "Band-aid" type bandage, for easy installation by less skilled technicians and provide protection for the sensor from outside interference, like clothing.

On the other hand, if monitoring massive objects, such as for example, automobile shock absorbers, where the sensor would be exposed to difficult environmental conditions, the loose mechanical fit may not be appropriate, requiring seals and sealed electrical connections, but so as not to interfere with the shock absorber operation. However, the coil and sensor configuration, the excitation of the sensor by pulses and the output of decaying signals, the monitoring circuits, systems, and method of the invention will apply to such ruggedized versions of the sensor of the invention.

The monitoring system of the invention also includes an automatic system parameter presetting or adjusting arrangement that provides corrected system operation should conditions change. With this type of arrangement the sensor does not significantly impact the freedom of a patient's movement, allowing the patient to more easily continue with many normal activities. If a sudden movement should interrupt the monitoring process, the system will be automatically reset.

Additionally, a plurality of the sensors may be placed such that they cover a wide range of area on the human body as in the case of labor contractions in abdomen of a pregnant woman. Sensors may be place in various patterns on the abdomen to track deformations such as expansion and contraction of the skin in a topographical array to provide analysis of skin displacements which may occur in waves.

Specific applications and exemplary embodiments of the invention have been illustrated and discussed, which provides a basis for practicing the invention in a variety of ways and in a variety of applications. Numerous variations are possible within the scope of the invention. Features and elements associated with one or more of the described embodiments are not to be construed as required elements for all embodiments. Other changes and modifications in the specifically described embodiments can be carried out without departing from the principals of the invention that is intended to be limited only by the scope of the appended claims, as interpreted in accordance with the principals of patent law, including the doctrine of equivalents.

What is claimed:

1. A sensor system for monitoring the displacement between movable parts of an object comprising:
    an electrical sensor comprising two components, one component being adapted to be positioned within the other for generally linear movement there between, and having input and output circuits, wherein the electrical impedance of the sensor changes as a function of the relative displacement between the components, the components of the sensor being adapted to be attached to different movable parts of the object for providing impedance changes corresponding to displacements;
    a circuit for applying pulses to the input circuit wherein the output winding outputs decaying signals, the rate of decay being a function of the relative displacement between the components, and
    a monitoring circuit is responsive to the output signal decay rate for providing indications of the displacements between the movable parts of the object,
    wherein the sensor components comprises a coil having an input winding and an output winding and a magnetic core extending into the coil for generally linear relative movement there between,
    wherein the inductance of the sensor changes as a function of the relative displacement between the core and the coil, the coil and core being adapted to be attached to different movable parts of the object,
    wherein the monitoring circuit comprises a circuit for measuring the amplitude of the decaying signal after the application of the pulses to the sensor as an indication of the displacements,
    wherein the monitoring circuit includes a storage circuit for storing the magnitudes of the decaying signals at selected times subsequent to the application of the electrical pulses,
    wherein the monitoring circuit varies the relative timing between the application of the electrical pulses and the operation of the storage circuit, and
    wherein the monitoring circuit comprises:
    a circuit for amplifying the magnitude of the decaying signals and applying the value of the amplified signals at controlled times to the storage circuit;
    a circuit for sensing when the values of the decaying signals from the amplifying circuit are in saturation or below a reference level, and
    the control circuit is responsive to the sensing circuit to adjusts the controlled times in a direction so that the amplifier circuit operates between saturation and the reference level.

2. A sensor system as defined in claim 1 comprising:
    an analog to digital converter circuit for converting the magnitudes of the storage circuit to digital form, and
    the control circuit performs an analysis of the digital signals to determine when the magnitudes of the decaying signals fall within saturation and reference level operating range of the amplifying circuit.

3. A sensor system as defined in claim 2 wherein the control circuit determines when the magnitudes of the decaying signals from the amplifier approach saturation or the reference level for varying the relative timing between the application of the electrical pulses and the operation of the storage circuit.

4. A sensor system as defined in claim 3 comprising apparatus for providing a visual display of the magnitudes of the decaying signals stored in the storage circuit as an indication of the displacement between the movable portions of the object.

5. Monitoring apparatus for use with a sensor that includes at least two movable parts adapted to be attached to separate parts of an object, and wherein the electrical impedance of the sensor varies as a function of the disposition of the two parts relative to each other, the apparatus comprising:
    a circuit for applying time separated electrical pulses to the sensor, and
    a circuit for analyzing the response of the sensor to the electrical pulses in the form of a decaying signals, the duration of which is a function of the impedance of the sensor, to provide an indication of changes in the disposition between the movable parts,
    wherein the analyzing circuit selects the timing for making subsequent measurements so that the level of magnitudes is within a predetermined range,
    wherein the analyzing circuit comprises:
    an amplifier circuit for amplifying the magnitude of the decaying signals, wherein the response of the amplifier is adapted to be driven into non-linear operation, and
    wherein the predetermined range of magnitudes for selecting the timing falls within the linear operation of the amplifier; and
    wherein the analyzing circuit determines when the output of the amplifier is driven near the non-linear operation of the amplifier to change the timing for subsequent measurements.

6. Monitoring apparatus for use with a sensor that includes at least two movable parts adapted to be attached to separate parts of an object, and wherein the electrical impedance of the sensor varies as a function of the disposition of the two parts relative to each other, the apparatus comprising:

a circuit for applying time separated electrical pulses to the sensor, and a circuit for analyzing the response of the sensor to the electrical pulses in the form of a decaying signals, the duration of which is a function of the impedance of the sensor, to provide an indication of changes in the disposition between the movable parts, wherein the sensor includes a coil and a ferromagnetic core adapted to be located for movement within the coil, the coil and core being adapted to be attached to separate movable parts of an object, and the inductive reactance of the sensor varies as a function of the disposition of the coil and core relative to each other over the scope of movements, and wherein the analyzing circuit comprises:

one or more operation parameters, and a control circuit programmed to process a range of signals from the sensor and for resetting the operation parameters of the analysis circuit in the event the sensor inductive reactance changes exceed the range.

7. Monitoring apparatus as defined in claim 6 where the analyzing circuit comprises an amplifier and the control circuit monitors the output of the amplifier circuit to determine when the range of amplified signals exceeds the linear operation of the amplifier for resetting the parameters of the analyzing circuit for amplifier linear operation.

8. Monitoring apparatus as defined in claim 7 wherein the amplifier is a variable gain amplifier, and the control circuit monitors the output of the amplifier circuit to modify the gain of the amplifier if the amplifier operates at levels approaching saturation or zero.

* * * * *